United States Patent
Wang et al.

(10) Patent No.: US 11,091,799 B2
(45) Date of Patent: Aug. 17, 2021

(54) AMPLIFICATION WITH PRIMERS OF LIMITED NUCLEOTIDE COMPOSITION

(71) Applicant: ATILA BIOSYSTEMS INCORPORATED, Palo Alto, CA (US)

(72) Inventors: Youxiang Wang, Mountain View, CA (US); Zhijie Yang, Mountain View, CA (US); Xin Chen, Mountain View, CA (US)

(73) Assignee: ATILA BIOSYSTEMS INCORPORATED, Palo Alto, CA (US)

(*) Notice: Subject to any disclaimer, the term of this patent is extended or adjusted under 35 U.S.C. 154(b) by 452 days.

(21) Appl. No.: 15/569,080

(22) PCT Filed: Apr. 22, 2016

(86) PCT No.: PCT/US2016/029054
§ 371 (c)(1),
(2) Date: Oct. 24, 2017

(87) PCT Pub. No.: WO2016/172632
PCT Pub. Date: Oct. 27, 2016

(65) Prior Publication Data
US 2018/0148775 A1 May 31, 2018

Related U.S. Application Data

(60) Provisional application No. 62/152,756, filed on Apr. 24, 2015.

(51) Int. Cl.
*C12Q 1/6848* (2018.01)

(52) U.S. Cl.
CPC ..... *C12Q 1/6848* (2013.01); *C12Q 2525/101* (2013.01); *C12Q 2525/143* (2013.01); *C12Q 2525/161* (2013.01); *C12Q 2525/301* (2013.01); *C12Q 2527/137* (2013.01); *C12Q 2527/143* (2013.01); *C12Q 2565/107* (2013.01)

(58) Field of Classification Search
CPC ............ C12Q 1/6848; C12Q 2525/301; C12Q 2525/101; C12Q 2525/143; C12Q 2565/107; C12Q 2527/143; C12Q 2525/161; C12Q 2527/137
See application file for complete search history.

(56) References Cited

U.S. PATENT DOCUMENTS

| 2006/0014167 | A1* | 1/2006 | Church | C12Q 1/6846 435/6.12 |
| 2007/0178453 | A1* | 8/2007 | Rujan | C12Q 1/6858 435/6.12 |
| 2009/0036315 | A1 | 2/2009 | Labgold et al. | |
| 2010/0035303 | A1* | 2/2010 | Rhee | C12Q 1/6844 435/91.2 |
| 2011/0294129 | A1 | 12/2011 | Ali et al. | |
| 2013/0115595 | A1 | 5/2013 | Hantash et al. | |
| 2014/0065613 | A1 | 3/2014 | Bormann Chung et al. | |
| 2014/0228254 | A1 | 8/2014 | Adessi et al. | |
| 2014/0274811 | A1* | 9/2014 | Arnold | C12N 15/1065 506/26 |
| 2015/0232929 | A1* | 8/2015 | Stephens | C12Q 1/6853 506/4 |
| 2016/0208322 | A1 | 7/2016 | Anderson et al. | |

FOREIGN PATENT DOCUMENTS

| JP | 2006519621 A | 8/2006 |
| JP | 2010539971 A | 12/2010 |
| WO | WO 06/058393 | 6/2006 |
| WO | WO 16/172632 A2 | 10/2016 |
| WO | WO 19/033065 A1 | 2/2019 |

OTHER PUBLICATIONS

Yao et al. Journal of Biological Chemistry 1994; 269: 16260-16268. (Year: 1994).*
Vet et al. Methods in Molecular Biology 2005; 288: 273-290. (Year: 2005).*
Tyagi et al. Nature Biotechnology 1996; 14: 303-308. (Year: 1996).*
Henriques et al. In silico vs in vitro analysis of primer specificity for the detection of Gardnerella vaginalis, Atopobium vaginae and *Lactobacillus* spp. BMC Research Notes 2012; 5: 637 (Year: 2012).*
Gen Bank Accession No. EF421234.1 for *Homo sapiens* short tandem repeat vWA variant 18 genomic sequence. Jun. 3, 2009, [online], retrieved from the Internet: <www.ncbi.nlm.nih.gov/nuccore/ef421234.1> (Year: 2009).*
Braun et al., "Detecting CFTR Gene Mutations by Using Primer Oligo Base Extension and Mass Spectrometry," Clinical Chemistry, 43(7): 1151-1158, (1997).
Zeng et al., "Array-MLPA: comprehensive detection of deletions and duplications and its application to DMD patients," Human Mutation, 29(1):190-197, doi: 10.1002/humu.20613, (2008).
EP Application No. 16784032.1 (Published as EP3286338), Supplementary European Search Report and European Search Opinion dated Nov. 16, 2018.

(Continued)

*Primary Examiner* — Angela M. Bertagna
(74) *Attorney, Agent, or Firm* — Alston & Bird LLP

(57) ABSTRACT

The invention provides methods of amplification from a single primer or a pair of forward and reverse primers of limited nucleotide composition. Limited nucleotide composition means that the primers are underrepresented in at least one nucleotide type. Such primers have much reduced capacity to prime from each other or to extend initiated by mispriming from other than at their intended primer binding sites in a target nucleic acid.

44 Claims, 41 Drawing Sheets
Specification includes a Sequence Listing.

(56) References Cited

OTHER PUBLICATIONS

Van Harmelen et al., "Increased Adipose Angiotensinogen Gene Expression in Human Obesity" Obesity Research, 8(4):337-341, (2000).
WIPO Application No. PCT/US2016/029054, PCT International Preliminary Report on Patentability dated Nov. 2, 2017.
WIPO Application No. PCT/US2016/029054, PCT International Search Report and Written Opinion of the International Searching Authority dated Dec. 1, 2016.
WIPO Application No. PCT/US2018/046360, PCT International Preliminary Report on Patentability dated Feb. 11, 2020.
WIPO Application No. PCT/US2018/046360, PCT International Search Report and Written Opion of the International Searching Authority dated Oct. 17, 2018.

\* cited by examiner

Fig. 1
(Example 1)
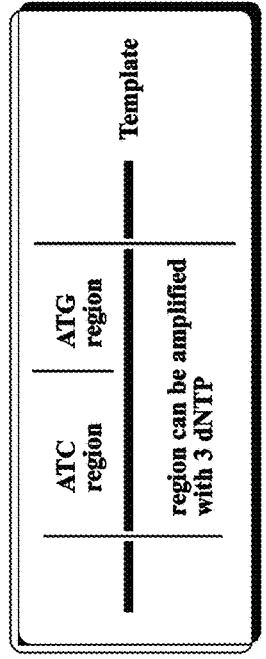
Below, G is under representative nucleotide in both forward and reverse primers amplification would need dTTP, dATP and dGTP only
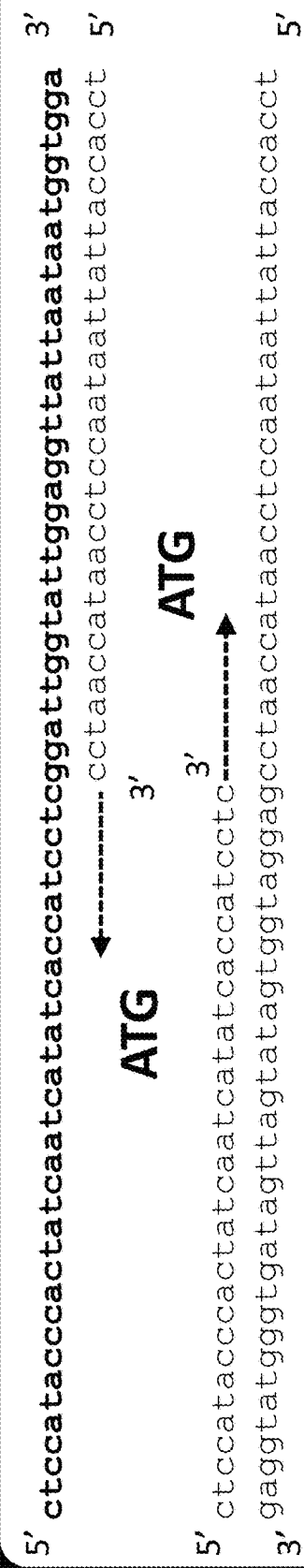

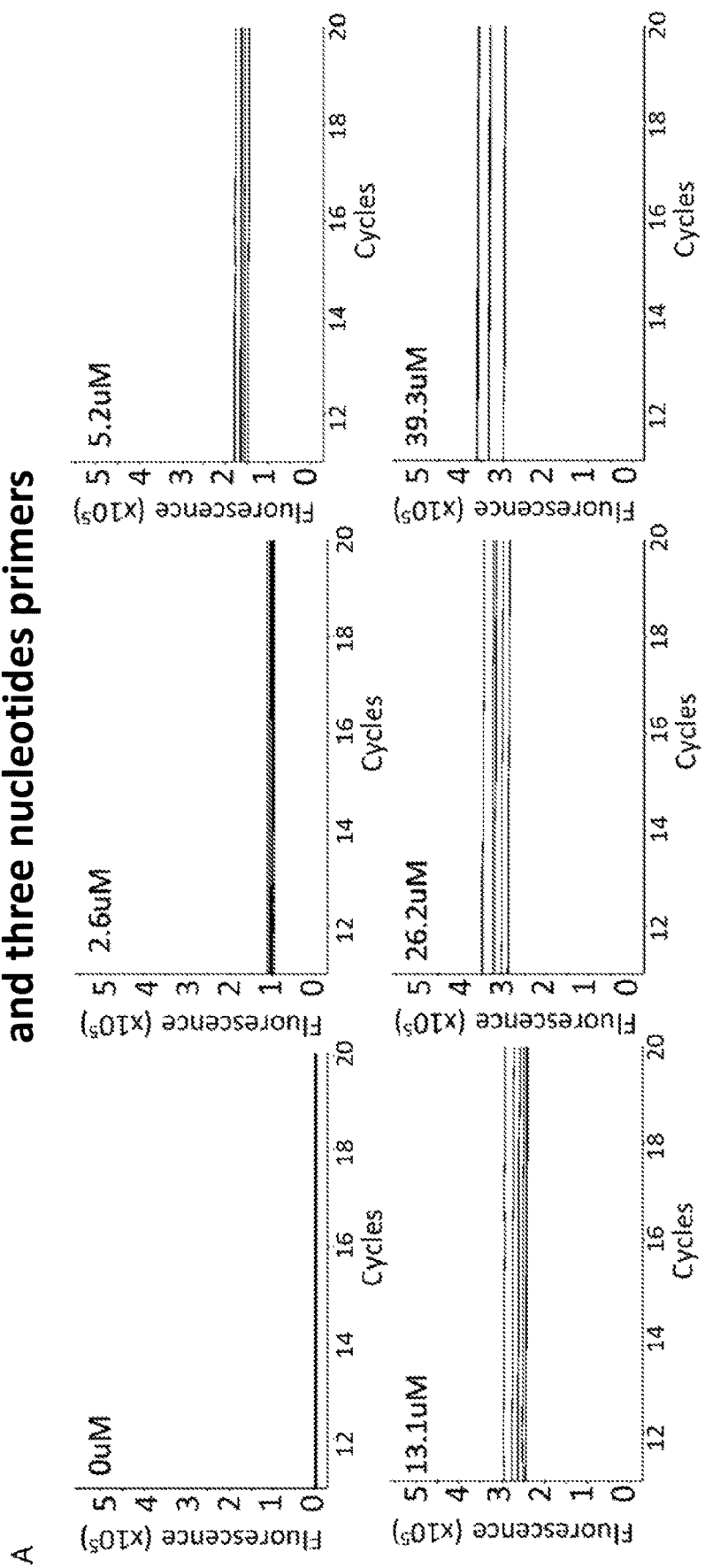
Fig. 2A (Example 2)
Comparison transient interaction between conventional primer and three nucleotides primers

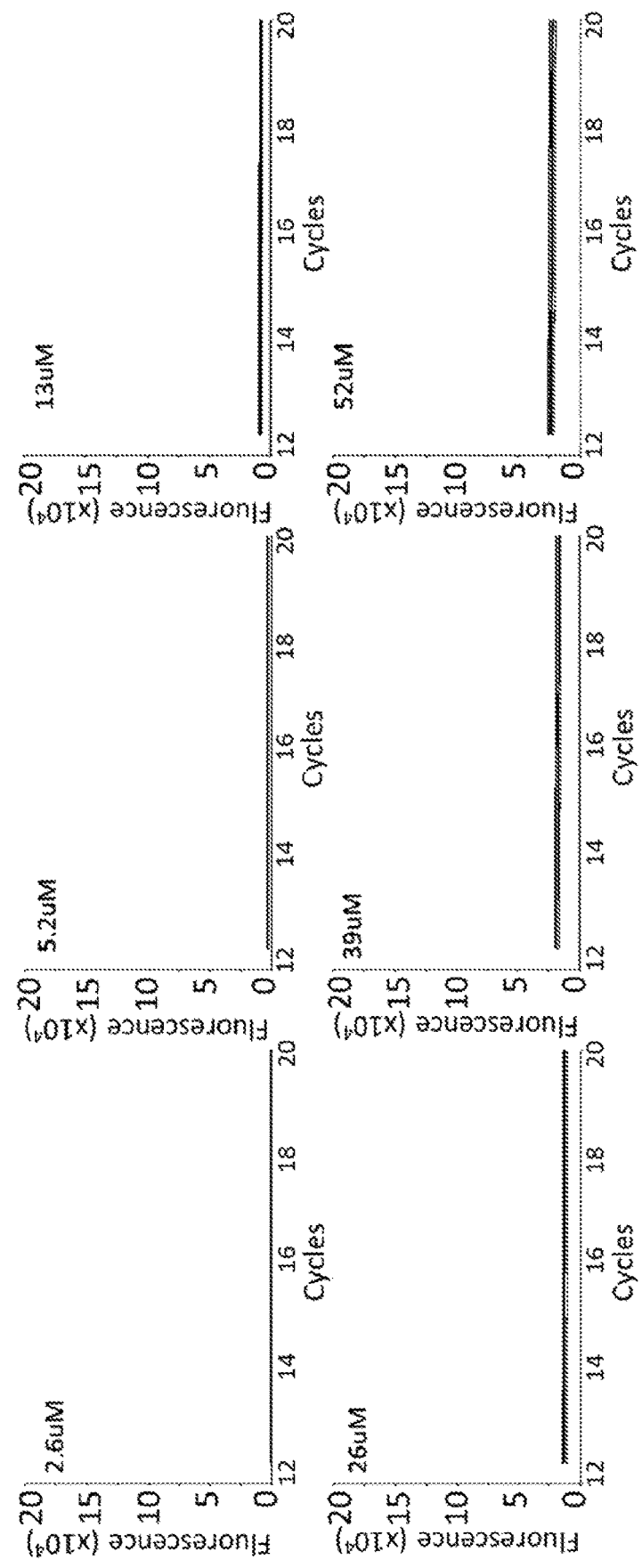
Fig. 2B (Example 2)
Comparison transient interaction between conventional primer and three nucleotides primers

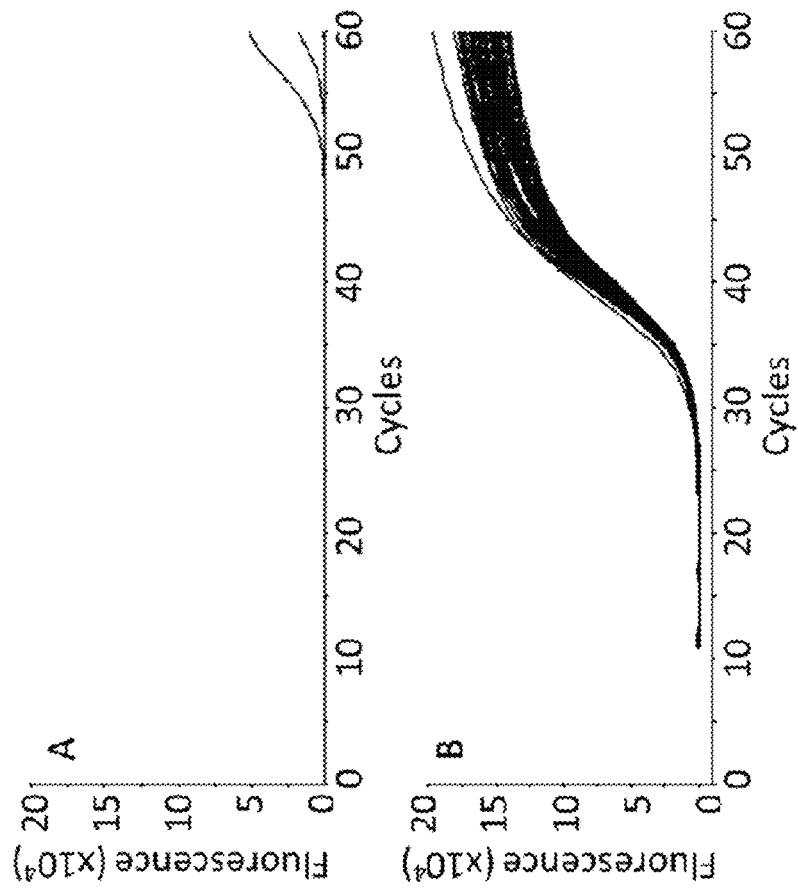
Figs. 3A-B (Example 3)
Comparison PCR false positive rate between conventional primer and three nucleotide primers

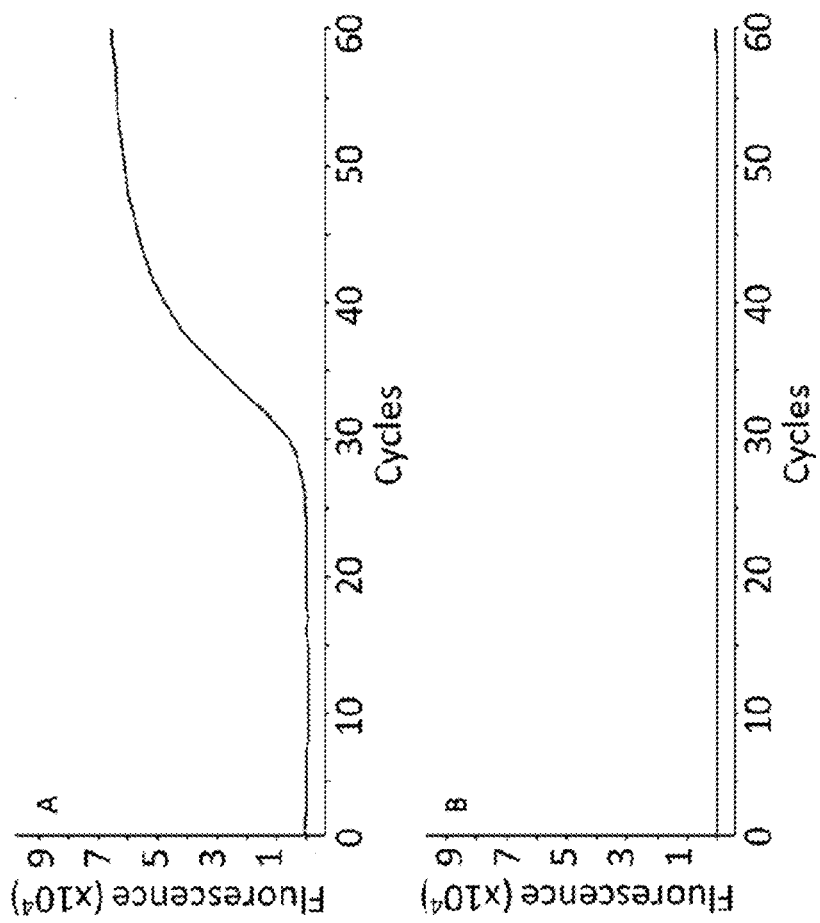
Figs. 4A, B (Example 4)
Real time PCR with three nucleotide primer and three nucleotide dNTP

Mismatch three nucleotides primers

Fig. 6
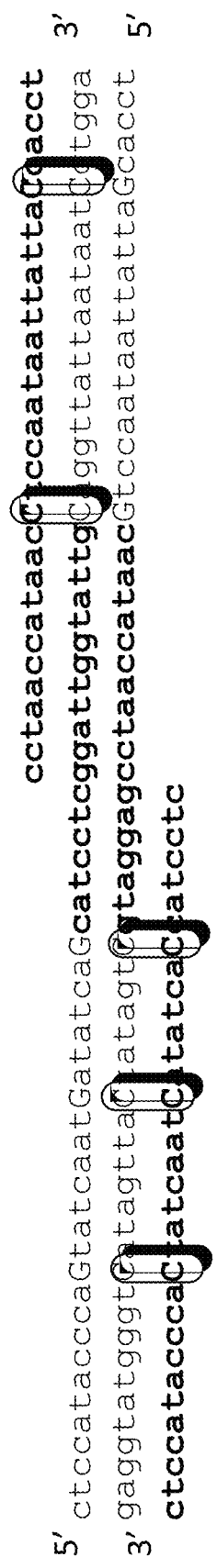
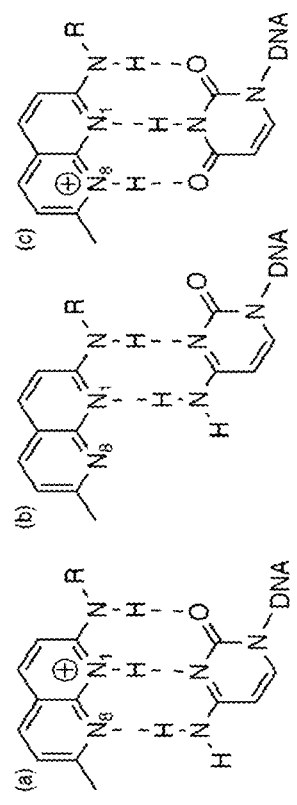

Three nucleotides primer amplify 4 Nucleotide Regions with four nucleotides dNTPs

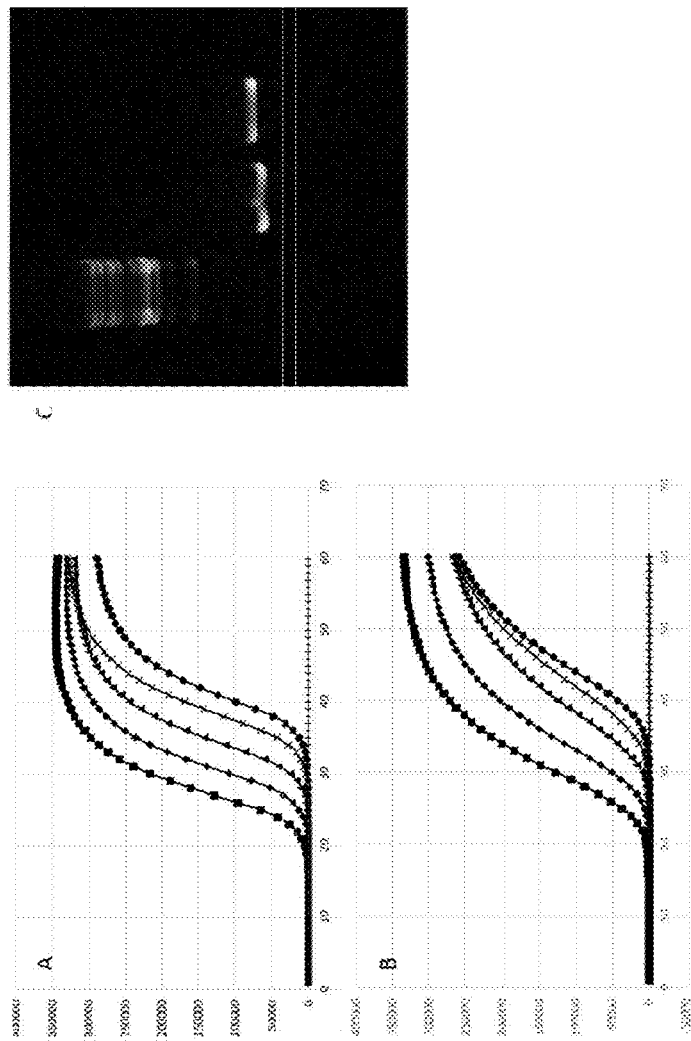
Figs. 8A-C (Example 5)
Three nucleotides primer with four nucleotides dNTPs

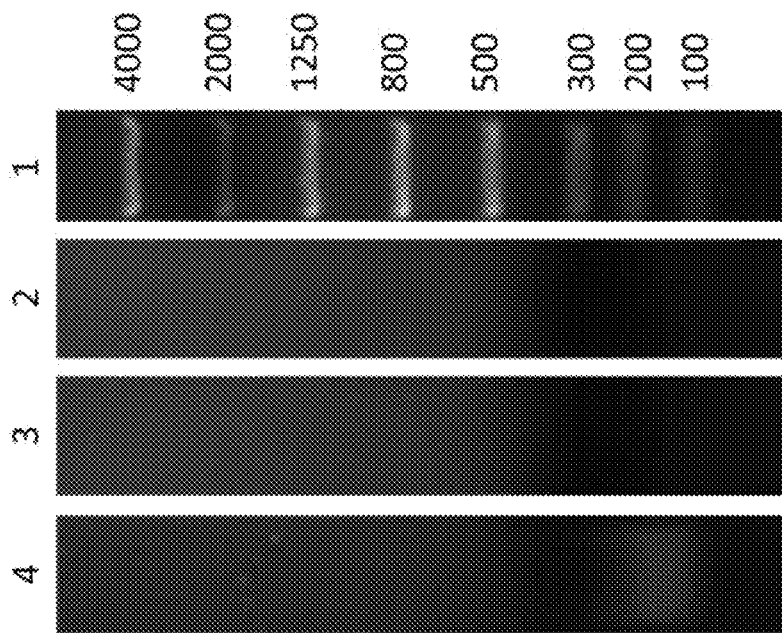
Fig. 9 (Example 8)
Comparison of primer dimer between three nucleotides primers and four nucleotide primers

Figs. 10A-D (Example 9)
Three Nucleotides Primer contains limited amount of underrepresentative nucleotides
Called constrained primer
cctaaccataacGtccaataattaCcacct   cctaaccataacGtccaataattaGcacct
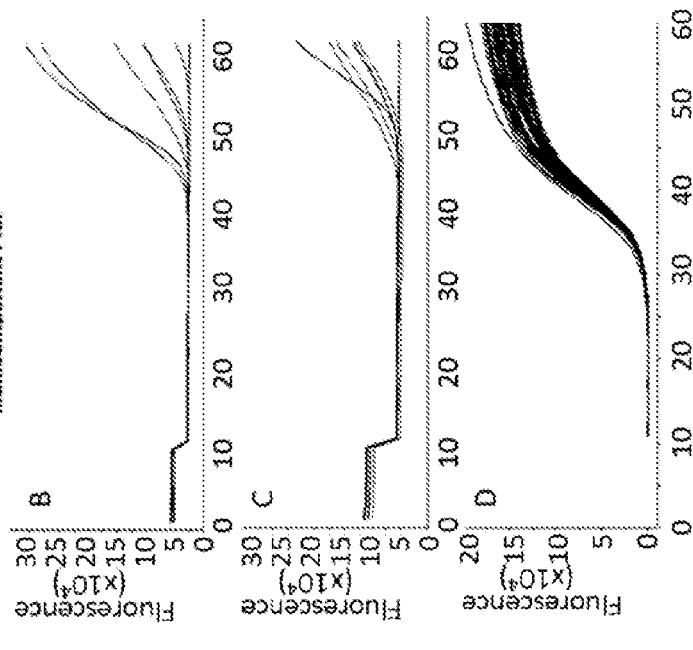
Primer-2 contains 3 nucleotides, except 2G only
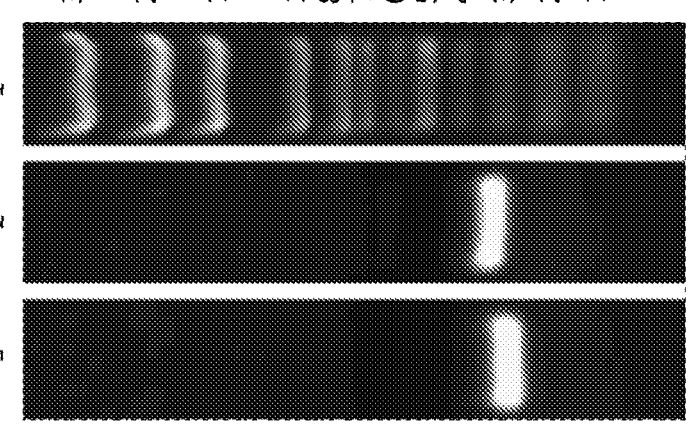
Primer-1 contains 3 nucleotides, except 1 G only

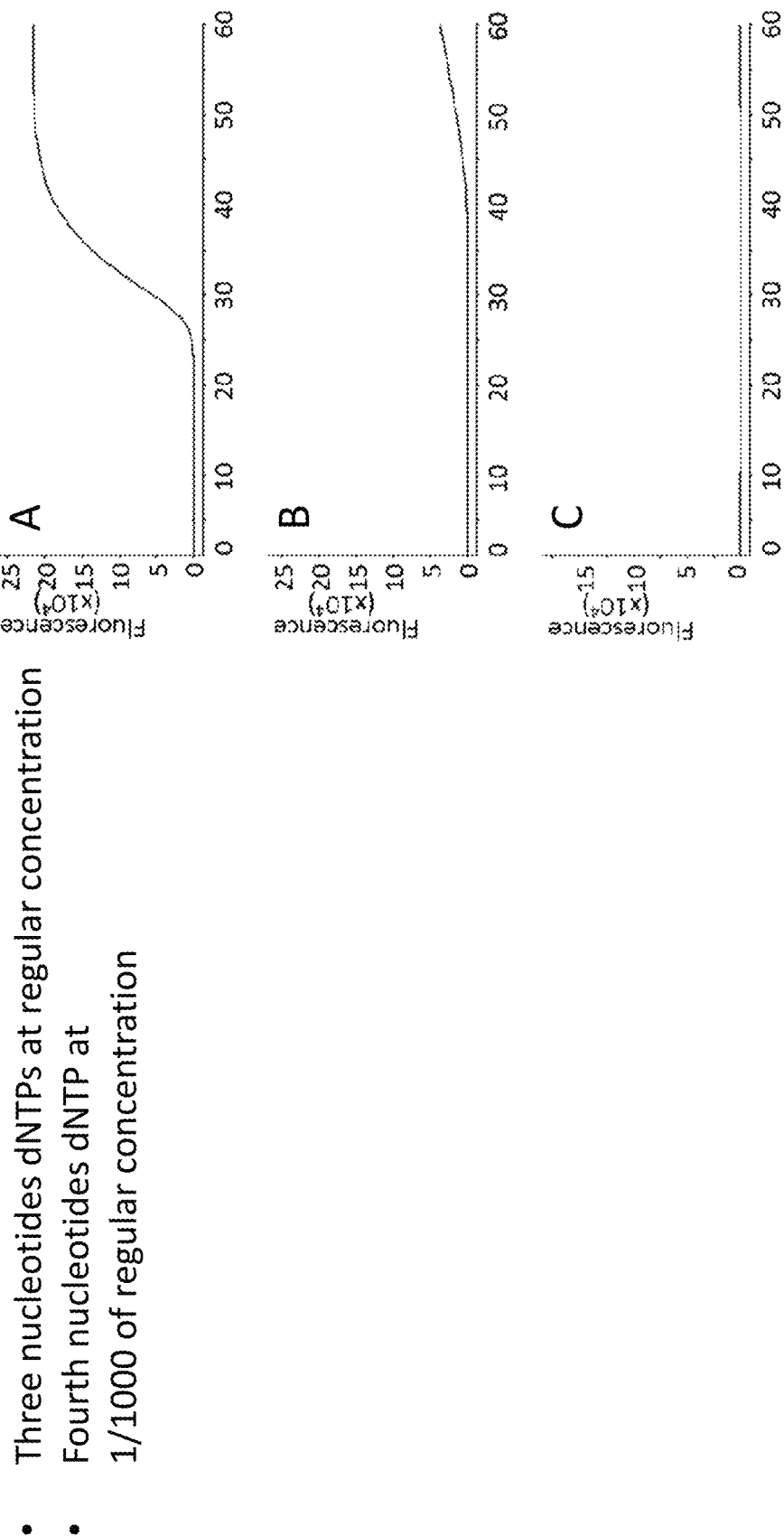
Figs. 11A-C (Example 12)
Constrained Primer with unbalanced dNTPs supply to further reduce False Positive
- Three nucleotides dNTPs at regular concentration
- Fourth nucleotides dNTP at 1/1000 of regular concentration

Fig. 12 (Example 13)
PCR with three nucleotides dNTPs and the fourth nucleotides as ddNTP to stop primer template mis-hybridization extension
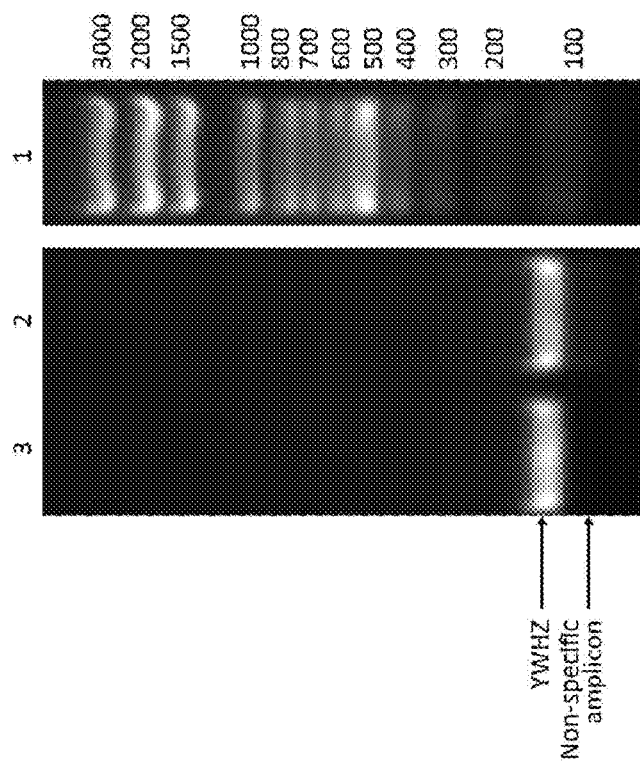

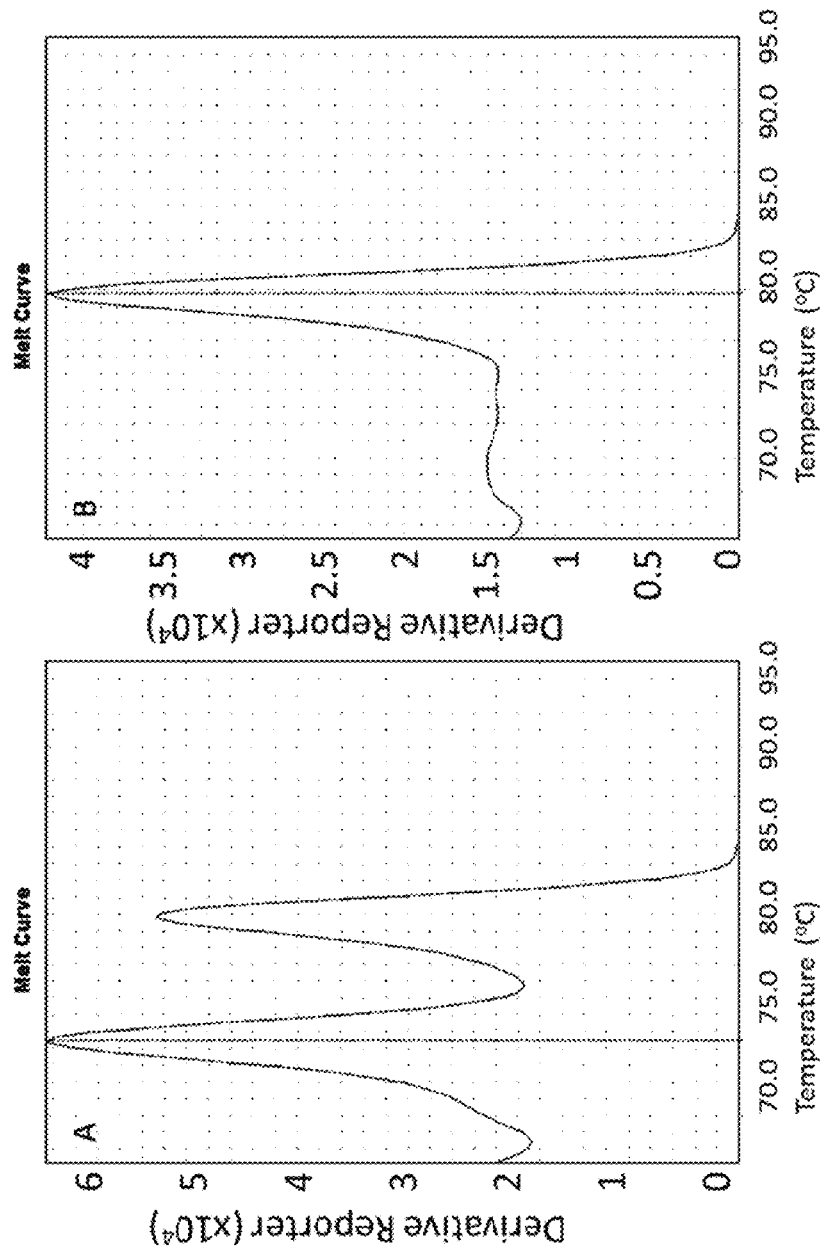
Figs. 13A, B (Example 14)
Multiplex detection of multi-templates with melting curve analysis Three nucleotides primer with 4 nucleotides Toehold sequence when one can not find long enough three nucleotides primer sequences Both sides can be Toehold primer as well Three nucleotides primer with 4 nucleotides Toehold sequence when one can not find long enough three nucleotides primer sequences Three nucleotides primer with three way junction sequences when one can not find long enough three nucleotides primer sequences

Figs. 17A, B

Three nucleotides primer with three way junction sequences when one can not find long enough three nucleotides primer sequences
Another format

Figs. 18A, B

Three nucleotides primer with three way junction sequences when one can not find long enough three nucleotides primer sequences
Another format Multiplex Amplification and Detection
3 dNTP primer contains tail with fluorescent and quencher dye probes Figs. 20A, B (Example 16)
Real time detection with fluorescent labeled three nucleotides primer Multiplex Amplification and Detection
3 dNTP primer contains tail with fluorescent and quencher dye probes
Asymmetric PCR to improve probe detection efficiency Molecular Beacon format Multiplex Amplification and Detection
3 dNTP primer contains tail with
Universal fluorescent and quencher dye probe format Amplification and detection of sticky end products Amplification and detection of circular products 3 Nucleotides Primer for Whole Genome Amplification Isothermal Amplification with Underrepresentative Primers

Fig. 30
Isothermal Amplification with Underrepresentative Primers
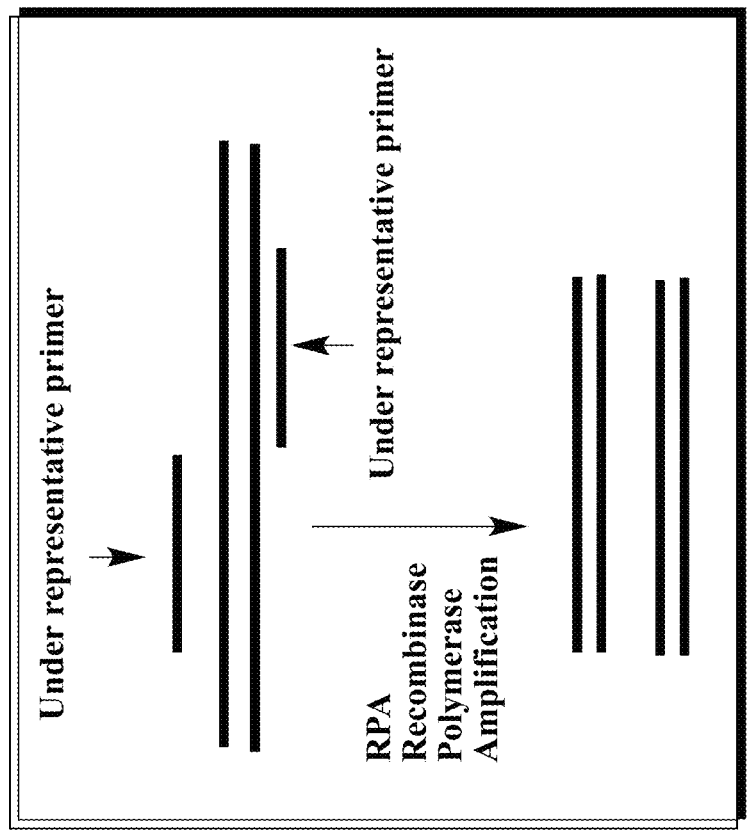
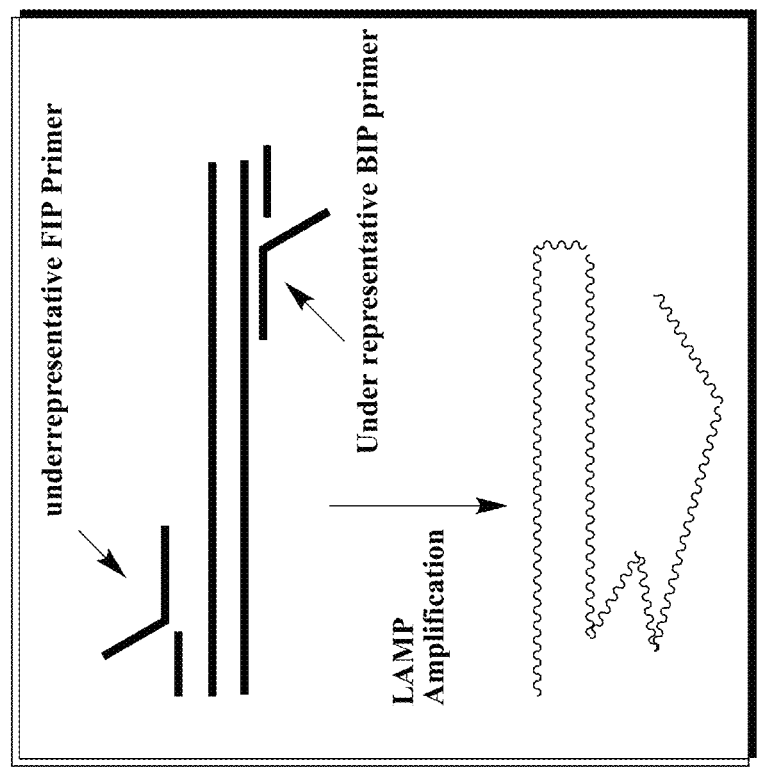

Figs. 31A-C
Isothermal Amplification with Three Nucleotides
A. Nicking Amplification
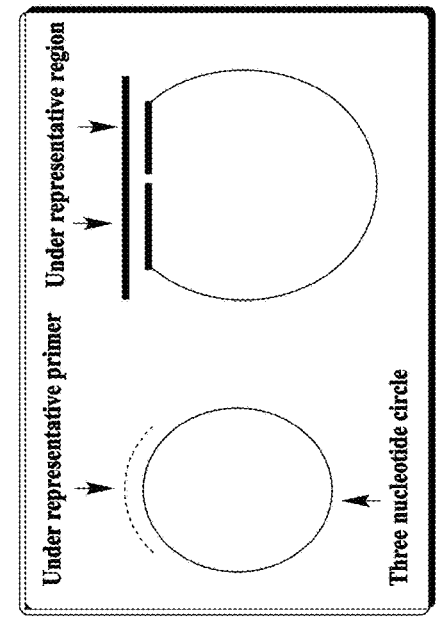
B. T7 Amplification
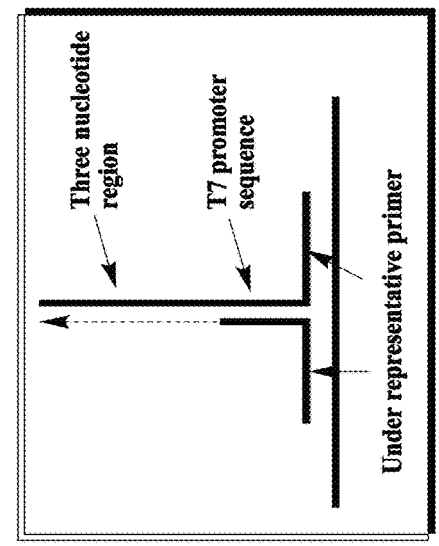
C. Rolling Circle Amplification
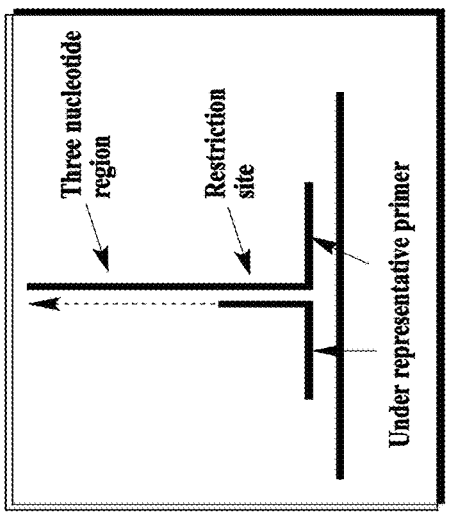

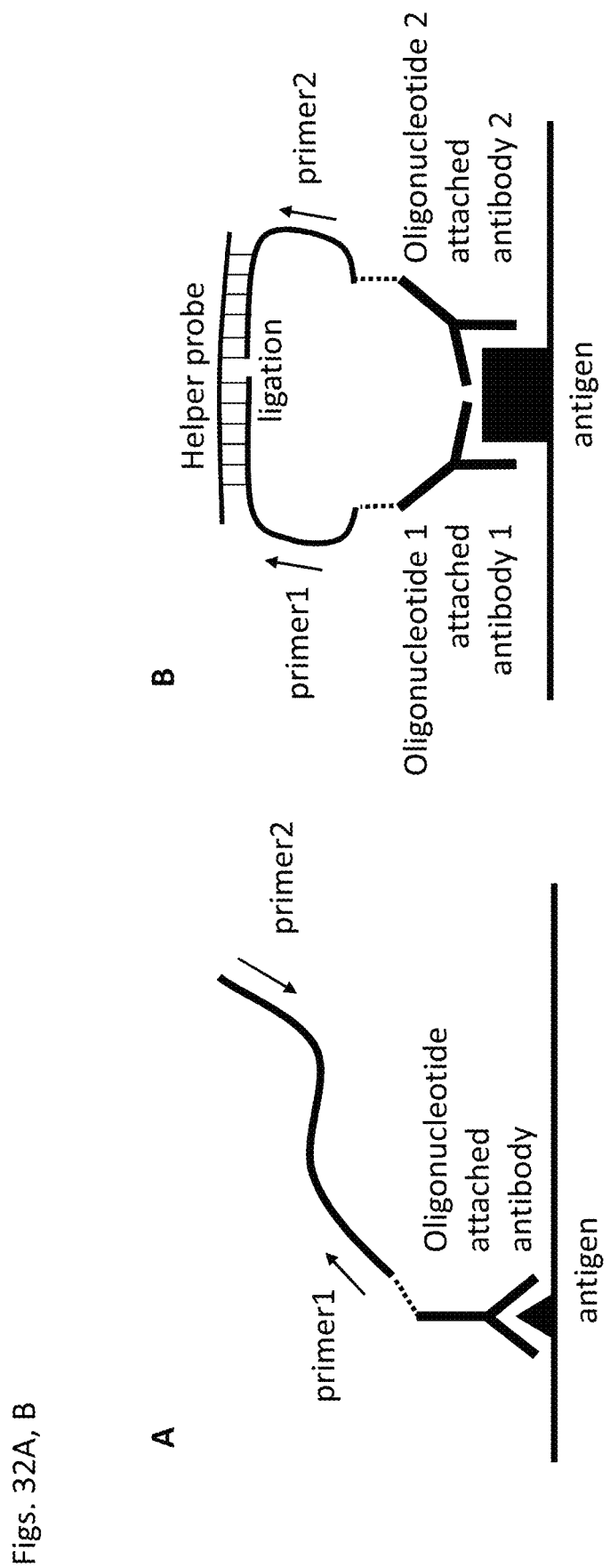
Figs. 32A, B

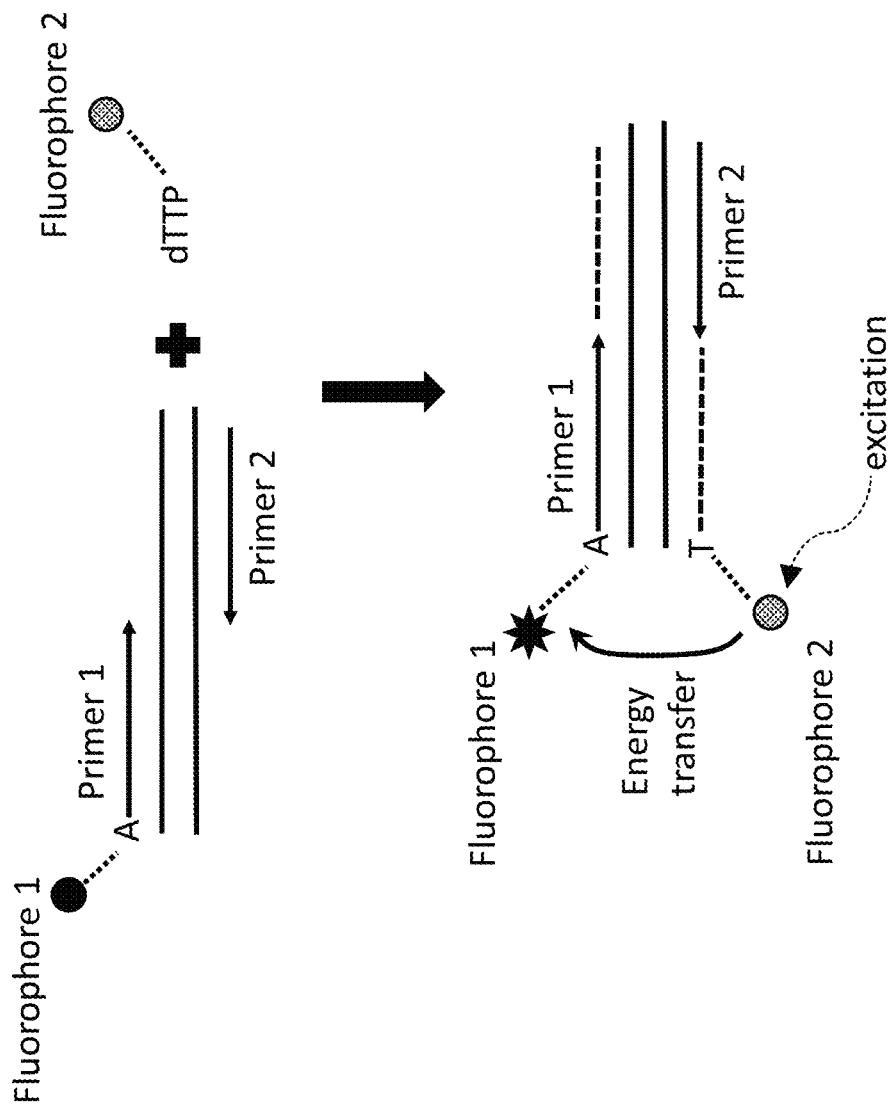
Fig. 33 Use A:T pair as example

Multiplex Amplification and Detection
Double strand tailed underrepresented primer for melt curve analysis Multiplex Amplification and Detection
Signal generation with 5' Flap endonuclease

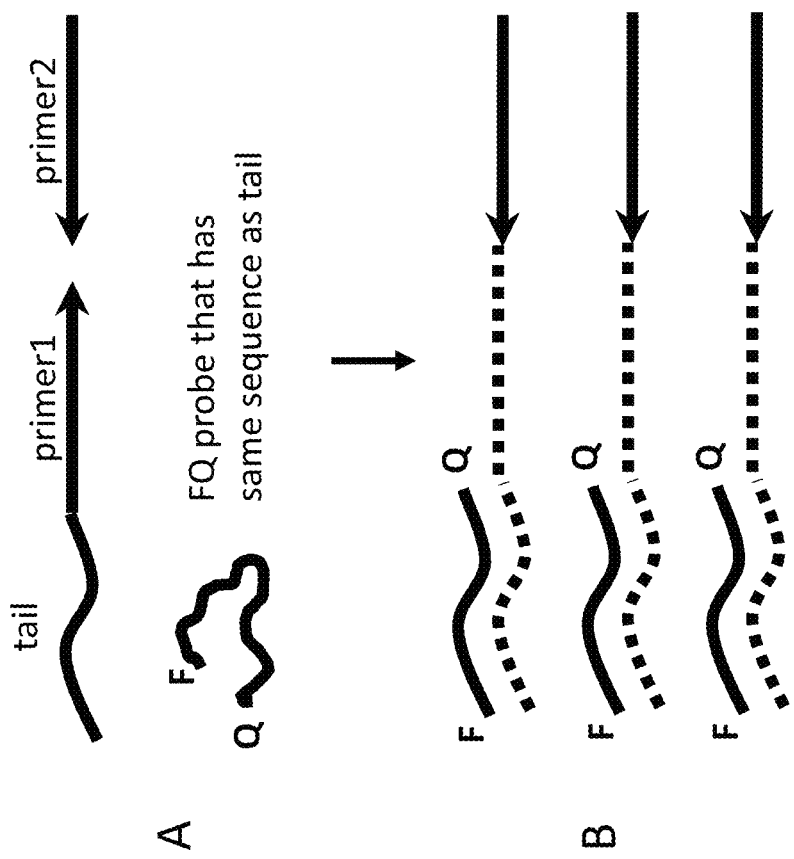

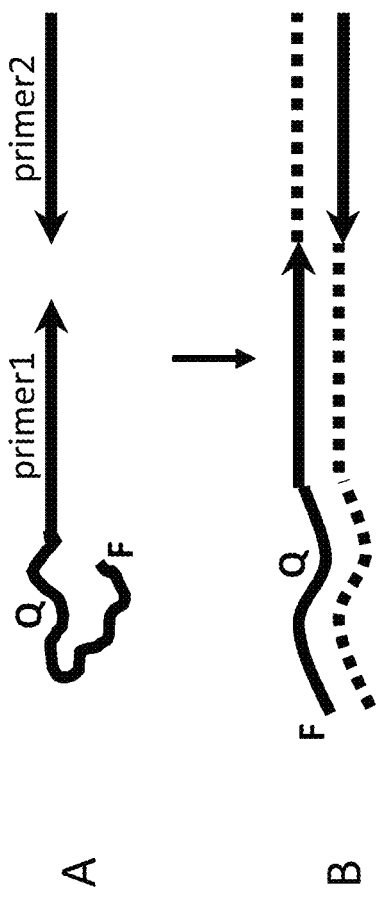
Figs. 40A, B
Multiplex Amplification and Detection

SEQUENCE LISTING

<160> NUMBER OF SEQ ID NOS: 122

<210> SEQ ID NO 1
<211> LENGTH: 48
<212> TYPE: DNA
<213> ORGANISM: Artificial sequence
<220> FEATURE:
<223> OTHER INFORMATION: Synthesized

<400> SEQUENCE: 1
gtccattgca ggtttactgt gcagcattcg agtgctggag cagatgtt             48

<210> SEQ ID NO 2
<211> LENGTH: 51
<212> TYPE: DNA
<213> ORGANISM: Artificial sequence
<220> FEATURE:
<223> OTHER INFORMATION: Synthesized

<400> SEQUENCE: 2
gtgaaggtac aaatgaggag gggcgatatt gtgtcccctg tatgttttc c          51

<210> SEQ ID NO 3
<211> LENGTH: 47
<212> TYPE: DNA
<213> ORGANISM: Artificial sequence
<220> FEATURE:
<223> OTHER INFORMATION: Synthesized

<400> SEQUENCE: 3
gtggtgttac aagtgtgaca acaggttagg accggccaga tggacaa              47

<210> SEQ ID NO 4
<211> LENGTH: 53
<212> TYPE: DNA
<213> ORGANISM: Artificial sequence
<220> FEATURE:
<223> OTHER INFORMATION: Synthesized

<400> SEQUENCE: 4
agttcgttta tgtgtcaaca gtacagcaca ggtagggcac acaatattca ctg        53

<210> SEQ ID NO 5
<211> LENGTH: 45
<212> TYPE: DNA
<213> ORGANISM: Artificial sequence
<220> FEATURE:
<223> OTHER INFORMATION: Synthesized

<400> SEQUENCE: 5 cggtacccccc tcgaagtcgt ttgtccatac caaagcctgc tccgt        45

<210> SEQ ID NO 6
<211> LENGTH: 47
<212> TYPE: DNA
<213> ORGANISM: Artificial sequence
<220> FEATURE:
<223> OTHER INFORMATION: Synthesized

<400> SEQUENCE: 6
acaaccccac caagcgagtg cgacccggtc tttgtttgtg cagtcag        47

<210> SEQ ID NO 7
<211> LENGTH: 45
<212> TYPE: DNA
<213> ORGANISM: Artificial sequence
<220> FEATURE:
<223> OTHER INFORMATION: Synthesized

<400> SEQUENCE: 7
ctaccagctg cagtgtgttg ttacacggga tgaaccacag cgtca        45

<210> SEQ ID NO 8
<211> LENGTH: 46
<212> TYPE: DNA
<213> ORGANISM: Artificial sequence
<220> FEATURE:
<223> OTHER INFORMATION: Synthesized

<400> SEQUENCE: 8
tagaagcctc acgggatact ctgcgggttt gcagttgcac accacg        46

<210> SEQ ID NO 9
<211> LENGTH: 48
<212> TYPE: DNA
<213> ORGANISM: Artificial sequence
<220> FEATURE:
<223> OTHER INFORMATION: Synthesized

<400> SEQUENCE: 9
tcctagtgag tccataaaca gctgctgctg cagctggtag tagaagcc        48

<210> SEQ ID NO 10
<211> LENGTH: 49
<212> TYPE: DNA
<213> ORGANISM: Artificial sequence
<220> FEATURE:
<223> OTHER INFORMATION: Synthesized

<400> SEQUENCE: 10
gtgcaactgc aaaccagtaa cctgctgcct gtactagaaa ccatccgtt        49

<210> SEQ ID NO 11
<211> LENGTH: 44

<212> TYPE: DNA
<213> ORGANISM: Artificial sequence
<220> FEATURE:
<223> OTHER INFORMATION: Synthesized

<400> SEQUENCE: 11
accgtggact tagatccgtc tccacatgca ggaggcagca agga            44

<210> SEQ ID NO 12
<211> LENGTH: 50
<212> TYPE: DNA
<213> ORGANISM: Artificial sequence
<220> FEATURE:
<223> OTHER INFORMATION: Synthesized

<400> SEQUENCE: 12
agtgggcaca aaaaagcaaa acgacgctga gtctctgcag cttccacttc      50

<210> SEQ ID NO 13
<211> LENGTH: 49
<212> TYPE: DNA
<213> ORGANISM: Artificial sequence
<220> FEATURE:
<223> OTHER INFORMATION: Synthesized

<400> SEQUENCE: 13
ctccactgct ttccactgcc agttgcgtgt tacagaattg aagctccgt       49

<210> SEQ ID NO 14
<211> LENGTH: 44
<212> TYPE: DNA
<213> ORGANISM: Artificial sequence
<220> FEATURE:
<223> OTHER INFORMATION: Synthesized

<400> SEQUENCE: 14
ccttcgcgtt gtacagcaga tgttagtcca tcgccgttgc tagt            44

<210> SEQ ID NO 15
<211> LENGTH: 49
<212> TYPE: DNA
<213> ORGANISM: Artificial sequence
<220> FEATURE:
<223> OTHER INFORMATION: Synthesized

<400> SEQUENCE: 15
gccgtaatgt gctatcacaa ctgtgaggcc agatggacaa gcagaacaa       49

<210> SEQ ID NO 16
<211> LENGTH: 46
<212> TYPE: DNA
<213> ORGANISM: Artificial sequence
<220> FEATURE:
<223> OTHER INFORMATION: Synthesized

<400> SEQUENCE: 16
gcattcatag cactgcgacg gaccttctat agccgtgcac agccgg          46

<210> SEQ ID NO 17
<211> LENGTH: 52
<212> TYPE: DNA
<213> ORGANISM: Artificial sequence
<220> FEATURE:
<223> OTHER INFORMATION: Synthesized

<400> SEQUENCE: 17
ggtctacttc atcctcatcc tcatcctata ccacaaactg agattgacct gc        52

<210> SEQ ID NO 18
<211> LENGTH: 45
<212> TYPE: DNA
<213> ORGANISM: Artificial sequence
<220> FEATURE:
<223> OTHER INFORMATION: Synthesized

<400> SEQUENCE: 18
agccacagca agctagacgg gacgagccaa ctgcaccaac gactc                45

<210> SEQ ID NO 19
<211> LENGTH: 46
<212> TYPE: DNA
<213> ORGANISM: Artificial sequence
<220> FEATURE:
<223> OTHER INFORMATION: Synthesized

<400> SEQUENCE: 19
caactgcacc acaaacttac actgacagcg gccacagcaa gctaga               46

<210> SEQ ID NO 20
<211> LENGTH: 47
<212> TYPE: DNA
<213> ORGANISM: Artificial sequence
<220> FEATURE:
<223> OTHER INFORMATION: Synthesized

<400> SEQUENCE: 20
acattcagag taccaaagag gacctgcgcg cagagtgggc acgttac               47

<210> SEQ ID NO 21
<211> LENGTH: 52
<212> TYPE: DNA
<213> ORGANISM: Artificial sequence
<220> FEATURE:
<223> OTHER INFORMATION: Synthesized

<400> SEQUENCE: 21
ccgtccaagc ctatttcatc ctcgtctatt tacatcctga ccaactgac ct          52

<210> SEQ ID NO 22
<211> LENGTH: 51
<212> TYPE: DNA
<213> ORGANISM: Artificial sequence
<220> FEATURE:
<223> OTHER INFORMATION: Synthesized

<400> SEQUENCE: 22
atggacaagc acaaccggcc acagctactg ttgatacaca aacgaaccgt g          51

<210> SEQ ID NO 23
<211> LENGTH: 47
<212> TYPE: DNA
<213> ORGANISM: Artificial sequence
<220> FEATURE:
<223> OTHER INFORMATION: Synthesized

<400> SEQUENCE: 23
atggtgttta ttgctgtgca cagctagaca accgacgtac gaaccct               47

<210> SEQ ID NO 24
<211> LENGTH: 51
<212> TYPE: DNA
<213> ORGANISM: Artificial sequence

```
<220> FEATURE:
<223> OTHER INFORMATION: Synthesized

<400> SEQUENCE: 24
tggatgaccc tgaaggtaca aacgggctcc tgttcttcgt tctattaccg c        51

<210> SEQ ID NO 25
<211> LENGTH: 44
<212> TYPE: DNA
<213> ORGANISM: Artificial sequence
<220> FEATURE:
<223> OTHER INFORMATION: Synthesized

<400> SEQUENCE: 25
accgtggtgc cacaagtgta acgggccaga tggacaagca caac                44

<210> SEQ ID NO 26
<211> LENGTH: 51
<212> TYPE: DNA
<213> ORGANISM: Artificial sequence
<220> FEATURE:
<223> OTHER INFORMATION: Synthesized

<400> SEQUENCE: 26
caacagtaca acaaccgacg tacgaactgt ttattgctgt gcacagctag g         51

<210> SEQ ID NO 27
<211> LENGTH: 45
<212> TYPE: DNA
<213> ORGANISM: Artificial sequence
<220> FEATURE:
<223> OTHER INFORMATION: Synthesized

<400> SEQUENCE: 27
ctcgcgctct gcctgtacac atgcaacaga tacaggttca gactt               45

<210> SEQ ID NO 28
<211> LENGTH: 51
<212> TYPE: DNA
<213> ORGANISM: Artificial sequence
<220> FEATURE:
<223> OTHER INFORMATION: Synthesized

<400> SEQUENCE: 28
gcacaggcct tgtttaatgt gcaggatcta tactgcaccc aaactttcgt t         51

<210> SEQ ID NO 29
<211> LENGTH: 46
<212> TYPE: DNA
<213> ORGANISM: Artificial sequence
<220> FEATURE:
<223> OTHER INFORMATION: Synthesized

<400> SEQUENCE: 29
ccataagcag ctgttgtacc acacgtgtga gttggtggtg cagttg              46

<210> SEQ ID NO 30
<211> LENGTH: 40
<212> TYPE: DNA
<213> ORGANISM: Artificial sequence
<220> FEATURE:
<223> OTHER INFORMATION: Synthesized

<400> SEQUENCE: 30
aacgtgccca ctctgcgcac cacaacatcc catcccctcc                     40
```

<210> SEQ ID NO 31
<211> LENGTH: 50
<212> TYPE: DNA
<213> ORGANISM: Artificial sequence
<220> FEATURE:
<223> OTHER INFORMATION: Synthesized

<400> SEQUENCE: 31
caactgcacc accaactcac acttacaaca gcaagctaga caagctgaac          50

<210> SEQ ID NO 32
<211> LENGTH: 53
<212> TYPE: DNA
<213> ORGANISM: Artificial sequence
<220> FEATURE:
<223> OTHER INFORMATION: Synthesized

<400> SEQUENCE: 32
ccaaagagga gctacgtgtg gtacaaccca ttgcagttat ttagatgatg cgc       53

<210> SEQ ID NO 33
<211> LENGTH: 40
<212> TYPE: DNA
<213> ORGANISM: Artificial sequence
<220> FEATURE:
<223> OTHER INFORMATION: Synthesized

<400> SEQUENCE: 33
aatacctcct cactctcacc caatttctcc cccaacaccc                      40

<210> SEQ ID NO 34
<211> LENGTH: 40
<212> TYPE: DNA
<213> ORGANISM: Artificial sequence
<220> FEATURE:
<223> OTHER INFORMATION: Synthesized

<400> SEQUENCE: 34
acaccacaca taatttcacc tctctatctc ccaccccac                       40

<210> SEQ ID NO 35
<211> LENGTH: 40
<212> TYPE: DNA
<213> ORGANISM: Artificial sequence
<220> FEATURE:
<223> OTHER INFORMATION: Synthesized

<400> SEQUENCE: 35 tccctccct ttactcccat ttcaccttaa ccttcccaac                       40

<210> SEQ ID NO 36
<211> LENGTH: 40
<212> TYPE: DNA
<213> ORGANISM: Artificial sequence
<220> FEATURE:
<223> OTHER INFORMATION: Synthesized

<400> SEQUENCE: 36
ccataaacta ctcccatatc ttcccattcc ccttcctccc                      40

<210> SEQ ID NO 37
<211> LENGTH: 40
<212> TYPE: DNA
<213> ORGANISM: Artificial sequence
<220> FEATURE:
<223> OTHER INFORMATION: Synthesized

```
<400> SEQUENCE: 37
aactaccatc cttctctaca tcctctccaa atctccccccc                               40

<210> SEQ ID NO 38
<211> LENGTH: 40
<212> TYPE: DNA
<213> ORGANISM: Artificial sequence
<220> FEATURE:
<223> OTHER INFORMATION: Synthesized

<400> SEQUENCE: 38
cacaccatac catcccactc ccatttactt tctacccctc                               40

<210> SEQ ID NO 39
<211> LENGTH: 40
<212> TYPE: DNA
<213> ORGANISM: Artificial sequence
<220> FEATURE:
<223> OTHER INFORMATION: Synthesized

<400> SEQUENCE: 39
tcctatcccc ccttccatat caccccctat cccctttcacc                              40

<210> SEQ ID NO 40
<211> LENGTH: 40
<212> TYPE: DNA
<213> ORGANISM: Artificial sequence
<220> FEATURE:
<223> OTHER INFORMATION: Synthesized

<400> SEQUENCE: 40
accactcttc ctcacaacat atccttcctc cacccacacc                               40

<210> SEQ ID NO 41
<211> LENGTH: 40
<212> TYPE: DNA
<213> ORGANISM: Artificial sequence
<220> FEATURE:
<223> OTHER INFORMATION: Synthesized

<400> SEQUENCE: 41 aacccccctac aaaatcccca ccaccaaccc catctacacc                              40

<210> SEQ ID NO 42
<211> LENGTH: 40
<212> TYPE: DNA
<213> ORGANISM: Artificial sequence
<220> FEATURE:
<223> OTHER INFORMATION: Synthesized

<400> SEQUENCE: 42
ccaccaccaa ctataacttc attcctctca cttccctccc                               40

<210> SEQ ID NO 43
<211> LENGTH: 40
<212> TYPE: DNA
<213> ORGANISM: Artificial sequence
<220> FEATURE:
<223> OTHER INFORMATION: Synthesized

<400> SEQUENCE: 43
accccttaaa acccacctac tccatacctc ccctcaaccc                               40

<210> SEQ ID NO 44
```

<211> LENGTH: 40
<212> TYPE: DNA
<213> ORGANISM: Artificial sequence
<220> FEATURE:
<223> OTHER INFORMATION: Synthesized

<400> SEQUENCE: 44
atcccccata cccaatctct atcctatcac accaaccacc                                40

<210> SEQ ID NO 45
<211> LENGTH: 40
<212> TYPE: DNA
<213> ORGANISM: Artificial sequence
<220> FEATURE:
<223> OTHER INFORMATION: Synthesized

<400> SEQUENCE: 45
acacctaatt accctctcca accttactcc ctcattcccc                                40

<210> SEQ ID NO 46
<211> LENGTH: 40
<212> TYPE: DNA
<213> ORGANISM: Artificial sequence
<220> FEATURE:
<223> OTHER INFORMATION: Synthesized

<400> SEQUENCE: 46
cttacacact cttccatcct ccctctaaac cacctctctc                                40

<210> SEQ ID NO 47
<211> LENGTH: 40
<212> TYPE: DNA
<213> ORGANISM: Artificial sequence
<220> FEATURE:
<223> OTHER INFORMATION: Synthesized

<400> SEQUENCE: 47
ccccatttta accctcccc aaacaacacc tacaactccc                                 40

<210> SEQ ID NO 48
<211> LENGTH: 40
<212> TYPE: DNA
<213> ORGANISM: Artificial sequence
<220> FEATURE:
<223> OTHER INFORMATION: Synthesized

<400> SEQUENCE: 48
cccactacat ctttcccttc tactcctacc tactcccatc                                40

<210> SEQ ID NO 49
<211> LENGTH: 40
<212> TYPE: DNA
<213> ORGANISM: Artificial sequence
<220> FEATURE:
<223> OTHER INFORMATION: Synthesized

<400> SEQUENCE: 49
aacctccacc taccattcct cccacaactc acacaccctc                                40

<210> SEQ ID NO 50
<211> LENGTH: 40
<212> TYPE: DNA
<213> ORGANISM: Artificial sequence
<220> FEATURE:
<223> OTHER INFORMATION: Synthesized

<400> SEQUENCE: 50 ctttatacccc caaaccatat cctttacccc ttccctcccc                                40

<210> SEQ ID NO 51
<211> LENGTH: 40
<212> TYPE: DNA
<213> ORGANISM: Artificial sequence
<220> FEATURE:
<223> OTHER INFORMATION: Synthesized

<400> SEQUENCE: 51
ctcctccatt caccttccac ctcttttcaa acccaacacc                                40

<210> SEQ ID NO 52
<211> LENGTH: 40
<212> TYPE: DNA
<213> ORGANISM: Artificial sequence
<220> FEATURE:
<223> OTHER INFORMATION: Synthesized

<400> SEQUENCE: 52
aatccccacc aaaccatcta ctatcattcc ctccatcccc                                40

<210> SEQ ID NO 53
<211> LENGTH: 40
<212> TYPE: DNA
<213> ORGANISM: Artificial sequence
<220> FEATURE:
<223> OTHER INFORMATION: Synthesized

<400> SEQUENCE: 53
aattaaactt cctccaccct tccttccaac caccccacac                                40

<210> SEQ ID NO 54
<211> LENGTH: 40
<212> TYPE: DNA
<213> ORGANISM: Artificial sequence
<220> FEATURE:
<223> OTHER INFORMATION: Synthesized

<400> SEQUENCE: 54
taactcaact aatttcttac cttccacctc cccccctcc                                 40

<210> SEQ ID NO 55
<211> LENGTH: 40
<212> TYPE: DNA
<213> ORGANISM: Artificial sequence
<220> FEATURE:
<223> OTHER INFORMATION: Synthesized

<400> SEQUENCE: 55
tacccctacc cacacccccct caactaaacc atacactaac                               40

<210> SEQ ID NO 56
<211> LENGTH: 40
<212> TYPE: DNA
<213> ORGANISM: Artificial sequence
<220> FEATURE:
<223> OTHER INFORMATION: Synthesized

<400> SEQUENCE: 56
ccctcatttt ctcaaacaca accctctcct cactctcccc                                40

<210> SEQ ID NO 57
<211> LENGTH: 40
<212> TYPE: DNA

<213> ORGANISM: Artificial sequence
<220> FEATURE:
<223> OTHER INFORMATION: Synthesized

<400> SEQUENCE: 57
ctatacccat ccctaaacac atcaactcca ccctcttccc            40

<210> SEQ ID NO 58
<211> LENGTH: 40
<212> TYPE: DNA
<213> ORGANISM: Artificial sequence
<220> FEATURE:
<223> OTHER INFORMATION: Synthesized

<400> SEQUENCE: 58
tcccaatcct atctcacact ccttctccac cccccaacc            40

<210> SEQ ID NO 59
<211> LENGTH: 40
<212> TYPE: DNA
<213> ORGANISM: Artificial sequence
<220> FEATURE:
<223> OTHER INFORMATION: Synthesized

<400> SEQUENCE: 59
tctccctact aactaaccat cctcccctcc aaaccacttc            40

<210> SEQ ID NO 60
<211> LENGTH: 40
<212> TYPE: DNA
<213> ORGANISM: Artificial sequence
<220> FEATURE:
<223> OTHER INFORMATION: Synthesized

<400> SEQUENCE: 60
ctaccccctc tactactact cacaccccc actaacttac            40

<210> SEQ ID NO 61
<211> LENGTH: 40
<212> TYPE: DNA
<213> ORGANISM: Artificial sequence
<220> FEATURE:
<223> OTHER INFORMATION: Synthesized

<400> SEQUENCE: 61
cccatacatc aaactctcat tatcccctcc accccacccc            40

<210> SEQ ID NO 62
<211> LENGTH: 40
<212> TYPE: DNA
<213> ORGANISM: Artificial sequence
<220> FEATURE:
<223> OTHER INFORMATION: Synthesized

<400> SEQUENCE: 62
ttcacccccc aaaccatccc ttccctctca ctccctcctc            40

<210> SEQ ID NO 63
<211> LENGTH: 40
<212> TYPE: DNA
<213> ORGANISM: Artificial sequence
<220> FEATURE:
<223> OTHER INFORMATION: Synthesized

<400> SEQUENCE: 63
atattaacac ccttctccct cacatcccca cttccttccc            40

<210> SEQ ID NO 64
<211> LENGTH: 40
<212> TYPE: DNA
<213> ORGANISM: Artificial sequence
<220> FEATURE:
<223> OTHER INFORMATION: Synthesized

<400> SEQUENCE: 64
acaacaacac ctccccctaa accaaccaac ccctcctaac                               40

<210> SEQ ID NO 65
<211> LENGTH: 46
<212> TYPE: DNA
<213> ORGANISM: Artificial sequence
<220> FEATURE:
<223> OTHER INFORMATION: Synthesized

<400> SEQUENCE: 65
aatttctatt aaaccttcct ttcttcccta actccaacta ctaaac                        46

<210> SEQ ID NO 66
<211> LENGTH: 38
<212> TYPE: DNA
<213> ORGANISM: Artificial sequence
<220> FEATURE:
<223> OTHER INFORMATION: Synthesized

<400> SEQUENCE: 66
cacaatccac atcctcaacc cccttcataa tatccccc                                 38

<210> SEQ ID NO 67
<211> LENGTH: 37
<212> TYPE: DNA
<213> ORGANISM: Artificial sequence
<220> FEATURE:
<223> OTHER INFORMATION: Synthesized

<400> SEQUENCE: 67
cttatcttac ctccacacct aatacccttt cacaatc                                  37

<210> SEQ ID NO 68
<211> LENGTH: 32
<212> TYPE: DNA
<213> ORGANISM: Artificial sequence
<220> FEATURE:
<223> OTHER INFORMATION: Synthesized

<400> SEQUENCE: 68
ccaccatacc caccactatt ttctacatca tc                                       32

<210> SEQ ID NO 69
<211> LENGTH: 34
<212> TYPE: DNA
<213> ORGANISM: Artificial sequence
<220> FEATURE:
<223> OTHER INFORMATION: Synthesized

<400> SEQUENCE: 69
tacaatcaac aacatcctca ctcacaatta caac                                     34

<210> SEQ ID NO 70
<211> LENGTH: 34
<212> TYPE: DNA
<213> ORGANISM: Artificial sequence
<220> FEATURE:

<223> OTHER INFORMATION: Synthesized

<400> SEQUENCE: 70
taaacaacca cacaaacaac catctatcac catc                                34

<210> SEQ ID NO 71
<211> LENGTH: 29
<212> TYPE: DNA
<213> ORGANISM: Artificial sequence
<220> FEATURE:
<223> OTHER INFORMATION: Synthesized

<400> SEQUENCE: 71
cccttcatct tttctttccc cttcttttc                                     29

<210> SEQ ID NO 72
<211> LENGTH: 39
<212> TYPE: DNA
<213> ORGANISM: Artificial sequence
<220> FEATURE:
<223> OTHER INFORMATION: Synthesized

<400> SEQUENCE: 72
ccctcttact tctcccttc ctatcacatc aacttaacc                           39

<210> SEQ ID NO 73
<211> LENGTH: 41
<212> TYPE: DNA
<213> ORGANISM: Artificial sequence
<220> FEATURE:
<223> OTHER INFORMATION: Synthesized

<400> SEQUENCE: 73
ctcttactct accatttccc ttctatttaa cccttctatt c                       41

<210> SEQ ID NO 74
<211> LENGTH: 40
<212> TYPE: DNA
<213> ORGANISM: Artificial sequence
<220> FEATURE:
<223> OTHER INFORMATION: Synthesized

<400> SEQUENCE: 74
ccaaatctcc aaccttcaaa ctttaaaccc aacttcaaac                         40

<210> SEQ ID NO 75
<211> LENGTH: 50
<212> TYPE: DNA
<213> ORGANISM: Artificial sequence
<220> FEATURE:
<223> OTHER INFORMATION: Synthesized

<400> SEQUENCE: 75
ccatcaataa actaccctct cctcaaccac ttacttctcc tctcttattc              50

<210> SEQ ID NO 76
<211> LENGTH: 29
<212> TYPE: DNA
<213> ORGANISM: Artificial sequence
<220> FEATURE:
<223> OTHER INFORMATION: Synthesized

<400> SEQUENCE: 76
ccaccttccc tccctctcc cccacaccc                                      29

<210> SEQ ID NO 77
<211> LENGTH: 38
<212> TYPE: DNA
<213> ORGANISM: Artificial sequence
<220> FEATURE:
<223> OTHER INFORMATION: Synthesized

<400> SEQUENCE: 77
ccctttcctt actttctcat caaatcattc caacaacc         38

<210> SEQ ID NO 78
<211> LENGTH: 32
<212> TYPE: DNA
<213> ORGANISM: Artificial sequence
<220> FEATURE:
<223> OTHER INFORMATION: Synthesized

<400> SEQUENCE: 78
tttctcaatt ccacatacca atttctaatc cc         32

<210> SEQ ID NO 79
<211> LENGTH: 40
<212> TYPE: DNA
<213> ORGANISM: Artificial sequence
<220> FEATURE:
<223> OTHER INFORMATION: Synthesized

<400> SEQUENCE: 79
tctttccatc tcccatcatc ccctctcttc ctccccaccc         40

<210> SEQ ID NO 80
<211> LENGTH: 51
<212> TYPE: DNA
<213> ORGANISM: Artificial sequence
<220> FEATURE:
<223> OTHER INFORMATION: Synthesized

<400> SEQUENCE: 80
tttctaatca atcccccccct ctcccacaaa aaataccaac tcattttttt c         51

<210> SEQ ID NO 81
<211> LENGTH: 34
<212> TYPE: DNA
<213> ORGANISM: Artificial sequence
<220> FEATURE:
<223> OTHER INFORMATION: Synthesized

<400> SEQUENCE: 81
cttattccca aggcctttaa actgttcacc tcac         34

<210> SEQ ID NO 82
<211> LENGTH: 34
<212> TYPE: DNA
<213> ORGANISM: Artificial sequence
<220> FEATURE:
<223> OTHER INFORMATION: Synthesized

<400> SEQUENCE: 82
catatactga agatcacacc caagctttcc atcc         34

<210> SEQ ID NO 83
<211> LENGTH: 20
<212> TYPE: DNA
<213> ORGANISM: Artificial sequence
<220> FEATURE:
<223> OTHER INFORMATION: Synthesized

<400> SEQUENCE: 83
ctccctgtcg tcaactcctc					20

<210> SEQ ID NO 84
<211> LENGTH: 28
<212> TYPE: DNA
<213> ORGANISM: Artificial sequence
<220> FEATURE:
<223> OTHER INFORMATION: Synthesized

<400> SEQUENCE: 84
ccctcccacc ctcaggacta taccaatc					28

<210> SEQ ID NO 85
<211> LENGTH: 40
<212> TYPE: DNA
<213> ORGANISM: Artificial sequence
<220> FEATURE:
<223> OTHER INFORMATION: Synthesized

<400> SEQUENCE: 85
aatacctcct cactctcacc caatttctcc cccaagaccc					40

<210> SEQ ID NO 86
<211> LENGTH: 40
<212> TYPE: DNA
<213> ORGANISM: Artificial sequence
<220> FEATURE:
<223> OTHER INFORMATION: Synthesized

<400> SEQUENCE: 86
acaccacaca taatttcacc tctctatctc ccaccccgac					40

<210> SEQ ID NO 87
<211> LENGTH: 40
<212> TYPE: DNA
<213> ORGANISM: Artificial sequence
<220> FEATURE:
<223> OTHER INFORMATION: Synthesized

<400> SEQUENCE: 87
tcccctccct ttactcccat ttcaccttaa cgttcccaac					40

<210> SEQ ID NO 88
<211> LENGTH: 40
<212> TYPE: DNA
<213> ORGANISM: Artificial sequence
<220> FEATURE:
<223> OTHER INFORMATION: Synthesized

<400> SEQUENCE: 88
ccataaacta ctcccatatc ttcccattcc cgttcctccc					40

<210> SEQ ID NO 89
<211> LENGTH: 40
<212> TYPE: DNA
<213> ORGANISM: Artificial sequence
<220> FEATURE:
<223> OTHER INFORMATION: Synthesized

<400> SEQUENCE: 89
aactaccatc cttctctaca tcctctccaa atctgccccc					40

<210> SEQ ID NO 90
<211> LENGTH: 40

```
<212> TYPE: DNA
<213> ORGANISM: Artificial sequence
<220> FEATURE:
<223> OTHER INFORMATION: Synthesized

<400> SEQUENCE: 90
cacaccatac catcccactc ccatttagtt tctacccctc                              40

<210> SEQ ID NO 91
<211> LENGTH: 40
<212> TYPE: DNA
<213> ORGANISM: Artificial sequence
<220> FEATURE:
<223> OTHER INFORMATION: Synthesized

<400> SEQUENCE: 91
tcctatcccc ccttccatat cacccctat ccccttcagc                               40

<210> SEQ ID NO 92
<211> LENGTH: 40
<212> TYPE: DNA
<213> ORGANISM: Artificial sequence
<220> FEATURE:
<223> OTHER INFORMATION: Synthesized

<400> SEQUENCE: 92
accactcttc ctcacaacat atccttcctc cagccacacc                              40

<210> SEQ ID NO 93
<211> LENGTH: 40
<212> TYPE: DNA
<213> ORGANISM: Artificial sequence
<220> FEATURE:
<223> OTHER INFORMATION: Synthesized

<400> SEQUENCE: 93
aaccccctac aaaatccgca ccaccaaccc catctacacc                              40

<210> SEQ ID NO 94
<211> LENGTH: 40
<212> TYPE: DNA
<213> ORGANISM: Artificial sequence
<220> FEATURE:
<223> OTHER INFORMATION: Synthesized

<400> SEQUENCE: 94
ccaccaccaa ctataacttc attcctgtca cttccctccc                              40

<210> SEQ ID NO 95
<211> LENGTH: 40
<212> TYPE: DNA
<213> ORGANISM: Artificial sequence
<220> FEATURE:
<223> OTHER INFORMATION: Synthesized

<400> SEQUENCE: 95
aatacctcct cactctcacc caatttctcc cccaagaccc                              40

<210> SEQ ID NO 96
<211> LENGTH: 40
<212> TYPE: DNA
<213> ORGANISM: Artificial sequence
<220> FEATURE:
<223> OTHER INFORMATION: Synthesized

<400> SEQUENCE: 96
```
acaccacaca taatttcacc tctctatctc ccagcccgac         40

<210> SEQ ID NO 97
<211> LENGTH: 40
<212> TYPE: DNA
<213> ORGANISM: Artificial sequence
<220> FEATURE:
<223> OTHER INFORMATION: Synthesized

<400> SEQUENCE: 97
tcccctccct ttactcccat ttcaccttaa cgttccgaac         40

<210> SEQ ID NO 98
<211> LENGTH: 40
<212> TYPE: DNA
<213> ORGANISM: Artificial sequence
<220> FEATURE:
<223> OTHER INFORMATION: Synthesized

<400> SEQUENCE: 98
ccataaacta ctcccatatc ttcccattcc cgttcctgcc         40

<210> SEQ ID NO 99
<211> LENGTH: 40
<212> TYPE: DNA
<213> ORGANISM: Artificial sequence
<220> FEATURE:
<223> OTHER INFORMATION: Synthesized

<400> SEQUENCE: 99
aactaccatc cttctctaca tcctctccaa atctggcccc         40

<210> SEQ ID NO 100
<211> LENGTH: 40
<212> TYPE: DNA
<213> ORGANISM: Artificial sequence
<220> FEATURE:
<223> OTHER INFORMATION: Synthesized

<400> SEQUENCE: 100
cacaccatac catcccactc ccatttagtt tctacgcctc         40

<210> SEQ ID NO 101
<211> LENGTH: 40
<212> TYPE: DNA
<213> ORGANISM: Artificial sequence
<220> FEATURE:
<223> OTHER INFORMATION: Synthesized

<400> SEQUENCE: 101
tcctatcccc ccttccatat caccccctat cccctttgagc         40

<210> SEQ ID NO 102
<211> LENGTH: 40
<212> TYPE: DNA
<213> ORGANISM: Artificial sequence
<220> FEATURE:
<223> OTHER INFORMATION: Synthesized

<400> SEQUENCE: 102
accactcttc ctcacaacat atccttcgtc cagccacacc         40

<210> SEQ ID NO 103
<211> LENGTH: 40
<212> TYPE: DNA
<213> ORGANISM: Artificial sequence

```
<220> FEATURE:
<223> OTHER INFORMATION: Synthesized

<400> SEQUENCE: 103 aacccctac aaaatccgca ccaccagccc catctacacc                40

<210> SEQ ID NO 104
<211> LENGTH: 40
<212> TYPE: DNA
<213> ORGANISM: Artificial sequence
<220> FEATURE:
<223> OTHER INFORMATION: Synthesized

<400> SEQUENCE: 104
ccaccaccaa ctataacttc attcctgtca cttgcctccc                40

<210> SEQ ID NO 105
<211> LENGTH: 33
<212> TYPE: DNA
<213> ORGANISM: Artificial sequence
<220> FEATURE:
<223> OTHER INFORMATION: Synthesized

<400> SEQUENCE: 105
ccctttacat ttccaaatcc attcccttt gac                       33

<210> SEQ ID NO 106
<211> LENGTH: 33
<212> TYPE: DNA
<213> ORGANISM: Artificial sequence
<220> FEATURE:
<223> OTHER INFORMATION: Synthesized

<400> SEQUENCE: 106
catctcatag ttcatatact gcattcccat ttc                      33

<210> SEQ ID NO 107
<211> LENGTH: 41
<212> TYPE: DNA
<213> ORGANISM: Artificial sequence
<220> FEATURE:
<223> OTHER INFORMATION: Synthesized

<400> SEQUENCE: 107
attactctct cactaaccac aataccaaaa caaacattcc c             41

<210> SEQ ID NO 108
<211> LENGTH: 40
<212> TYPE: DNA
<213> ORGANISM: Artificial sequence
<220> FEATURE:
<223> OTHER INFORMATION: Synthesized

<400> SEQUENCE: 108
ccaaccctac cctaaatacc ctatattcat atccactaac               40

<210> SEQ ID NO 109
<211> LENGTH: 65
<212> TYPE: DNA
<213> ORGANISM: Artificial sequence
<220> FEATURE:
<223> OTHER INFORMATION: Synthesized

<400> SEQUENCE: 109
accacacacc cacaccacca cccacacccc tttccttact ttctcatcaa atcattccaa    60
``` caacc 65

<210> SEQ ID NO 110
<211> LENGTH: 57
<212> TYPE: DNA
<213> ORGANISM: Artificial sequence
<220> FEATURE:
<223> OTHER INFORMATION: Synthesized

<400> SEQUENCE: 110
cccttcctct cctctccctc tcaactttct caattccaca taccaatttc taatccc 57

<210> SEQ ID NO 111
<211> LENGTH: 51
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: FAM fluorophore

<400> SEQUENCE: 111
acctccaccc tccccctttc cttactttct catcaaatca ttccaacaac c 51

<210> SEQ ID NO 112
<211> LENGTH: 63
<212> TYPE: DNA
<213> ORGANISM: Artificial sequence
<220> FEATURE:
<223> OTHER INFORMATION: Synthesized

<400> SEQUENCE: 112
accacacacc cacaccacca cccacccctt tccttacttt ctcatcaaat cattccaaca 60
acc 63

<210> SEQ ID NO 113
<211> LENGTH: 38
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (1)..(1)
<223> OTHER INFORMATION: FAM fluorophore

<400> SEQUENCE: 113
acctccaccc tccaccacac acccacacca ccacccac 38

<210> SEQ ID NO 114
<211> LENGTH: 13
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (13)..(13)
<223> OTHER INFORMATION: Black hole quencher BHQ

<400> SEQUENCE: 114
ggagggtgga ggt 13

<210> SEQ ID NO 115
<211> LENGTH: 67

<212> TYPE: DNA
<213> ORGANISM: Artificial sequence
<220> FEATURE:
<223> OTHER INFORMATION: Synthesized

<400> SEQUENCE: 115
ctccataccc actatcaatc atatcaccat cctcggattg gtattggagg ttattaataa    60
tggtgga                                                              67

<210> SEQ ID NO 116
<211> LENGTH: 33
<212> TYPE: DNA
<213> ORGANISM: Artificial sequence
<220> FEATURE:
<223> OTHER INFORMATION: Synthesized

<400> SEQUENCE: 116
tccaccatta ttaataacct ccaataccaa tcc                                 33

<210> SEQ ID NO 117
<211> LENGTH: 34
<212> TYPE: DNA
<213> ORGANISM: Artificial sequence
<220> FEATURE:
<223> OTHER INFORMATION: Synthesized

<400> SEQUENCE: 117
ctccataccc actatcaatc atatcaccat cctc                                34

<210> SEQ ID NO 118
<211> LENGTH: 67
<212> TYPE: DNA
<213> ORGANISM: Artificial sequence
<220> FEATURE:
<223> OTHER INFORMATION: Synthesized

<400> SEQUENCE: 118
tccaccatta ttaataacct ccaataccaa tccgaggatg gtgatatgat tgatagtggg    60
tatggag                                                              67

<210> SEQ ID NO 119
<211> LENGTH: 67
<212> TYPE: DNA
<213> ORGANISM: Artificial sequence
<220> FEATURE:
<223> OTHER INFORMATION: Synthesized

<400> SEQUENCE: 119
ctccataccc agtatcaatg atatcagcat cctcggattg gtattgcagg ttattaataa    60
tcgtgga                                                              67

<210> SEQ ID NO 120
<211> LENGTH: 67
<212> TYPE: DNA
<213> ORGANISM: Artificial sequence
<220> FEATURE:
<223> OTHER INFORMATION: Synthesized

<400> SEQUENCE: 120
tccacgatta ttaataacct gcaataccaa tccgaggatg ctgatatcat tgatactggg    60
tatggag                                                              67

<210> SEQ ID NO 121

```
<211> LENGTH: 33
<212> TYPE: DNA
<213> ORGANISM: Artificial sequence
<220> FEATURE:
<223> OTHER INFORMATION: Synthesized

<400> SEQUENCE: 121
cctaaccata acgtccaata attattacca cct                              33

<210> SEQ ID NO 122
<211> LENGTH: 33
<212> TYPE: DNA
<213> ORGANISM: Artificial sequence
<220> FEATURE:
<223> OTHER INFORMATION: Synthesized

<400> SEQUENCE: 122
cctaaccata acgtccaata attattagca cct                              33
```

AMPLIFICATION WITH PRIMERS OF LIMITED NUCLEOTIDE COMPOSITION

CROSS-REFERENCE TO RELATED APPLICATION

The present application is a US national stage of PCT/US2016/029054 filed Apr. 22, 2016, which claims the benefit of U.S. 62/152,756 filed Apr. 24, 2015, incorporated by reference its entirety for all purposes.

REFERENCE TO A SEQUENCE LISTING

This application includes an electronic sequence listing in a file named 506014SEQLST.TXT, created on Mar. 26, 2020 and containing 23,592 bytes, which is hereby incorporated by reference in its entirety for all purposes.

BACKGROUND

PCR amplification was invented by Kary Mullis in 1983 (Mullis, 1987 U.S. Pat. No. 4,683,202; Saiki et al., 1985, Science (New York, N.Y.), 230(4732), 1350-1354), for which he later won the Nobel Prize. Since then, various primer-based template dependent nucleic acid amplification methods have been described including the strand displacement assay (George T. Walker, Little, & Nadeau, 1993, U.S. Pat. No. 5,270,184; George T. Walker, 1995, U.S. Pat. No. 5,455,166; G. T. Walker et al., 1992, Nucleic Acids Research, 20(7), 1691-1696, 1992, Proceedings of the National Academy of Sciences of the United States of America, 89(1), 392-396) and the transcription-based amplification systems, including the methods described in U.S. Pat. Nos. 5,437,990; 5,409,818; and 5,399,491; the transcription amplification system (TSA) (Kwoh et al., 1989, Proceedings of the National Academy of Sciences of the United States of America, 86(4), 1173-1177; Kacian & Fultz, 1995, U.S. Pat. No. 5,480,784; Kacian & Fultz, 1996, U.S. Pat. No. 5,399,491); and self-sustained sequence replication (3SR) (Fahy, Gingeras, Guatelli, Kwoh, & Whitfield, 1992, WO 92/08800; Guatelli et al., 1990, Proceedings of the National Academy of Sciences of the United States of America, 87(5), 1874-1878); ligation chain reaction (sometimes referred to as oligonucleotide ligase amplification OLA) (Laffler, Carrino, & Marshall, 1993, Annales De Biologie Clinique, 51(9), 821-826); cycling probe technology (CPT) (Duck, Alvarado-Urbina, Burdick, & Collier, 1990a, BioTechniques, 9(2), 142-148), rolling circle amplification (RCA) (Fire & Xu, 1995, Proceedings of the National Academy of Sciences, 92(10), 4641-4645; Lizardi, 1998, U.S. Pat. No. 5,854,033), nucleic acid sequence based amplification (NASBA) (Compton, 1991, Nature, 350 (6313), 91-92, Malek, Davey, Henderson, & Sooknanan, 1992), invasive cleavage technology, Helicase dependent amplification (HDA) (Kong, Vincent, & Xu, 2004, US 2004-0058378 A1; Kong, Vincent, & Xu, 2007 US pat. US2007/0254304 A1), Exponential amplification (EXPAR) (Van Ness, Van Ness, & Galas, 2003, Proceedings of the National Academy of Sciences of the United States of America, 100(8), 4504-4509), Hybridization chain reaction (HCR)(R. M. Dirks & Pierce, 2004, Proceedings of the National Academy of Sciences of the United States of America, 101(43), 15275-15278, R. Dirks & Pierce, 2012, U.S. Pat. No. 8,105,778), and catalyzed hairpin assembly (CHA) (Li, Ellington, & Chen, 2011, Nucleic Acids Research, 39(16), e110). All of the above references are incorporated herein by reference. Although the nucleic acid amplification technique has been widely adopted, it is not without drawbacks limiting its accuracy and sensitivity. The intended amplification product usually results from extension from a pair forward and reverse primers binding to their perfectly complementary primer binding sites. But unintended amplification products can arise from the primers duplexing and each serving as a template for extension of the other (primer-dimer) or from primers priming from secondary (unintended) primer binding sites having varying degrees of mismatch by conventional Watson-Crick pairing rules. In consequence, the intended amplification product is synthesized together with various unintended or background products. The presence of these unintended or background products becomes more significant as the initial concentration of the intended target in the sample is decreased or as the number of cycles of PCR increases (see FIGS. 2 and 3 comparing conventional primers with limited composition of primers of the invention) or when more than one pair of primers is used as in multiplex amplification. In consequence, the sensitivity of detection is limited as is the range of cycles over which a linear increase in signal of a desired amplification product can be detected.

Non-specific amplification can be reduced by reducing the formation of primer extension products prior to the start of the reaction. In one method, referred to as a "hot-start" protocol, one or more critical reagents are withheld from the reaction mixture until the temperature is raised sufficiently to provide the necessary hybridization specificity. Manual hot-start methods, in which the reaction tubes are opened after the initial high temperature incubation step and the missing reagents are added, are labor intensive and increase the risk of contamination of the reaction mixture. Alternatively, a heat sensitive material, such as wax, can be used to separate or sequester reaction components, as described in (Bloch, Raymond, & Read, 1995 U.S. Pat. No. 5,411,876), incorporated herein by reference, and (Chou, Russell, Birch, Raymond, & Bloch, 1992, Nucleic Acids Research, 20(7), 1717-1723), incorporated herein by reference. In these methods, a high temperature pre-reaction incubation melts the heat sensitive material, thereby allowing the reagents to mix.

Another method of reducing the formation of primer extension products prior to the start of the reaction relies on the heat-reversible inactivation of the DNA polymerase. Birch, Laird, & Zoccoli, 1997 U.S. Pat. No. 5,677,152; Birch, Laird, & Zoccoli, 1998 U.S. Pat. No. 5,773,258, both incorporated herein by reference, describe DNA polymerases reversibly modified by the covalent attachment of a modifier group. Incubation of the inactivated DNA polymerase at high temperature results in cleavage of the modifier-enzyme bond, thereby reactivating the enzyme.

Non-covalent reversible inhibition of a DNA polymerase by DNA polymerase-specific antibodies is described in Scalice, Sharkey, Christy Jr., Esders, & Daiss, 1994, US Pat. Nos. 5338671, incorporated herein by reference.

Non-specific amplification also can be reduced by enzymatically degrading extension products formed prior to the start of the reaction using the methods describe in Gelfand, Kwok, & Sninsky, 1995, U.S. Pat. No. 5,418,149, which is incorporated herein by reference. The degradation of newly-synthesized extension products is achieved by incorporating into the reaction mixture dUTP and UNG, and incubating the reaction mixture at 45-60° C. prior to carrying out the amplification reaction. Primer extension results in the formation of uracil-containing DNA, which is degraded by UNG under the pre-amplification conditions. A disadvantage of this method is that the degradation of extension product competes with the formation of extension product and the elimination of non-specific primer extension product may be less complete. An advantage of this method is that uracil-containing DNA introduced into the reaction mixture as a contamination from a previous reaction is also degraded and, thus, the method also reduces the problem of contamination of a PCR by the amplified nucleic acid from previous reactions.

Another method of reducing the formation of primer extension products prior to the start of the reaction relies on the use of primers modified at or near the 3' end by the addition of a moiety to an exocyclic amine, as described in Will, 1999, U.S. Pat. No. 6,001,611, incorporated herein by reference.

Despite efforts to reduce non-specific amplification, most methods are focused on reducing false positive products from primer extension at low temperature. Few methods address the problem of false positive products from primer interaction at high temperature after amplification cycle get started, which is described herein as transient interaction from primers during amplification process. This problem increases as more and more primers are multiplexed in amplification reactions to achieve high-throughput results. Transient interaction forms when internal segments of primers hybridize with each other within one primer or between primers. The hybridizations can be consecutive base pairs following Watson-Crick pairing rules, or base pairs mixed with Watson-Crick pairing (perfect match) and non-Watson-Crick pairing (mismatch or mispairing). DNA mismatch formation in solution has been reviewed by Seela & Budow, 2008, *Molecular bioSystems*, 4(3), 232-245. Among eight possible mismatches, GG, GT, and GA pairs are most stable. Although mismatch base pairs are less stable than Watson-Crick pairs and stability is influenced by base context of sequences, the problem is particularly serious as more and more primers are multiplexed in amplification reactions to achieve high-throughput results which results in extreme sequence diversity. In theory, mismatches close to 3' terminal of primers dramatically influence primer extension efficiency. While this is true, Kwok et al., 1990, *Nucleic Acids Research*, 18(4), 999-1005 and Stadhouders et al., 2010, *The Journal of Molecular Diagnostics: JMD*, 12(1), 109-117 showed that 3' end mismatches had from minor to severe effect; however, none eliminated primer extension. When mismatches are located at #2 position of 3' end of primers, only AA GA pairs had a strong detrimental effect on primer extensions. Collectively, DNA duplexes with mismatches form through transient interactions during both pre-amplification and amplification. Dynamic pairing (perfect matches or mismatches) of 3' nucleotides of primers with a template initiate primer extension resulting in unintended amplification products.

SUMMARY

Primer-primer interaction and non-specific amplification have been fundamental problems in all amplification methods. To address this fundamental issue, a novel primer or probe design method has been discovered that can substantially suppress the primer dimer and unwanted side reaction amplification products. The invention provides a method of amplifying a segment of a target nucleic acid comprising: contacting a sample comprising a target nucleic acid with forward and reverse primers; conducting an amplification reaction wherein an amplified segment of the target nucleic acid is formed by extension of the forward and reverse primers with the target nucleic acid serving as a template; wherein the primers are underrepresented in one or more of the four standard nucleotide types, the underrepresented nucleotide type(s) being the same in the primers, and the amplified segment is the predominant amplification product formed from by extension of the forward and/or reverse primers.

The invention further provides a method of amplifying a target nucleic acid comprising contacting a target nucleic acid with primers having a 3' hybridization segment which randomly varies among primers linked to a 5' artificial segment, which is the same in different primers and, wherein the 5' artificial segment consists of only three types of nucleotide except that the 5' nucleotide can be the underrepresented nucleotide; and the 3' segment consists of the same three types of nucleotides except that up to 20% of its units can be the fourth nucleotide type at positions except the 3' end.

The invention further provides a method of amplifying a target nucleic acid comprising contacting a target nucleic with random primers consisting of the four nucleotide types A, T, C and I (Inosine).

The invention further provides a method of extending a segment of a target nucleic acid comprising contacting a sample comprising a target nucleic acid with a primer; conducting an extension reaction wherein an extended segment of the target nucleic acid is formed by extension of the primer; wherein the primer is underrepresented in one or more of the four standard nucleotide types, and the extended segment is the predominant extension product formed from extension of the primer.

In the disclosed invention, the target to be detected can contain a particular region wherein the primer or probe hybridization or binding region contains three types of nucleotides only. In such a situation, the composition of the primer or probe would also have three types of nucleotides only: ATC, ATG, ACG, and TCG. The missing nucleotide is called an underrepresented nucleotide. The underrepresented nucleotide can be one type of nucleotide, or two types of nucleotides or three types of nucleotides in a primer or probe. As an example of composition of the primer or probe has ATC only, the underrepresented nucleotide is G. The primer contains three types of nucleotides with option which the 3' nucleotide is complementary with the underrepresented nucleotide. For instance, for the ATC primer, the 3' end nucleotide is C that is complementary with the underrepresented nucleotide G. This three nucleotide-type primer or probe does not form primer dimer to produce false positive products because the 3' end of the primer or probe is always mismatched and cannot be extended. These kinds of primers or probes are called underrepresented primers or probes. The primer binding site is called an underrepresented binding site. In a template amplification system, suitable reagents are included to extend the underrepresented primer with a target nucleic acid as template. In a signal amplification system, suitable reagents are included to allow an underrepresented probe to hybridize with target to generate detection signal.

In a situation of exponential amplification such as PCR, two primers are needed. One or both primers can be underrepresented primers. In the situation of both forward and reverse primers are underrepresented primers, a target nucleic acid to be detected can have a region contains three segments: the forwarded primer binding segment, reverse primer binding segment, and the segment between two primers binding sites. Both primer binding segments contains the same three nucleotide types. The segment between two primers binding sites contains zero nucleotides or nucleotides that do not have underrepresented nucleotide and complementary nucleotides of underrepresented nucleotide. In such a situation, PCR amplification needs three types of deoxyribonucleotide triphosphates only. These kinds of forward and reverse underrepresented primer do not use each other as template to form primer dimer products. In addition, unwanted amplification products from both forward and reverse underrepresented primer mis-hybridization are terminated because the system does not have fourth nucleotides. Software is designed to search for the region in the target suitable for such amplification.

In another embodiment, the above mentioned amplification system may include dideoxynucleotide triphosphate(s) complementary to the underrepresented nucleotide(s) in primers. Any unwanted extension product from both forward and reverse primers is terminated by incorporation of the dideoxynucleotide.

In another embodiment, in which an underrepresented primer binding segment in the target cannot be found, the underrepresented primer may contains limited number of underrepresented nucleotides, such as one or two or three, no more than 20% of the primer length. Primers contain one or two or three underrepresented nucleotides can dramatically reduce the primer-primer interaction, while increasing primer-template hybridization efficiency. When a limited number of underrepresented nucleotides are included in the primer, the reaction system needs to include a set of all four types of deoxynucleotides triphosphate for amplification.

In another embodiment, when a limited number of underrepresented nucleotides is included in the underrepresented primer, a reduced amount of deoxynucleotide triphosphates complementary to the underrepresented nucleotide(s) may be used in the amplification system. The reduced amount can be 99% to 0.001% relative to the regular amount of deoxynucleotide triphosphates in the amplification system.

In another embodiment, wherein an underrepresented primer binding segment in the target cannot be found, the primers may have limited number of mismatch base pairs to exclude at least one or all underrepresented nucleotides in the underrepresented primers.

In another embodiment, when an underrepresented primer hybridizes to a primer binding segment with a limited number of mismatch base pairs, many approaches can be used to enhance underrepresented primer hybridization efficiency. For instance, a mismatch binding reagent can be included in the amplification system to improve underrepresented primer hybridization efficiency. For instance, primer hybridization efficiency with C—C mismatch can be enhanced by including a silver ion, a rhodium complex, a 2-amino-7-methyl-1,8-naphthyridine derivative, and so forth.

In another embodiment, an underrepresented primer can be used to amplify any segment of target while regular set of all four types of deoxynucleotide triphosphates are included in the amplification system.

In another embodiment, the 5' end of the underrepresented primers are the underrepresented nucleotides to inhibit any produced primer dimer products to be further used as primer to produce concatemer primer dimer.

In another embodiment, the primer consists of a 3' segment with limited nucleotide composition, a 5' segment with regular four types of nucleotide composition, and a linker between two segments with artificial sequences of same limited nucleotide composition as the 3' segment.

In another embodiment, the linker described above can form a hairpin structure.

In another embodiment, the underrepresented primer need a junction probe to co-hybridize with target to form a three way junction structure to facilitate underrepresented primer binding to its binding site.

In another embodiment, the underrepresented primers have artificial sequences tailed on their 5' end.

In another embodiment, when the underrepresented primers have artificial sequences in the 5' segment, the artificial sequences may include sequences that will interact with specific enzymes or form particular chemical recognition structures before or after the synthesis of the complementary strand of the primer. Optionally, the forward or reverse primer is linked to an enzyme recognition segment. For instance, for nicking amplification, the artificial sequences will include restriction enzyme recognition sequences, which can be a nuclease recognition site. For transcription amplification such as TMA (transcription mediated amplification), the artificial sequences will include promoter sequences. The 5' end sequence may form G-quadruplex structure to recognize specific ligand, and so forth. The artificial sequences may also include barcode.

In another embodiment, the underrepresented primer is a degenerate primer mixture. In another embodiment, the underrepresented primer is a random primer mixture. All oligonucleotides in the mixture are underrepresented in the same nucleotide type(s). In some embodiments, the primer has more than 1%, but no more than 20% underrepresented nucleotides. In some embodiments, the degenerate primer or random primer has a 5' tail with an artificial sequence.

In another embodiment, when target sequences are from organisms of a variety of species or genotypes, or a mixture of more than one alleles, a primer with underrepresented nucleotide(s) can contain degenerate bases at certain positions to match different sequence variations and the amplification may include a combination of an underrepresented primer and a degenerate primer. The concentration ratio of the underrepresented primer and the degenerate primer can be varied.

In another embodiment, the underrepresented primer is provided with a helper primer to facilitate target hybridization and amplification. The helper primer binds to the same primer binding site as the underrepresented primer with fewer number of mismatches. The helper primer is provided in low concentration (e.g., 0.01%, 0.1%, 0.5%, 1%, 2%, 5%, 10%, or 50% of the concentration of the underrepresented primer).

In another embodiment, when more than one underrepresented primers or probes are needed. The primers or probes may bind to opposite or the same strands of template. For three ways junction signal amplification, two probes will hybridize to the same stand. For PCR amplification, forward and reverse underrepresented primers will hybridize to opposite stands.

In another embodiment, after the underrepresented primer or probe hybridizes with a target nucleic acid, an extension reaction to amplify the target may be linear amplification or exponential amplification and the amplification condition may be isothermal or temperature cycling.

In another embodiment, when one or more than one primers or probes are used in a reaction system, not all the primers or probes needs to be underrepresented primers. For instance in LAMP amplification, four primers are needed. BIP or FIP or both BIP and FIP can be underrepresented primer. But the other primers are not necessary to be underrepresented primers.

In another embodiment, when one underrepresented probe is needed, such as padlock probe, 3' end segment or 5' end segment or both 3' end segment and 5' end segment of the probe can have the same type of underrepresented nucleotides. The linker between 3'end and 5' end can be any artificial sequences.

In another embodiment, in high multiplex amplification systems, multiple pairs of underrepresented primers are needed. In some embodiments, the multiple pairs of underrepresented primers have one or more than one kind of universal sequence at the 5' end. The 5' end universal sequences can be any artificial sequences. In multiplex amplification, the amplification targets may be from the same gene, or different genes, or from the same sample or different samples.

In another embodiment, the underrepresented primer or probe may have unnatural nucleotides such as inosine, 5' nitroindole, 7-deaza-2'-deoxyadenosine, 7-deaza-2'-deoxyguanosine, IsoC, or isoG. The underrepresented primer or probe may also be PNA, LNA, and so forth. In some embodiments, inclusion of the above unnatural nucleotides in the primer increases its Tm and hybridization efficiency to template.

In another embodiment, the underrepresented primer is attached at its 5' end by an oligonucleotide segment that can form a stem loop structure. The 5' terminal base of the segment is the complement to the underrepresented nucleotide. When two such primers are used in PCR amplification with three types of deoxynucleotide triphosphates included in the amplification system, the amplified product can be ligated to form a circular product with ligase. In another embodiment, when only one primer has the 5'stem loop structure, the amplification product is ligated to form a hairpin structure.

In another embodiment, the underrepresented primer contains an underrepresented nucleotide internally. When the deoxynucleotide triphosphate complementary to the underrepresented nucleotide is not included in the reaction, the extension will stop at the internal underrepresented nucleotide of the primer and the amplification product will contain a designed stick end. The designed stick end may be ligated with any kinds of adapters for downstream application.

In another embodiment, one, two, or three types of dNTPs are provided in the underrepresented primer reaction.

In another embodiment, deoxyinosine triphosphate, and/or 7-deaza-2"-deoxyguanosine 5"-triphosphate, and/or 7-deaza-2"-deoxyadenosine 5"-triphosphate is provided in the amplification reaction.

In another embodiment, four types of dNTPs are provided, but one, two, or three types of dNTPs are at different concentrations for underrepresented primer extension reaction.

In another embodiment, one, two, or three types of nucleotide triphosphate monomers are provided in the underrepresented primer extension reaction.

In another embodiment, unnatural nucleotide triphosphate monomers are provided in the underrepresented primer extension reaction.

In another embodiment, when more than one underrepresented primers are used, primers may be provided in different concentrations in reactions. For instance, one primer in higher concentration will carry out asymmetric amplification.

In another embodiment, the underrepresented primers or probes may be coated or attached to a surface such as beads or glass surfaces. For amplification reaction, either forward primer or reverse primer or both forward and reverse primer may be attached to a surface.

In another embodiment, for multiplex amplification with multiple pairs of underrepresented primers, the amplification products may be detected with microarray, sequencing, beads, or as nanoparticles. One of a pair underrepresented primers is grafted to a surface in conjunction with free primers in solution. These methods allow the simultaneous amplification and attachment of a PCR product onto the surface. Optionally both primers may be grafted to a surface for amplification. The pattern of how underrepresented primers or probes attach to a surface may be coded or non-coded, or randomly distributed.

In another embodiment, amplification is detected with fluorescent intercalating dyes, fluorescent probes, detection label tags, mass tags, electrophoresis, magnetic tags, or melting curve analysis.

In another embodiment, one underrepresented primer is linked at its 5' end to an artificial oligonucleotide whose melting temperature is different from an amplification product primed from that primer. The amplification reaction is monitored based on a transition from the melting peak of the artificial oligonucleotide to that of the amplification product. Such a format can be multiplex by linking different primers to different artificial oligonucleotides having different melting temperatures. In another embodiment, underrepresented primers are attached on their 5' end by artificial sequences which can form a stem-loop structure with a melting temperature different from the melting temperatures of amplicons. In some embodiments, melting curve analysis is measured from presence of a double-stranded intercalating dye. In another embodiment, a fluorophore and a quencher are attached to the 5' end artificial sequences. In another embodiment, the fluorophore and the quencher are attached to the complementary sequence of the 5' end artificial sequences. In another embodiment, the fluorophore and the quencher are attached to the 5' end artificial sequence and the complementary sequences of the 5' end artificial sequences separately. In another embodiment, the 5' end artificial sequences of the underrepresented primer can form a stem-loop structure.

In some embodiments, in a multiplex reaction, underrepresented primers are attached at their 5' ends to more than one types of artificial sequence. One or more than one type of complementary sequences of the 5' end artificial sequences are included in the reaction. In some embodiments, different complementary sequences of the 5'end artificial sequences are attached with different fluorophore and quencher. In another embodiment, multiple 5' end artificial sequences on the underrepresented primers can form double strands with a common complementary sequences of the 5'end artificial sequences. But the 5' end artificial sequences are different by only one or more than one mutations. The disappearance of a melt peak indicates its corresponding target is present.

In another embodiment, an oligonucleotide labeled with a fluorophore and a quencher is provided in the template amplification reaction. The oligonucleotide is complementary to a segment on the amplicon. During melt curve analysis after amplification reaction, the oligonucleotide dissociate from bound amplicon and a melt peak at its Tm indicates the presence of template. In some embodiments, multiple oligonucleotides with different Tm are provided in the reaction. In some embodiments, the segment on amplicon that hybridizes with the oligonucleotide contains mutations to alter the Tm. In some embodiments, multiple oligonucleotides labeled with different fluorophores are included in the reaction, melt curve analysis is done in multiple channels to increase multiplicity.

In another embodiment, one underrepresented primer is attached on its 5' end by a fluorophore labeled artificial sequence. An oligonucleotide labeled with a quencher is also provided in the reaction. The quencher oligonucleotide hybridizes with the underrepresented primer and the fluorescence is quenched. On template amplification, the underrepresented primer participates in primer extension and becomes a double-stranded amplicon. The quencher oligonucleotide dissociates from the primer and fluorescence is released.

In another embodiment, one underrepresented primer is linked on its 5' end to an artificial sequence that has an underrepresented nucleotide on its 3' end. An oligonucleotide labeled with a fluorophore and a quencher is also provided in the reaction. The oligonucleotide hybridizes with the artificial sequence on primer and the hybridization region covers the underrepresented nucleotide. During amplification, 5' nuclease activity of DNA polymerase digests the oligonucleotide separating the fluorophore and quencher and releases fluorescence. Extensions terminate at the underrepresented nucleotide and the digested oligonucleotide dissociates from its binding region allowing another intact oligonucleotide to hybridize. The process repeats and signal is amplified.

In another embodiment, for multiplex amplification with multiple pairs of underrepresented primers, a universal tail with artificial sequence is attached to the 5' end of underrepresented primers. A universal detection probe is also provided in the reaction, which consists of double-stranded DNA with a 3' overhang segment. The universal probe is labeled with a fluorophore on one strand and a quencher on the other strand so that in double-stranded form the probe is non-fluorescent. The 3' overhang segment contains the same sequence as the universal tail on underrepresented primers. The synthesized sequence complementary to the universal tail hybridizes with the 3' overhang segment of the universal probe and extension results in separation of the double strands of the universal probe and releasing of fluorescence. In some embodiments, more than one types of the universal tail and universal probe are provided in reaction for multiplex detection. In some embodiments, the universal probe is a molecular beacon with 3' overhang. In another embodiment, a fluorophore is attached to the underrepresented primers and double strand intercalating quencher chemical is provided in the reaction. During exponential amplification, the liquid quencher intercalates to the amplified double strands products to quench fluorescent tag for real time detection. The liquid quencher is a non-fluorescent chemical that interacts with double strands DNA and quenches proximity fluorescent tag.

In another embodiment, a fluorophore is attached to the underrepresented primers which generates enhanced fluorescence when the attached primer extends to form a double strand (light-up probe).

In another embodiment, a fluorophore is attached to the underrepresented primers and one type of dNTP is labeled with a different fluorophore. Real time fluorescence is detected by FRET. In some embodiments, fluorophore labeled ddNTP is provided.

In another embodiment, an oligonucleotide template can be attached to an analyte. For instance, the analyte may be a protein or an antibody. Amplification of oligonucleotide template with underrepresented primers indicate the presence of the analyte. In some embodiments, underrepresented primers or probes are attached to an analyte. Amplification with the underrepresented primers or probes indicates the presence or absence of the analyte.

In another embodiment, the current invention is used for mutation detection. Such mutations include nucleotide insertions, deletions, rearrangements, transitions, transversions, polymorphisms, and substitutions.

In another embodiment, the current invention provides a kit for use in sequencing, re-sequencing, gene expression monitoring, genetic diversity profiling, diagnosis, screening, whole genome sequencing, whole genome polymorphism discovery and scoring, transcriptome analysis, or any other applications involving the amplification or detection of nucleic acids or the sequencing. This kit can comprise any of the underrepresented primers or primer pairs or probes described herein and necessary reagents for specific applications.

In another embodiment, the invention provides an apparatus for carrying out the methods of the invention. Such apparatus can perform for example a sample process, underrepresented primers or probes mixing, reagent mixing, amplification and signal detection.

BRIEF DESCRIPTION OF THE DRAWINGS

FIG. 1 shows a target nucleic acid and exemplary three nucleotide primers and primer binding sites. The upper portion of the figure shows one strand of the target nucleic acid containing the complement of the forward primer binding site (ATC nucleotides) contiguous with the reverse primer binding site (ATG site). The lower portion shows the primers bound to their respective binding sites on opposing strands. Amplification can proceed in the presence of dTTP, dATP, and dGTP (and other typical PCR components) but dCTP is not required because there are no G nucleotides in the strands of the target nucleic acid being amplified. Sequences in the lower portion of FIG. 1 are, from top to bottom, SEQ ID NO:115, SEQ ID NO:116 (depicted 3' to 5'), SEQ ID NO:117, and SEQ ID NO:118 (depicted 3' to 5').

FIGS. 2A, B compare transient primer interaction of conventional four-nucleotide-type primers (A) and three-nucleotide primers (B).

FIGS. 3A, B compare amplification product from primer dimer amplification of three nucleotide primers (A) with conventional four-nucleotide-type primers (B).

FIGS. 4A-B shows real time PCR of human genomic DNA (A) with three nucleotide-type primers and three dNTPs compared with a no template control (B).

FIG. 6 shows examples of mismatch binding reagents. Sequences in FIG. 6 are, from top to bottom, SEQ ID NO:116 (depicted 3' to 5'), SEQ ID NO:119, SEQ ID NO:120 (depicted 3' to 5'), and SEQ ID NO:117.

FIGS. 8A-C show fluorescence over time (A, B) and gel electrophoresis (C) from amplification with three nucleotide-type primers and all four dNTPs.

FIG. 9 compares primer dimer between three nucleotide primers and four nucleotide primers.

FIGS. 10A-D shows PCR with primers containing 1 or 2 units of the underrepresented nucleotide (G). The sequence on the left side is SEQ ID NO:121, and the sequence on the right side is SEQ ID NO:122.

FIGS. 11A-C show amplification with mononucleotide triphosphate which is the complement of underrepresented nucleotide present at reduced amount compared with other nucleotide triphosphates types (A), absent (B) and in the absence of template (C).

FIG. 12 shows amplification with the mononucleotide triphosphate which is the complement of the underrepresented nucleotide in the primers supplied as a ddNTP.

FIGS. 13A, B show multiplex detection of multiple templates with melting curve analysis.

FIG. 16A shows a template to be amplified. In FIG. 16B, the four-nucleotide-type 5' region (sequence 4) of the 3 way junction helper hybridizes to template. In FIG. 16C, forward primer extension product hybridizes to reverse primer and generates full length products.

FIG. 30 Use of three nucleotide-type primers for LAMP amplification or Recombinase Polymerase Amplification.

FIGS. 31A, B, C: Isothermal amplification by nicking mechanism, transcription mediated amplification or rolling circle amplification.

FIGS. 32A and B show immunoPCR in which a target nucleic acid is attached to an analyte via one or more antibodies.

FIG. 33 shows an amplification reaction in which a primer is labelled with a first fluorophore and a nucleotide triphosphate used in amplification is labelled with a second fluorophore. Energy transfer between the fluorophores in the amplification product generates a signal.

FIG. 38A shows the primer and a complementary oligonucleotide labelled with a fluorophore and quencher. FIG. 38B shows extension. FIG. 38C shows cleavage of the fluorophore from its oligonucleotide by 5' Flap endonuclease activity generating a fluorescent signal. FIGS. 38D and E show extension and cleavage of another template.

FIGS. 39A, B show a method of monitoring an amplification reaction in which one of the primers is linked to an artificial oligonucleotide tail in an amplification reaction including an oligonucleotide complementary to the tail labeled with a fluorophore and quencher. Before amplification (A), the quencher and fluorophore and quencher are in proximity and the signal is low. After amplification (B), the labeled oligonucleotide hybridizes with the complementary primer tail separating the quencher and fluorophore and increasing the signal.

FIGS. 40A, B show a method of monitoring an amplification reaction in which one of the primers is linked to an artificial oligonucleotide tail including a quencher and fluorophore. Before amplification (A), the quencher and fluorophore are proximate in space so the signal is low. After amplification (B), the fluorophore and quencher are further separated by duplexing of the artificial oligonucleotide to a complementary strand and the fluorescent signal is increased.

DEFINITIONS

Figure 5:
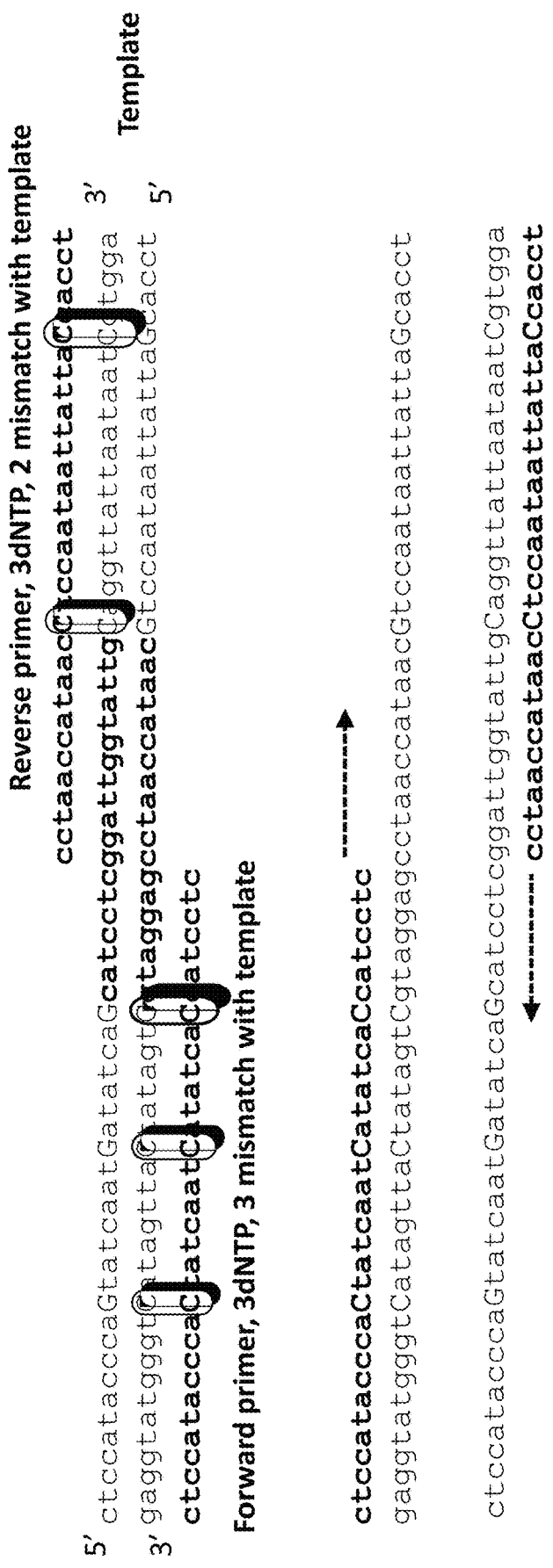
FIG. 5 shows a template in which primer binding sites show three mismatches (forward primer) or two mismatches (reverse primer) to primers of three nucleotide-type composition. Sequences in FIG. 5 are, from top to bottom, SEQ ID NO:116 (depicted 3' to 5'), SEQ ID NO:119, SEQ ID NO:120 (depicted 3' to 5'), SEQ ID NO:117, SEQ ID NO:117, SEQ ID NO:120 (depicted 3' to 5'), SEQ ID NO:119, and SEQ ID NO:116 (depicted 3' to 5').

Unless defined otherwise, all technical and scientific terms used herein have the same meaning as commonly understood in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting. The term "a" or "an" entity refers to one or more of that entity; for example, "a nucleic acid," represents one or more nucleic acids. Therefore, the terms "a" (or "an"), "one or more," and "at least one" can be used interchangeably herein.

Nucleic acids include DNA and RNA and DNA-RNA chimeras can be double-stranded or single-stranded. DNA can be genomic, cDNA, or synthetic. RNA can be mRNA, tRNA, rRNA, hnRNA among others. The term "nucleic acid" encompasses any physical string of monomer units that can be corresponded to a string of nucleotides, including a polymer of nucleotides (e.g., a typical DNA or RNA polymer), peptide nucleic acid (PNA), modified oligonucleotides (e.g., oligonucleotides comprising bases that are not typical to biological RNA or DNA in solution, such as 2'-O-methylated oligonucleotides), and the like. A nucleic acid can be e.g., single-stranded or double-stranded.

The four conventional nucleotide bases are A, T/U, C and G with T being present in DNA and U in RNA. The nucleotides found in targets are usually natural nucleotides (deoxyribonucleotides or ribonucleotides). Such is also the case is nucleotides forming primers.

Complementarity of nucleic acid strands means that the strands form a stabile duplex due to hydrogen bonding between their nucleobase groups. The complementary bases are in DNA, A with T and C with G, and, in RNA, C with G, and U with A. Nucleotides in respective strands are complementarity when they form one of these (Watson-Crick pairings) when the strands are maximally aligned. Nucleotides are mismatched when they do not form a complementarity pair when their respective strands are maximally aligned. Complementarity of strands can be perfect or substantial. Perfect complementarity between two strands means that the two strands can form a duplex in which every base in the duplex is bonded to a complementary base by Watson-Crick pairing. Substantial complementary means most but not necessarily all bases in strands form Watson-Crick pairs to form a stable hybrid complex in set of hybridization conditions (e.g., salt concentration and temperature). For example, some primers can duplex with a primer binding site notwithstanding up to 1, 2 or 3 positions of mismatch, provided such mismatches are not at the 3' end and preferably not proximate thereto (e.g., within 4 nucleotides). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C)−675/N−% mismatch, where N=total number of bases.

A mismatch means that a nucleotide in one strand of nucleic acid does not or cannot pair through Watson-Crick base pairing with a nucleotide in an opposing complementary nucleic acid strand. Examples of mismatches are but not limited to AA, AG, AC, GG, CC, TT, TG, TC, UU, UG, UC, and UT base pairs. Mismatches can happen between DNA and DNA molecules, DNA and RNA molecules, RNA and RNA molecules, and among other natural or artificial nucleic acid analogs.

Mismatch binding reagents or agents are any molecules or any modification in underrepresented primers that can stabilize the underrepresented primer hybridization with underrepresented primer binding sites through chemical interaction or physical interaction. Modification of underrepresented primers may be modified in any way, as long as a given modification is compatible with the desired function of a given underrepresented primers as can be easily determined. Modifications include base modifications, sugar modifications or backbone modifications, Some small molecules can bind to mismatched bases through hydrogen bonds presumably complementary to those in the unpaired base and stabilize the duplex with a high base selectivity. Metal ions have been shown to interact with nucleic acids for their structure formation and folding. Ono A., Togashi H. (Ono & Togashi, 2004, *Angewandte Chemie* (International Ed. in English), 43(33), 4300-4302) showed that addition of mercury ion in solution increases the Tm DNA duplex with T-T mismatch by 5° C. Torigoe H., Okamoto I. et al. (Torigoe et al., 2012, *Biochimie*, 94(11), 2431-2440) showed that silver ion selectively bind and stabilize C—C mismatch. A series of rhodium complexes capable of high-selectivity mismatch site recognition has been designed and synthesized by Cordier C., Pierre V. C. et al. (Cordier, Pierre, & Barton, 2007, *Journal of the American Chemical Society*, 129(40), 12287-12295). Nakatani K., Sando S., et al. (Nakatani, Sando, Kumasawa, Kikuchi, & Saito, 2001, *Journal of the American Chemical Society*, 123(50), 12650-12657) have developed a series of naphthyridine based small molecules to selectively recognize mismatched DNA.

Hybridization or annealing conditions include chemical components and their concentrations (e.g., salts, chelating agents, formamide) of an aqueous or organic solution containing the nucleic acids, and the temperature of the mixture in which one nucleic acid strand bonds to a second nucleic acid strand by complementary strand interactions to produce a hybridization complex.

A sample is a composition in which one or more target nucleic acids of interest may be present, including patient samples, plant or animal materials, waste materials, materials for forensic analysis, environmental samples, Circulation tumor cell (CTC), cell free DNA, liquid biopsy, and the like. Samples include any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a disease or condition, particularly infection by a virus. Other samples of interest include industrial samples, such as for water testing, food testing, contamination control, and the like. Sample components may include target and non-target nucleic acids, and other materials such as salts, acids, bases, detergents, proteins, carbohydrates, lipids and other organic or inorganic materials. A sample may or may not be subject of processing to purify a target nucleic acid before amplification. Further processing can treatment with a detergent or denaturant to release nucleic acids from cells or viruses, removal or inactivation of non-nucleic acid components and concentration of nucleic acids.

A target nucleic acid refers to a nucleic acid molecule or population of related nucleic acid molecules that is or may be present within a sample. A target nucleic acid includes a segment to be amplified defined by primer binding sites. The segment can be the entire nucleic acid or any segment thereof of length amenable to amplification. For example, a target nucleic acid can be an entire chromosome, gene or cDNA, and a target segment can be for example, only 40-500 of these nucleotides. A target segment can present on any strand (sense or anti-sense) of the structure. A target nucleic acid can be RNA (e.g., viral RNA, micro RNA, mRNA, cRNA, rRNA, hnRNA or DNA (genomic or cDNA) among others.

The target nucleic acid can be from a pathogenic microorganism, such as a virus, bacteria or fungus, or can be endogenous to a patient. Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus. Examples of such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, Lymes disease bacteria, streptococci, or neisseria. rRNA is a particularly useful target nucleic acid for typing bacteria. Detection of human or animal genes is useful for detecting presence or susceptibility to disease. Examples of genes that can be the subject of detection include cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses.

An underrepresented nucleotide type is one present in no more than 20% of positions in a primer or primer binding site, or both primer and primer binding site. Typically a primer has nucleotide composition of, A, G, C, T or, A, G, C, U. A primer may include unnatural nucleotide, such as Iso C and IsoG, deaza G or deaza A. These are scored the same way as corresponding standard nucleotides in determining the number or percentage of underrepresented nucleotides. An analog corresponds with a natural nucleotide if it has the same relative pairing affinity with other natural nucleotides. Thus deaza G or inosine are analogs of G because they pair more strongly with C than any of the other natural nucleotides. As an example, if G is an underrepresented nucleotide type, to determine a percentage of the underrepresented nucleotide type in a primer, deaza G is included in the numerator (as well as the denominator) and deaza A only in the denominator. Thus, the percentage of underrepresented nucleotide in a primer containing one G, one deaza G and 20 nucleotides total is 10%. Typically an underrepresented nucleotide type is present in 0, 1 or 2 units at internal positions and optionally one at the 5' terminal position in each primer and 0, 1, 2, 3 or 4 units in each primer binding sites, and in 0 units in an artificial sequence. Ideally one and only unit of the underrepresented nucleotide type is at the 5' terminal position. If one and only one of the four-nucleotide-types is underrepresented it is the least represented (including null representation) of the four standard nucleotide types. If the primer contains a degenerate position, the position is counted as being an underrepresented nucleotide type position (i.e., in the numerator as well as the denominator) if the degeneracy includes the underrepresented nucleotide type and in the denominator only otherwise. A nucleotide analog having no preference among binding to the natural nucleotide types is treated the same as a degenerate position. A primer containing underrepresented nucleotide type(s) is called an underrepresented primer. A probe containing underrepresented nucleotide type(s) called underrepresented probe.

The term "dNTP" generally refers to an individual or combination of deoxynucleotides containing a phosphate, sugar and organic base in the triphosphate form, that provide precursors required by a DNA polymerase for DNA synthesis. A dNTP mixture may include each of the naturally occurring deoxynucleotides (i.e., adenine (A), guanine (G), cytosine (C), uracil (U), and Thymine (T)). In some embodiments, each of the naturally occurring deoxynucleotides may be replaced or supplemented with a synthetic analog; such as inosine, isoG, IsoC, deaza G, deaza A, and so forth. When nucleotides are underrepresented in a primer or a probe, the nucleotides are called underrepresented nucleotides. The underrepresented nucleotides can be included in a reaction system as the form of deoxynucleotides or dideoxynucleotides or ribonucleotides. Their complements are called complementary nucleotides of underrepresented nucleotides. The term "ddNTP" generally refers to an individual or combination of dideoxynucleotides containing a phosphate, sugar and organic base in the triphosphate form, that provide precursors required by a DNA polymerase for DNA synthesis. A ddNTP mixture may include each of the naturally occurring dideoxynucleotides (i.e., adenine (A), guanine (G), cytosine (C), uracil (U), and Thymine (T)). In some embodiments, each of the naturally occurring dideoxynucleotides may be replaced or supplemented with a synthetic analog; such as inosine, isoG, IsoC, deazaG, deaza A, and so forth. The term "NTP" generally refers to an individual or combination of Ribonucleotides containing a phosphate, sugar and organic base in the triphosphate form, that provide precursors required by a RNA polymerase for RNA synthesis. A NTP mixture may include each of the naturally occurring Ribonucleotides (i.e., adenine (A), guanine (G), cytosine (C), uracil (U)). In some embodiments, each of the naturally occurring Ribonucleotides may be replaced or supplemented with a synthetic analog; such as inosine, isoG, IsoC, deazaG, deaza A, and so forth.

A primer binding site or probe binding site is interchangeable with underrepresented primer binding site or underrepresented probe binding site in this invention. A primer binding site is a complete or partial site in a target nucleic acid to which a primer hybridizes. A partial site can be supplemented by provision of toehold and junction sequences, which also contain partial primer binding sites. A partial binding site from a toehold or junction sequence can combine with a partial primer binding site on a target nucleic acid to form a complete primer binding site.

The term primer or probe is interchangeable with underrepresented primer or underrepresented probe in this invention. A primer or a probe is an oligonucleotide complementary to primer or probe binding site contributed in whole or part by a target nucleic acid. A primer or a probe can be linked at its 5' end to another nucleic acid (sometimes referred to as a tail), not found in or complementary to the target nucleic acid. A 5' tail can have an artificial sequence. For a primer or probe exactly complementary to a primer or a probe binding site, the demarcation between primer or probe and tail is readily apparent in that the tail starts with the first noncomplementary nucleotide encountered moving from the 3' end of the primer or probe. For a primer substantially complementary to a primer binding site, the last nucleotide of the primer is the last nucleotide complementary to the primer binding site encountered moving away from the 3' end of the primer that contributes to primer binding to the target nucleic acid (i.e., primer with this 5' nucleotide has higher TM for the target nucleic acid than a primer without the 5' nucleotide). Complementarity or not between nucleotides in the primer and priming binding site is determined by Watson-Crick pairing or not on maximum alignment of the respective sequences.

A primer or a probe is an oligonucleotide. The term "oligonucleotide" encompasses a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof and/or DNA RNA chimeric. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, it may contain detection reagents for signal generation/amplification, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction. Oligonucleotides of a defined sequence and chemical structure may be produced by conventional techniques, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chrarnosarnal DNA or the in vivo transcription products thereof. Oligonucleotides may be modified in any way, as long as a given modification is compatible with the desired function of a given oligonucleotide as can be easily determined. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-ME) substitution to the ribofuranosyl moiety. See "Method for Amplifying Target Nucleic Adds Using Modified Primers," (Becker, Majlessi, & Brentano, 2000, U.S. Pat. No. 6,130,038). Other sugar modifications include, but are not limited to 2'-amino, 2'-fluoro, alpha-threofuranosyl, and pentopuranosyl modifications. The nucleoside subunits may be joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," (Nielsen, Buchardt, Egholm, & Berg, 1996, U.S. Pat. No. 5,539,082). Other linkage modifications include, but are not limited to, morpholine bonds, Non-limiting examples of oligonucleotides or oligomers contemplated by the present invention include nucleic acid analogs containing bicyclic and tricyclic nucleoside and nucleotide analogs (LNAs). See Imanishi et al., "Bicyclonucleoside and Oligonucleotide Analogues," (Imanishi & Obika, 2001, U.S. Pat. No. 6,268,490); and Wengel et al., "Oligonucleotide Analogues," (Wengel & Nielsen, 2003, U.S. Pat. No. 6,670,461). Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions. The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

The term "degenerate primer" refers to a mixture of similar primers with differing bases at the varying positions (Mitsuhashi, J. Clin. Lab. Anal., 10(5): 285 93 (1996); von Eggeling et al., Cell. Mol. Biol., 41(5):653 70 (1995); (Zhang et al., Proc. Natl. Acad. Sci. USA, 89:5847 5851 (1992); Telenius et al., Genomics, 13(3):718 25 (1992)). Such primers can include inosine, as inosine is able to base pair with adenosine, cytosine, guanine or thymidine. Degenerate primers allow annealing to and amplification of a variety of target sequences that can be related. Degenerate primers that anneal to target DNA can function as a priming site for further amplification. A degenerate region is a region of a primer that varies, while the rest of the primer can remain the same. Degenerate primers (or regions) denote more than one primer and can be random. A random primer (or regions) denotes that the sequence is not selected, and it can be degenerate but does not have to be. In some embodiments, the 3' target specific regions have a Tm of between about 5° C. and 50° C. In some embodiments, a 15-mer has a Tm of less than about 60° C.

A primer "3' segment or 3' binding region or 3' binding site or 3' hybridization region" is able to bind to a genomic sequence occurring in a genome at a particular frequency. In some embodiments, this frequency is between about 0.01% and 2.0%, such as, between about 0.05% and 0.1% or between about 0.1% and 0.5%. In some embodiments, the length of the "binding site" of a primer depends mainly on the averaged lengths of the predicted PCR products based on bioinformatic calculations. The definition includes, without limitation, a "binding region" of between about 4 and 12 bases in length. In more particular embodiments, the length of the 3' binding region can be, for example, between about 4 and 20 bases, or between about 8 and 15 bases. Binding regions having a Tm of between about 10° C. and 60° C. are included within the definition. The term, "primer binding segment," when used herein refers to a primer of specified sequence.

The term "random or random region" refers to a region of an oligonucleotide primer that is able to anneal to unspecified sites in a group of target sequences, such as in a genome. The term "random primer" as used herein refers to a primer that may include a 3' segment target specific binding region and a 5' segment artificial sequence. The "random region" facilitates binding of the primer to target DNA and binding of the polymerase enzyme used in PCR amplification to the duplex formed between the primer and target DNA. The random region nucleotides can be degenerate or non-specific, promiscuous nucleobases or nucleobase analogs. The length of the "random region" of the oligonucleotide primer, among other things, depends on the length of the specific region. In certain embodiments, without limitation, the "random region" is between about 2 and 15 bases in length, between about 4 and 12 bases in length or between about 4 and 6 bases in length. In another embodiment, the specific and random regions combined will be about 9 bases in length, e.g., if the specific region has 4 bases, the random region will have 5 bases.

In some embodiments, the primer 3' segment comprises both a specific region and a random region or degenerate region. In other embodiments, the 3' segment includes a specific region, and a random region or a degenerate region. In other embodiments, the 3' segment of the target primer only includes a specific region, a random region, or a degenerate region. Of course, known regions (sequences that are known) can also be used or part of the options disclosed herein.

A polymerase is an enzyme that can perform template directed extension of a primer hybridized to the template. It can be a DNA polymerase, an RNA polymerase or a reverse transcriptase. Examples of DNA polymerases include: *E. coli* DNA polymerase I, Taq DNA polymerase, *S. pneumoniae* DNA polymerase I, Tfl DNA polymerase, *D. radiodurans* DNA polymerase I, Tth DNA polymerase, Tth XL DNA polymerase, *M. tuberculosis* DNA polymerase I, *M. thermoautotrophicum* DNA polymerase I, Herpes simplex-1 DNA polymerase, T4 DNA polymerase, thermosequenase or a wild-type or modified T7 DNA polymerase, 029 Polymerase, Bst Polymerase, Vent Polymerase, 9° Nm Polymerase, Klenow fragment of DNA Polymerase I. Examples of reverse transcriptase: AMV Reverse Transcriptase, MMLV Reverse Transcriptase, HIV Reverse Transcriptase. Examples of RNA polymerases include: T7 RNA polymerase or SP6 RNA polymerase, bacterial RNA polymerases and eukaryotic RNA polymerases.

Amplification refers to either producing an additional copy or copies of all or a segment of a target nucleic acid by template-directed primer extension (target amplification) or amplifying detection signal for qualitatively/quantitatively measurement (signal amplification) or both. Amplification can be performed under temperature cycled or isothermal conditions or combined. Amplification can be linear or exponential.

Many well-known methods of nucleic acid target amplification require thermocycling to alternately denature double-stranded nucleic acids and hybridize primers; however, other well-known methods of nucleic acid amplification are isothermal. The polymerase chain reaction, commonly referred to as PCR (Mullis, 1987 U.S. Pat. No. 4,683,202; Saiki et al., 1985, Science (New York, N.Y.), 230(4732), 1350-1354), uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA (Gelfand et al., "Reverse Transcription with Thermostable DNA Polymerases—High Temperature Reverse Transcription," (Gelfand, 1994, U.S. Pat. No. 5,322,770; Gelfand & Myers, 1994, U.S. Pat. No. 5,310,652). Another method of amplifying nucleic acid is called the LCR method (ligase chain reaction, Laffler, Carrino, & Marshall, 1993, *Anna/es De Biologie Clinique*, 51(9), 821-826). LCR (Laffler et al., 1993, *Anna/es De Biologie Clinique*, 51(9), 821-826) is based on the reaction in which two adjacent probes are hybridized with a target sequence and ligated to each other by a ligase. The two probes could not be ligated in the absence of the target nucleotide sequence, and thus the presence of the ligated product is indicative of the target nucleotide sequence. The LCR method also requires control of temperature for separation of a complementary chain from a template. Another method is strand displacement amplification (George T. Walker, Little, & Nadeau, 1993, U.S. Pat. No. 5,270,184; George T. Walker, 1995, U.S. Pat. No. 5,455,166; G. T. Walker et al., 1992, *Nucleic Acids Research*, 20(7), 1691-1696, 1992, *Proceedings of the National Academy of Sciences of the United States of America*, 89(1), 392-396), commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (Frailer, Spargo, Van, Walker, & Wright, 2002, European Pat. No. 0 684 315). Other amplification methods include: nucleic acid sequence based amplification (Compton, 1991, *Nature*, 350(6313), 91-92, Malek, Davey, Henderson, & Sooknanan, 1992), commonly referred to as NASBA; one that uses an RNA replicase to amplify the probe molecule itself (Lizardi, Guerra, Lomeli, Tussie-Luna, & Russell Kramer, 1988, *Nature Biotechnology*, 6(10), 1197-1202), commonly referred to as 013 replicase; a transcription-based amplification method (Kwoh et al., 1989, *Proceedings of the National Academy of Sciences of the United States of America*, 86(4), 1173-1177); self-sustained sequence replication (3SR), (Guatelli et al., 1990, *Proceedings of the National Academy of Sciences of the United States of America*, 87(5), 1874-1878; Landgren (1993) *Trends in Genetics* 9, 199-202; and Lee, H. et al., *NUCLEIC ACID AMPLIFICATION TECHNOLOGIES* (1997)); and, transcription-mediated amplification (Kwoh et al., 1989, *Proceedings of the National Academy of Sciences of the United States of America*, 86(4), 1173-1177; Kacian & Fultz, 1995, U.S. Pat. No. 5,480,784; Kacian & Fultz, 1996, U.S. Pat. No. 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.). Other illustrative amplification methods suitable for use in accordance with the present invention also include rolling circle amplification (RCA) (Fire & Xu, 1995, *Proceedings of the National Academy of Sciences*, 92(10), 4641-4645; Lizardi, 1998, U.S. Pat. No. 5,854,033); Nucleic Acid Amplification Using Nicking Agents (Van Ness, Galas, & Van Ness, 2006, U.S. Pat. No. 7,112,423); Nicking and Extension Amplification Reaction (NEAR) (Maples et al., 2009, US 2009-0017453 A1); Helicase Dependent Amplification (HDA) (Kong, Vincent, & Xu, 2004, US 2004-0058378 A1; Kong, Vincent, & Xu, 2007 US pat. U52007/0254304 A1); and Loop-Mediated Isothermal Amplification (LAMP) (Notomi & Hase, 2002, U.S. Pat. No. 6,410,278), and Quadruplex priming amplification (*Analyst*, 2014, 139, 1644-1652). Expar amplification (PNAS Apr. 15, 2003 100, 4504-4509). Cross priming amplification (Sci Rep. 2012; 2: 246). SMAP amplification (Nature Methods 04/2007; 4(3):257-62). Multiple displacement amplification (MDA, *Proceedings of the National Academy of Sciences* 2005, 102 (48): 17332-6.), Recombinase Polymerase Amplification (*Journal of Clinical Virology* 54 (4): 308-12). Single primer isothermal amplification (SPIA) (clinical chemistry, 2005 vol. 51 no. 10 1973-1981).

Another aspect of amplification is signal amplification. When a sufficient amount of nucleic acids to be detected is available, there are advantages to detecting that sequence directly, instead of making more copies of that target, (e.g., as in PCR and LCR). Traditional methods of direct detection including Northern and Southern blotting and RNase protection assays usually require the use of radioactivity and are not amenable to automation. Other techniques have sought to eliminate the use of radioactivity and/or improve the sensitivity in automatable formats. The cycling probe reaction (CPR) (Duck, Alvarado-Urbina, Burdick, & Collier, 1990b, *BioTechniques*, 9(2), 142-148), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. Branched DNA (bDNA), described by Urdea et al., 1987, *Gene*, 61(3), 253-264, involves oligonucleotides with branched structures that allow each individual oligonucleotide to carry 35 to 40 labels (e.g., alkaline phosphatase enzymes). While this enhances the signal from a hybridization event, signal from non-specific binding is similarly increased. Other signal amplification include: Invasive Cleavage of Nucleic Acids (Prudent, Hall, Lyamichev, Brow, & Dahlberg, 2006, U.S. Pat. No. 7,011,944); Hybridization Chain Reaction (HCR) (R. M. Dirks & Pierce, 2004, *Proceedings of the National Academy of Sciences of the United States of America*, 101(43), 15275-15278, R. Dirks & Pierce, 2012, U.S. Pat. No. 8,105,778) and G-quadruplex DNAzyme-based colorimetric detection. CHA amplification (*J. Am. Chem. Soc.*, 2013, 135 (20), pp 7430-7433). SMART signal amplification (Biotechniques 2002 March; 32(3):604-6, 608-11.)

Amplification products can be detected qualitatively (i.e., positive signal relative to control) or quantitatively (signal intensity related to absolute or relative amount of analyte giving rise to amplification product). Detection can include but does not require further analysis, such as sequencing of an amplification product. The methods provided by the invention may also include directly detecting a particular nucleic acid in a capture reaction product or amplification reaction product, such as a particular target amplicon or set of amplicons. Accordingly, mixtures of the invention can comprise specialized probe sets including TAQMAN®, which uses a hydrolyzable probe containing detectable reporter and quencher moieties, which can be released by a DNA polymerase with 5T→3' exonuclease activity (Livak, Flood, & Marmaro, 1996, U.S. Pat. No. 5,538,848); molecular beacon, which uses a hairpin probe with reporter and quenching moieties at opposite termini (Tyagi, Kramer, & Lizardi, 1999, U.S. Pat. No. 5,925,517); Fluorescence resonance energy transfer (FRET) primers, which use a pair of adjacent primers with fluorescent donor and acceptor moieties, respectively (Wittwer, Ririe, & Rasmussen, 2001, U.S. Pat. No. 6,174,670); and LIGHTUP™, a single short probe which fluoresces only when bound to the target (Kubista & Svanvik, 2001, U.S. Pat. No. 6,329,144). Similarly, SCORPION™ (Whitcombe, Theaker, Gibson, & Little, 2001, U.S. Pat. No. 6,326,145) and SIMPLEPROBES™ (Wittwer et al., 2003, U.S. Pat. No. 6,635,427) use single reporter/dye probes. Amplicon-detecting probes can be designed according to the particular detection modality used, and as discussed in the above-referenced patents. Other detection methods include: gel electrophoresis, mass spectrometry, or capillary electrophoresis, melting curve, nucleic acid-based fluorescent chelating dye such as SYBR™ green, or detection of amplification products using a fluorescent label and a soluble quencher (Will, Gupta, & Geyer, 2014, U.S. Pat. No. 8,658,366).

The term "multiplex amplification" refers to the amplification of more than one nucleic acid of interest. For example, it can refer to the amplification of multiple sequences from the same sample or the amplification of one of several sequences in a sample as discussed, for example, in George T. Walker, Nadeau, & Little, 1995 U.S. Pat. No. 5,422,252; and George T. Walker, Nadeau, Spears, et al., 1995, U.S. Pat. No. 5,470,723, which provide examples of multiplex strand displacement amplification. The term also refers to the amplification of one or more sequences present in multiple samples either simultaneously or in step-wise fashion.

Real-time amplification refers to an amplification reaction for which the amount of reaction product, i.e. amplicon, is monitored as the reaction proceeds. Forms of real-time amplification differ mainly in the detection mechanisms used for monitoring the reaction products. Detection methods are reviewed in Mackay, Arden, & Nitsche, 2002, *Nucleic Acids Research*, 30(6), 1292-1305, which is incorporated herein by reference.

The term "detection label" refers to any atom or molecule which can be used to provide or aid to provide, a detectable (preferably quantifiable) signal, and can be attached to a nucleic acid or protein. Labels may provide signals detectable by fluorescence, radioactivity, colorimetry, gravimetry, magnetism, enzymatic activity and the like. Detection labels can be incorporated in a variety of ways: (1) the primers comprise the label(s), for example, attached to the base, a ribose, a phosphate, or analogous structures in a nucleic acid analog; (2) nucleotides triphosphates are modified at either the base or the ribose (or to analogous structures in a nucleic acid analog) with the label(s); the label-modified nucleotides are then incorporated into a newly synthesized strand by an extension enzyme such as a polymerase; (3) modified nucleotides are used that comprise a functional group that can be used (post-enzymatic reaction) to add a detectable label; (4) modified primers are used that comprise a functional group that can be used to add a detectable label in a similar manner; (5) a label probe that is directly labeled and hybridizes to a portion of the amplicon can be used; (6) a label that can be incorporated into amplified products; (7) a label that can react with byproducts of amplification reaction.

The terms "thermally cycling," "thermal cycling", "thermal cycles" or "thermal cycle" refer to repeated cycles of temperature changes from a total denaturing temperature, to an annealing (or hybridizing) temperature, to an extension temperature and back to the total denaturing temperature. The terms also refer to repeated cycles of a denaturing temperature and an extension temperature, where the annealing and extension temperatures are combined into one temperature. A totally denaturing temperature unwinds all double-stranded fragments into single strands. An annealing temperature allows a primer to hybridize or anneal to the complementary sequence of a separated strand of a nucleic acid template. The extension temperature allows the synthesis of a nascent DNA strand of the amplicon.

The term "reaction mixture", "amplification mixture" or "PCR mixture" refers to a mixture of components necessary to amplify at least one amplicon from nucleic acid templates. The mixture may comprise nucleotides (dNTPs), a thermostable polymerase, primers, and a plurality of nucleic acid templates. The mixture may further comprise a Tris buffer, a monovalent salt, and $Mg^{2+}$. The concentration of each component is well known in the art and can be further optimized.

The terms "amplified product" or "amplicon" refer to a fragment of DNA amplified by a polymerase using a pair of primers in an amplification method such as PCR.

"Fluorophore" refers to a moiety that absorbs light energy at a defined excitation wavelength and emits light energy at a different defined wavelength.

A "quencher" includes any moiety that is capable of absorbing the energy of an excited fluorescent label when it is located in close proximity to the fluorescent label and is capable of dissipating that energy. A quencher can be a fluorescent quencher or a non-fluorescent quencher, which is also referred to as a dark quencher. The fluorophores listed above can play a quencher role if brought into proximity to another fluorophore, wherein either FRET quenching or contact quenching can occur. It is preferred that a dark quencher which does not emit any visible light is used. Examples of dark quenchers include, but are not limited to, DABCYL (4-(4'-dimethylaminophenylazo) benzoic acid) succinimidyl ester, diarylrhodamine carboxylic acid, succinimidyl ester (QSY™-7), and 4',5'-dinitrofluorescein carboxylic acid, succinirnidyl ester (QSY™-33), quencherl, or "Black hole quenchers" (BHQ™-1, BHQ™2 and BHQ™-3), nucleotide analogs, nucleotide G residues, nanoparticles, and gold particles.

The term "mutation" refers to one or more nucleotides in a target nucleic acid sequence that differ from a prototypical form of the target nucleic acid designated wildtype. The sequence designated wildtype is the most common allelic form of a sequence, the first discovered form of the sequence, and/or a form of the sequence associated with a normal (non-diseased phenotype). Single nucleotide polymorphisms (SNPs) are one form of mutation.

The term "surface" refers to any solid surface to which nucleic acids can be covalently attached, such as for example latex beads, dextran beads, polystyrene, polypropylene surface, polyacrylamide gel, gold surfaces, glass surfaces and silicon wafers. Preferably the solid support is a glass surface.

The term "attached to surface" as used herein refers to any chemical or non-chemical attachment method including chemically-modifiable functional groups. "Attachment" relates to immobilization of nucleic acid on solid supports by either a covalent attachment or via irreversible passive adsorption or via affinity between molecules (for example, immobilization on an avidin-coated surface by biotinylated molecules). The attachment must be of sufficient strength that it cannot be removed by washing with water or aqueous buffer under DNA-denaturing conditions.

A sticky end is a single-stranded end of a nucleic acid adjacent a double-stranded segment of the nucleic acid. Nucleic acids with stick ends with complementary sequences can anneal via the sticky ends and undergo ligation to one another.

An artificial sequence is a sequence lacking complementarity to or at least not intended to have complementarity to a naturally occurring target nucleic acid known or suspected may be present in a sample. Artificial sequences can serve as linkers joining segments hybridizing to a target nucleic acid, or as tails for labelling primers, among other purposes.

DETAILED DESCRIPTION

I. General

The invention provides methods of amplification from a single primer or a pair of forward and reverse primers of limited nucleotide composition. Limited nucleotide composition means that the primers are underrepresented in at least one nucleotide type. Such primers have much reduced capacity to prime from each other or to extend initiated by mispriming from other than at their intended primer binding sites in a target nucleic acid. The use of such primers for target-specific amplification requires identification of primer binding sites in a target nucleic acid that support primer binding and amplification. In some target nucleic acids, primer binding sites having complete complementarity to primers of limited nucleotide composition can be identified. More often, segments of limited nucleotide composition in target nucleic acids are too short by themselves to serves as primer binding sites. However, such sites can be adapted to undergo amplification with primers of limited nucleotide composition by a variety of techniques described below including the use of ancillary toehold or junction oligonucleotide, primer with mismatch hybridization to primer binding site, mismatch stabilizing agents and presence of limited numbers of the underrepresented nucleotide in the primers. The disclosed invention includes methods that can improve underrepresented primer hybridization efficiency to underrepresented primer binding site. The present methods can be used in a variety of amplification formats, such as PCR, TMA, ligase chain reaction, NEAR, LAMP, RPA, EXPAR, and so forth and with a variety of detection formats. The methods can also be multiplexed for detection of multiple target nucleic acids simultaneously.

II. Primer Design a. Basic Principles

The present method start with a basic concept of a limited nucleotide composition of primers in which one or more nucleotide type(s) is underrepresented (e.g., A, T, C and no G) and then selects the best primer binding sites within a target nucleic acid for pairing with primers of that composition (e.g., A, T and G). Depending on the primer binding sites selected, the nucleotide composition of the primers may then be further adjusted (e.g., by allowing a limited number units of an underrepresented nucleotide) to improve complementarity with to the primer binding sites.

A preferred primer design is that one and only one of the four standard nucleotide types is underrepresented in both the forward and reverse primers. In other words, such primers can consist of A, T/U and C with G underrepresented, A, T/U, G with C underrepresented, A, G and C with T underrepresented or T, G and C with A underrepresented. The underrepresented nucleotide type is preferably G or C. If the underrepresented nucleotide type is present at all in a primer, it is preferably at position(s) other than the 3' nucleotide, most preferably as the 5' nucleotide or a 5' tail nucleotide linked to the 5' nucleotide of the primer. Inclusion of a 5' underrepresented nucleotide increases the melting temperature (TM) of primer binding without significantly increasing in unintended amplification products.

The 3' nucleotide of a primer is preferably occupied by the complement of the underrepresented nucleotide type. For example, if the underrepresented nucleotide type is G, then the 3' nucleotide is preferably C and vice versa. The terminal C or G inhibits primer dimer extension because there is no complementary base on the primers for it to pair with. The elimination or underrepresentation of one nucleotide type substantially limits the number of nucleotides than can form Watson-Crick pairs between the primers or between primers and mismatched primer binding sites. Correct base paring of the 3' nucleotide of a primer is of greatest importance in its ability to support template dependent extension. Use of the complement of the underrepresented nucleotide type at this position substantially reduces primer dimer and primer mismatch extension.

Other features of primer design are similar to conventional primers. A primer has a sequence complementary to its primer binding site. Some primers are at least 15, 20, 25, 30, 35 or 40 nucleotides long. Some primers are no more than 25, 30, 40, 50 or 75 nucleotides long. Primers can have any permutation of these lower and upper lengths, e.g., from 15-50 of 20-30 or 30-40 nucleotides. The melting temperature of a primer to its primer binding site can be for example 45-80 C or preferably 55-65 C. By convention, for primers binding to opposite strands, one of which is the coding strand, the forward primer is complementary to the non-coding strand so the extended product is the coding strand, and the reverse primer to the coding strand so the extended product is the noncoding strand. For target nucleic acids not having coding and noncoding strands, designation of forward and reverse primer is arbitrary. Such is also the case when forward and reverse primers bind to primer binding sites on the same strand. Primers can have 5' tails not complementary to a target nucleic acid. Such tails can be used for attaching fluorophore or quenchers, or can contain identification codes, or can link discontinuous segments of primer complementary to its target nucleic acid.

Amplification conditions are usually similar to conventional primers in terms of buffers, $Mg^{2+}$, enzymes, temperatures and so forth. Conventional amplification is performed with all four standard nucleotide types present as dNTP monomers. Amplification with primers of limited nucleotide composition can be so performed, but can also be performed with the complements of the underrepresented nucleotide type(s) absent or present at reduced concentration or provided as ddNTP(s), as further described below.

Usually but not invariably forward and reverse primers bind to opposite strands of a target nucleic acid. Thus, one strand of a target nucleic acid contains for example, the complement of the forward primer binding site and the reverse primer binding site, and the other strand contains the forward primer binding site and complement of the reverse primer binding site. In some formats, forward and reverse primer binding sites are on the same strand. For example, linked forward and reverse primers can bind to binding sites on the same strand and amplify by a rolling circle mechanism. Some pairs of three way junction primers can also bind to sites on the same nucleic acid strand, such that one primer serves as a template for the other.

The search for suitable primer binding sites in a target nucleic acid is informed by the principles of primer design in that the primer binding sites should be complementary to the primers. For example, for use with primers that are underrepresented in a single nucleotide type, one can search a target nucleic acid for a forward primer binding site and a reverse primer binding site that are underrepresented in the complement of the nucleotide type underrepresented in the primers. Preferably, a forward primer binding site and a reverse primer binding site are identified in which the complement of the underrepresented nucleotide type is absent. However, if such sites cannot be found, other primer binding sites can be still be used, preferably those in which the number of units of the complement of the underrepresented nucleotide type is minimized. Often, the complement of the underrepresented nucleotide type in the primers is itself underrepresented in the primer binding sites, but this is not essential. Some forward and reverse primer binding sites each have no more than 4, 3, 2 or 1 units of the complement of the nucleotide underrepresented in the primers.

For ATC primers, software can be used to look for contiguous or proximate ATC and ATG regions representing the complement of the forward primer binding site and reverse primer binding site respectively. To use ATG primers, software can look for ATG and ATC regions for the complement of the forward primer binding site and the reverse primer binding site respectively. To use CGA primers, software can look for CGA and CGT regions representing the complement of the forward primer binding site and the reverse primer binding site respectively. To use CGT primers, software can look for CGT and CGA regions for the complement of the forward primer binding site and the reverse primer binding site respectively.

The complement of the forward primer binding site (or the forward primer binding site itself if on the same strand as the reverse primer) and the reverse primer binding site can be contiguous with one another or separated by intervening nucleotides in a strand of the target nucleic acid. The intervening nucleotides, if any, may exclude the underrepresented nucleotide in the primers and its complement, or may include one or both of these nucleotides and either of the other two of the four standard nucleotide types. If non-contiguous, the complement of the forward primer binding site (or the forward primer binding site itself) and reverse primer binding site should be close enough together to prime extension compatible with the amplification technique (e.g., no more than 100, 500, 1000, or 10000 nucleotides).

FIG. 1 shows a simple representation of the method in which the forward and reverse primers each consist of A, T and C nucleotides, with a C nucleotide at the 3' positions. In other words G is the underrepresented nucleotide type. The reverse primer binding site consists of A, T and G (the complement of the C, and underrepresented in the primers). The complement of the forward primer binding site shown consists of A, T and C, implying that the forward primer binding site (like the reverse primer binding site) consists of A, T and G. The forward and reverse primers are perfectly complementary to the forward and reverse primer binding sites, respectively. The complement of the forward primer binding site and the reverse primer binding sites are contiguous. An amplification product can form when a reaction is supplied with the three nucleotide triphosphate monomers complementary to the three-nucleotide-types in the forward and reverse primers, A, T and G. Primer dimer formation and mispriming are inhibited as described because few bases can pair between primers and or between a primer and a mismatched primer binding site. But even if the primers could sufficiently bind to unintended primer binding sites sufficient to initiate extension, no amplification product would form because the omitted nucleotide triphosphate monomer in the amplification mix brings amplification to a stop whenever the extended chain need to incorporate a C.

Figure 7:
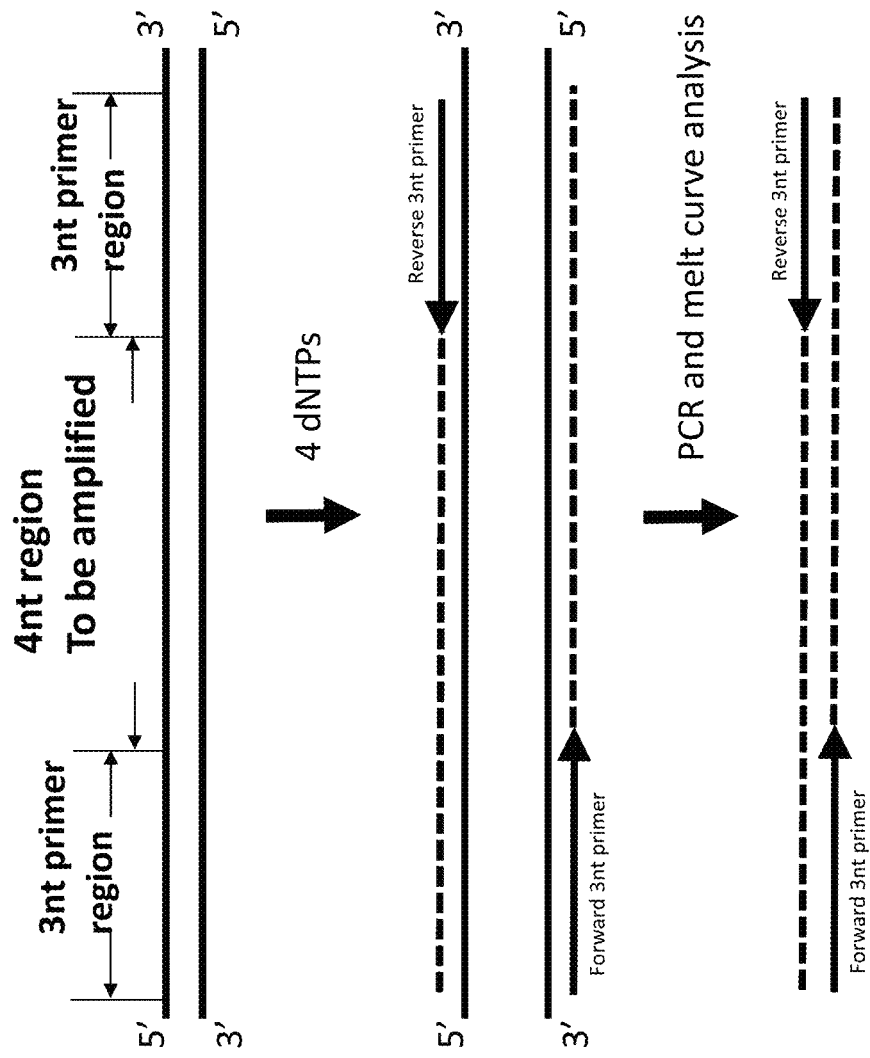
FIG. 7 shows amplification of a template in which three nucleotide-type primer binding sites are separated by a segment including all four-nucleotide-types. Amplification is performed in the presence of all four-nucleotide-types mononucleotide triphosphates.

Alternatively, the primer binding sites can be noncontiguous and separated by a region including all four of the standard nucleotides, as shown in FIG. 7. In such a case, amplification is performed with all four of the standard nucleotide triphosphate monomers.

b. Mismatches Between Primer Binding Sites and Primers

FIG. 5 shows a more typical situation in which a search of a target nucleic acids for forward and reverse primer binding sites showed no suitable pair of forward and reverse prime binding sites having complete complementarity to primers consisting of A, T, C nucleotides (i.e., no primer binding sites in which the underrepresented nucleotide type is entirely absent). The longest ATC region contains 7 nucleotides (CATCCTC) and the longest ATG region (CGATTGGTATG) contains 12 nucleotides. These regions are not long enough to use as primers because their Tm's are too low. In such cases, primers mismatched with the primer binding sites can be used. In FIG. 5 the forward primer binding site has three units of C and the reverse primer binding site has two units of C aligned with C-nucleotides in the primers. Accordingly when such primers and primer binding sites are hybridized with one another there are three mismatch positions between forward primer and its binding site and two mismatches between the reverse primer and its binding site. Nevertheless hybridization and extension can still occur albeit with reduced efficiency. Hybridization and extension can be increased if the reaction mix is supplied with a mismatch stabilizing agent. Mismatch binding or stabilizing agent are any molecules or any modification in underrepresented primers that can stabilize the underrepresented primer hybridization with underrepresented primer binding sites through chemical interaction or physical interaction (se FIG. 6). Modification of underrepresented primers may be modified in any way, as long as a given modification is compatible with the desired function of a given underrepresented primers as can be easily determined. Modifications include base modifications, sugar modifications or backbone modifications, such as PNA, LNA, or 2' fluorine 2' methyloxy, Rhodium metalloinsertors as examples of mismatch stabilizing agents are described by Ernst et al. J. Am. Chem. Soc. 131, 2359-2366 (2009). Chemicals such as rhodium metalloinsertors can specifically bind DNA mismatches and have a binding constant of $2.0 \times 10^7 M^{-1}$ at a CC mismatch. Binding of rhodium metalloinsertors can increase the melting temperature of double-stranded DNA including a mismatch by 18.7° C. Therefore such mismatch binding reagents can be added to three-nucleotide-type primer PCR reactions to specifically stabilize mismatches and increase PCR efficiency. As well as C—C mismatches, T-C or A-C mismatches can be stabilized by such reagents among other possibilities. Even with such stabilizing agents, mismatched primers may hybridize to a template with slightly reduced efficiency but amplification can proceed.

c. Inclusion of a Few Units of Underrepresented Nucleotide

Alternatively or additionally to using a mismatch stabilizing agent, the number of mismatches can be reduced by introducing a limited number of units of the underrepresented nucleotide type (typically up to 2 internal position) at positions in a primer that reduce the number of mismatches with its primer binding site. An underrepresented nucleotide can also be used at the 5' position of the primer or in a tail immediately 5' to the 5' end of the primer. For example, with the primers and primer binding sites shown in FIG. 5, introduction of two G's into each of the forward and reverse primers reduces the mismatches to one in the case of the forward primer and none in the case of the reverse primer.

The choice whether to use a mismatch stabilizing agent or to include one or more units of the underrepresented nucleotide type in the primers depends on the number of mismatch positions between hypothetical forward and reverse primers completely lacking the underrepresented nucleotide types and their respective binding sites. If there are more than two mismatches between such a primer and its binding site or a mismatch occurs close (e.g., within 4 nucleotides) to the 3' end of a primer, it is preferred to eliminate one or more mismatches by inclusion of one or more underrepresented nucleotides in the primer.

In the case of ATC primers, instead of introducing G into the underrepresented primer, one or more unnatural bases can be introduced as alternative as long as the unnatural bases can help to reduce primer dimer interaction comparing to conventional ATGC primers. An example of the unnatural bases is inosine. Introducing G increases the hybridization efficiency of primer to its binding site, but also increases inter- and intra-primer interactions because CG pairs are present now. Inosine on the other hand maintains the hybridization efficiency of primer to its binding site with the help of flanking bases pairs. But a single or a few of C and I pairs between or within primers make little contribution to binding and do no result in substantial primer dimer formation. Preferably such primers consist of a 3' segment that contains only A, T, and C to minimize the mismatch effect on primer extension efficiency, and a 5' segment including only any number of inosine residues (e.g., 1-10)

In situations in which the primer binding sites are not perfectly matched with primers in which an underrepresented nucleotide type is entirely absent, the amplification can still occur without the complement of the underrepresented nucleotide type in the primers being supplied as a nucleotide triphosphate monomer, but proceeds more efficiently if this nucleotide type is supplied. This nucleotide type can however by supplied at reduced concentration compared with the others of the standard four nucleotides (e.g., <10×, <100× or <1000× each of the other nucleotide triphosphate monomers), or can be supplied as a dideoxy NTP. Extension resulting from mispriming is terminated by the dideoxy NTP. Use of either strategy (reducing nucleotide concentration or use of ddNTP) decreases unintended amplification products from mispriming or primer dimers. The primers with inosine substitutions require dCTP in the reaction for efficient extension on the inosine bases. The dCTP however can be supplied at reduced concentration compared with the other types of nucleotide triphosphate monomers.

When target sequences are from organisms of a variety of species or genotypes, the template is a mixture of more than one allele. Primer with underrepresented nucleotide can contain degenerate bases at certain positions to match different sequence variations.

Underrepresented primers with mismatches or inosine substitutions can be used in combination with the conventional primers of their original sequences (i.e. no mismatches or inosine substitutions) in amplification reactions. However, a conventional primer should have reduced concentrations, between 0.1% to 50% of an underrepresented primer's concentration. The conventional primers hybridize to their binding sites more efficiently than the underrepresented primers and their extension products provide the underrepresented primers with more templates. The types of dNTP which are complement of the underrepresented nucleotide are provided at reduced concentrations as mentioned above or are completely omitted depending on the composition of the underrepresented primers. Such combination of conventional and underrepresented primers facilitates the amplification from underrepresented primers and maintains the low primer-primer interactions.

d. Toe Hold Primers

Figure 14:
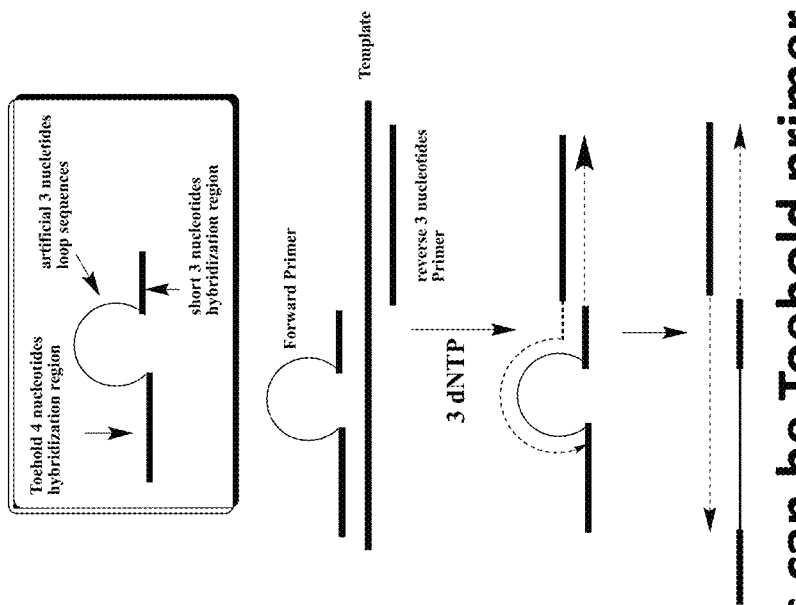
FIG. 14 shows linking of a three nucleotide-type primer too short to prime amplification by itself to a toe hold segment.
Figure 15:
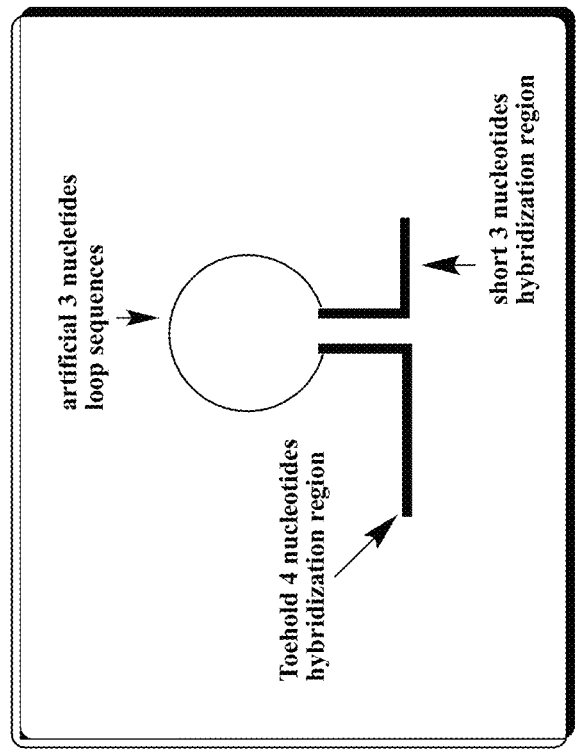
FIG. 15 shows an alternative toe hold format.

FIG. 14 shows a situation in which a search of a target nucleic acid for suitable primer binding sites shows a suitable reverse primer binding site and a potential forward primer binding site, which has limited nucleotide composition (e.g., one nucleotide type is absent), but is too short by itself to support primer binding. In this situation, a forward primer is designed in which a primer segment with an underrepresented nucleotide type is linked at its 5' end to a nucleic acid segment of artificial sequence (i.e., not complementary to the target nucleic acid) having the same underrepresented nucleotide, which is itself linked at its 5' end to a second primer segment in which all four nucleotides are represented, which is complementary to the target nucleic acid. Such a primer can hybridize to the target nucleic acid with the segment of artificial sequence forming a loop flanked by the two primer segments hybridized to the target nucleic acid. Because the second primer segment helps the first primer segment form a duplex the target nucleic acid despite the first primer segment itself being too short to form a stabile duplex, the second primer segment can be referred to as a toehold primer. Such primers can be amplified in an amplification mix in which the complement of the underrepresented nucleotide type is not supplied as a nucleotide triphosphate monomer or in which all four standard nucleotide triphosphate monomers are supplied. Either or both primers can be supplied with toehold sequences and artificial sequences as described. In a further variation instead of the artificial sequence forming just a loop when the first and second primer segments are hybridized to the target nucleic acid as shown in FIG. 14, the artificial sequence can form a stem loop structure shown in FIG. 15. The 3' end of the linker region is the complement to the 3' end of the 5' priming region. The primer forms a hairpin structure which stabilizes its hybridization with the template and increases its amplification efficiency.

In another format, a single primer binding site can use two kinds of primers for amplification simultaneously. One primer is called helper in which the 3' primer segment with underrepresented nucleotide is directly linked with the 5' primer segment that is similar to conventional primer. The helper can hybridize with target with sufficient efficiency to initiate amplification due to help from conventional primer segment. For detection of multiple alleles, the 5' primer segment can contain degenerate bases. The other primer is underrepresented primer and very similar to the helper primer by simply changing the fourth nucleotides in its 5' segment with complement of underrepresented nucleotide type. The helper is provided in limited amount to minimize unintended amplification, while sufficient to initiate amplification. The second primer is provided in regular concentration to carry on the amplification.

e. Three Way Junction Primers

Figure 16:
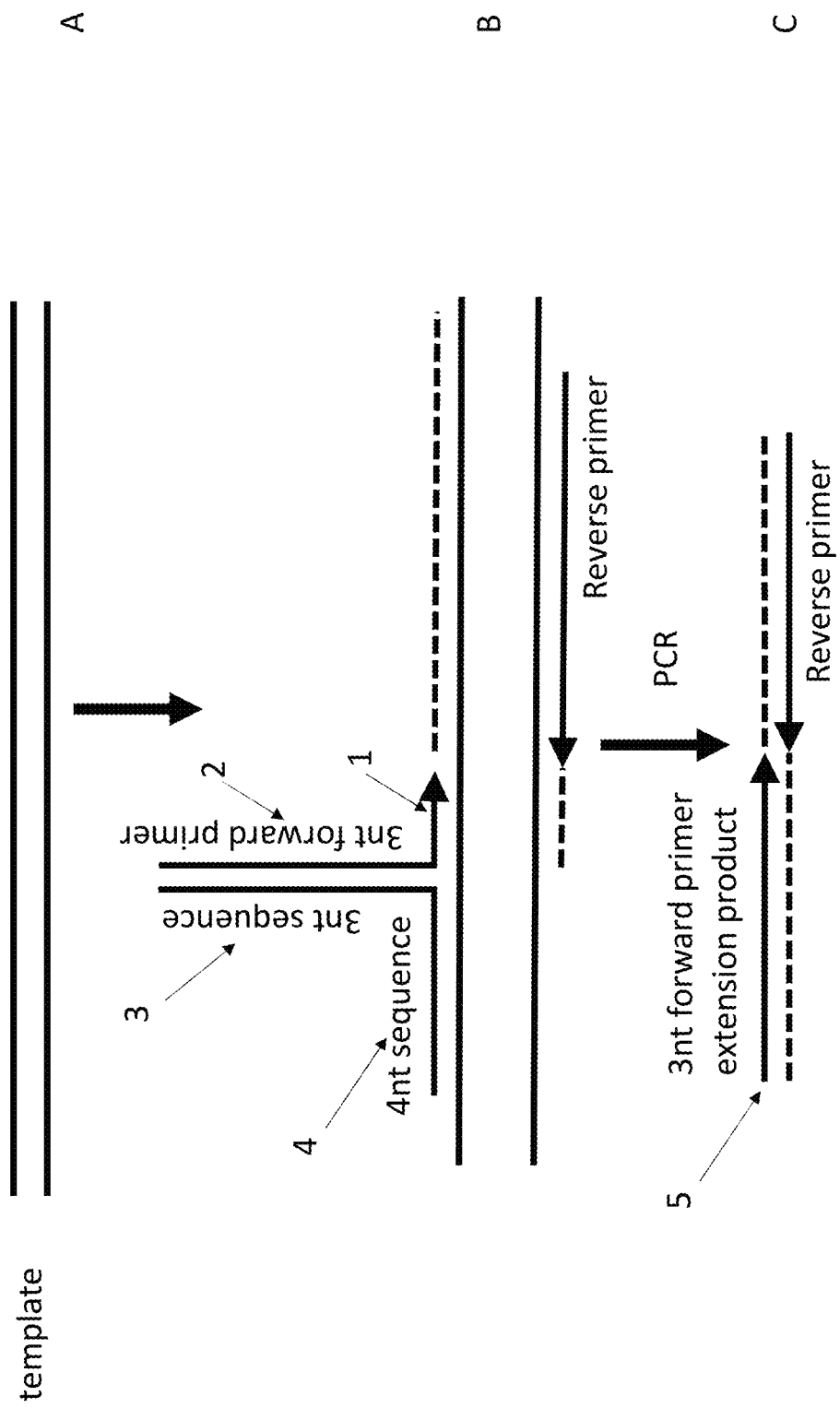
FIG. 16A-C shows use of a three way junction when a three nucleotide primer is too short to support amplification by itself.

The type of situation shown in FIG. 14 in which one or both of the primer binding sites with an underrepresented nucleotide type is too short to support primer binding can alternatively be addressed by the use of three way junction sequences as shown in FIGS. 16A-C. Here a primer segment with an underrepresented nucleotide type (1) is linked at its 5' end to an artificial segment of the same underrepresented nucleotide type (2). This primer is then held in place on the target nucleic acid with a junction primer comprising a target binding site (4) and the complement of the artificial segment (3). The target binding site of the junction primer includes all four standard nucleotides. The junction primer can be used at reduced concentration (copy number) relative to the limited nucleotide composition primer. Either or both of the forward and reverse primer can be replaced by three way junction sequences.

Figure 17:
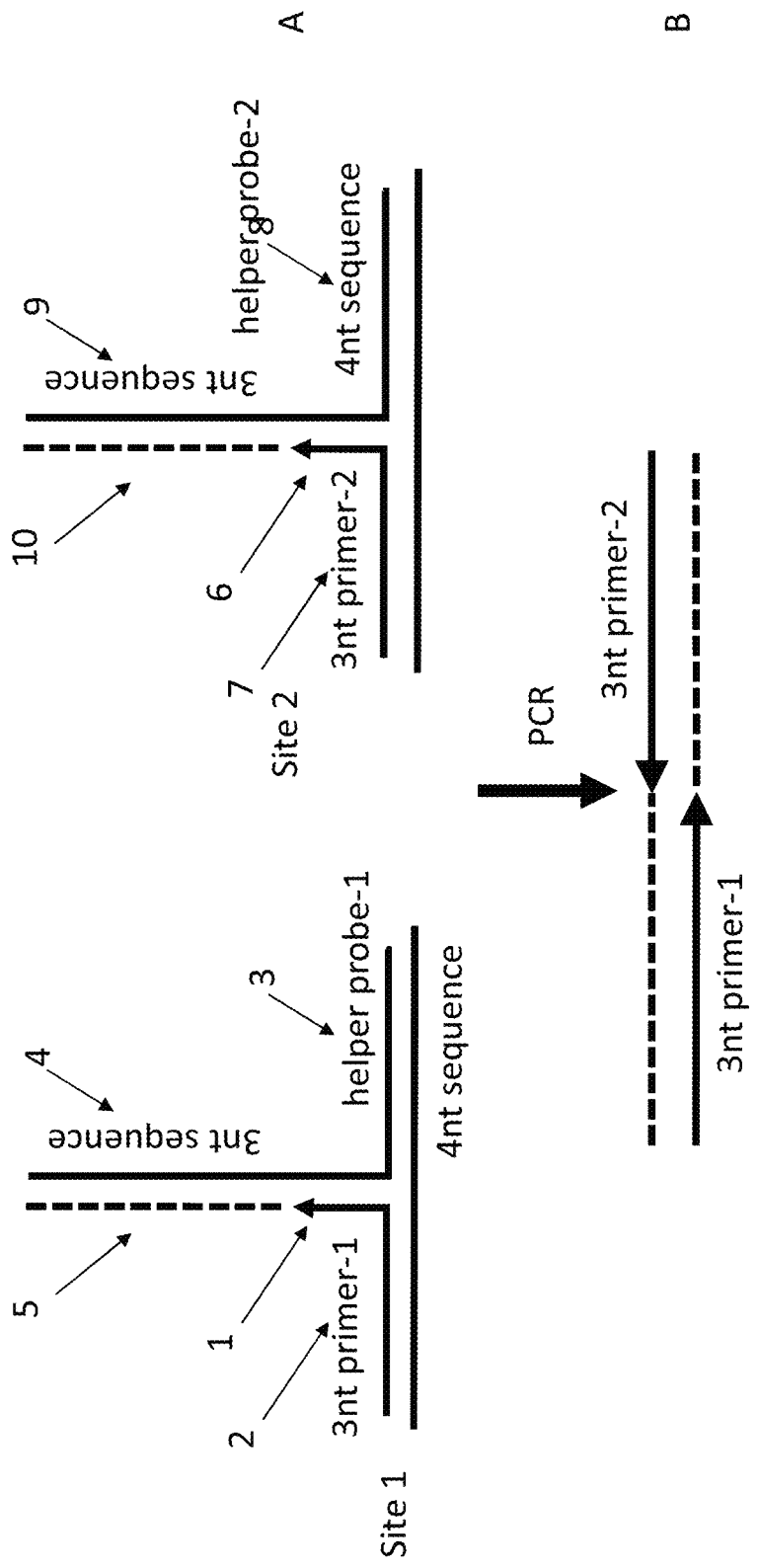
FIGS. 17A-B and 18A-B show alternative three-way junction formats.

FIG. 17 shows an alternative format for three way junction probes. In this format a primer segment with an underrepresented nucleotide type (2) is linked at its 3' end to an artificial segment underrepresented in the same nucleotide typed (1). A junction probe is supplied having a target binding segment (3) linked at its 5' end to an artificial segment (4) having an underrepresented nucleotide that is the complement of the nucleotide underrepresented in the primer segment (2). The two artificial segments (1) and (4) are complementary to one another but of unequal lengths such that the shorter artificial segment (1 can extend using the longer artificial segment as a template. The reverse primer is designed using an analogous approach. The extension products from the forward and reverse primers are of complementary sequence and can serve as a template for extension of the other resulting in an amplification product.

FIG. 31B shows a similar arrangement in which a primer segment with an underrepresented nucleotide type is linked at its 3' end to a nucleic acid having the complement of a promoter sequence. A junction probe is supplied having a target binding segment with an underrepresented nucleotide linked at its 5' end to a nucleic acid having the promoter sequence, which is in turn linked at its 5' end to a nucleic acid with an artificial sequence. The promoter can initiate transcription to generate a transcript of the artificial sequence linked to the promoter indicating presence of the target nucleic acid.

FIG. 31A shows a similar arrangement to FIG. 31B but in which as an alternative to a promoter the junction probe can be linked through a nucleic acid with a restriction site to the nucleic acid with an artificial sequence. Such an arrangement supports nicking amplification. Oligonucleotide1 (left) consists of a 3' artificial segment with restriction site linked to a 5' segment, which is a three-nucleotide-type primer. Oligonucleotide2 (right) consists of a 5' artificial three-nucleotide-type sequence linked to a 3'segment which is three-nucleotide-type primer, and a linker segment complementary to the 3' sequence of oligonucleotide1. Oligonucleotides1 and 2 form a three way junction structure with the template. Oligonucleotide1 extends and forms full restriction site. A nicking enzyme nicks and releases extended product. Nicking and extension repeat in later cycles.

Figure 18:
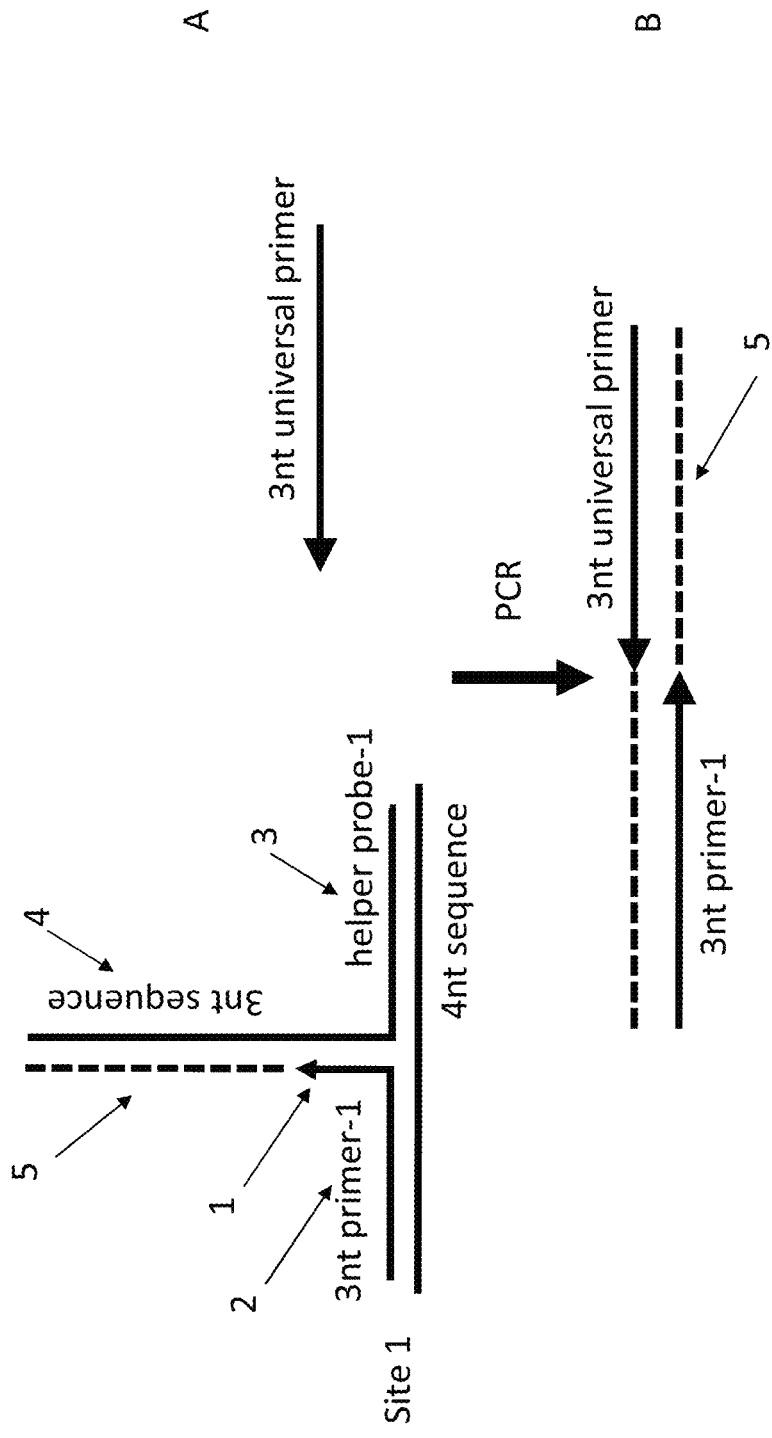

FIGS. 18A, B shows a variation on the format of FIG. 17 in which the forward primer is as described in FIG. 17 but the reverse primer is an artificial universal primer having the same underrepresented nucleotide type as the forward primer. The forward primer is specific to target sequence and the universal primer remains same for different targets. In FIG. 18A, the three nucleotide-type region (sequence 2) of primer 1 hybridizes to a template. The 3' end of primer 1 (sequence 1) hybridizes to the three nucleotide-type region (sequence 4) and extends sequence 5. Extension product of the forward primer can serve as a template for extension of the universal primer generating an amplification product (FIG. 18B).

f. Rolling Circle Formats

FIG. 31C shows forward and reverse primers linked by a nucleic acid of artificial sequence. Both the forward and reverse primers and the artificial sequence have an underrepresented nucleotide type. The forward and reverse primers bind to binding sites on the same strand of a nucleic acid target and the nick is filled with ligase. After ligation, free primers are digested to leave only ligated circular products. The ligated product can be amplified by rolling circle replication.

g. Detection Formats

The above methods are compatible with a variety of detection formats. In one format, one or more of the nucleotide triphosphate monomers used for amplification is labeled, so that detection label gets incorporated into an amplification product with the labeled monomer. Differentiation of amplification product from any unincorporated labeled monomer allows detection of the amplification signal. In another format, either or both of the forward and reverse underrepresented primers is linked to a detection label. Differentiation of amplification product from any unincorporated labeled primer allows detection of the amplification signal. The detection label may be attached at any position of the primer. In another format, either or both of the forward and reverse underrepresented primers are linked to an enzyme recognition segment (e.g., a promoter recognized by a polymerase). In another format, both the nucleotide triphosphate monomers and either or both of the forward and reverse underrepresented nucleotide primers used for amplification are labeled. Differentiation of amplification product from any unincorporated labeled primer and or nucleotide triphosphate monomers allows detection of the amplification signal. In another format, special reagents or chemicals are included in the amplification mixture such as SYBR™ allows to monitor the amplification. In another format, a side product such pyrophosphate allows detection of the amplification reaction. In another format, the amplification product is detected based on mass, size, temperature, electricity, radiation, color, absorption, reflection, speed, and so forth. In another format, either or both of the forward and reverse underrepresented primers or portion of the underrepresented primers are labeled with fluorophores. Quenching chemicals can be provided in the amplification reaction such as new methylene blue, 7-deaza-2'-deoxyguanosine-5'-triphosphate, or 7-deaza-2'-deoxyadenosine-5'-triphosphate. The quenching chemicals specifically incorporate into amplification products and quench the fluorescence signal, whereas they have no effect on free fluorophore labeled primers.

Figure 19:
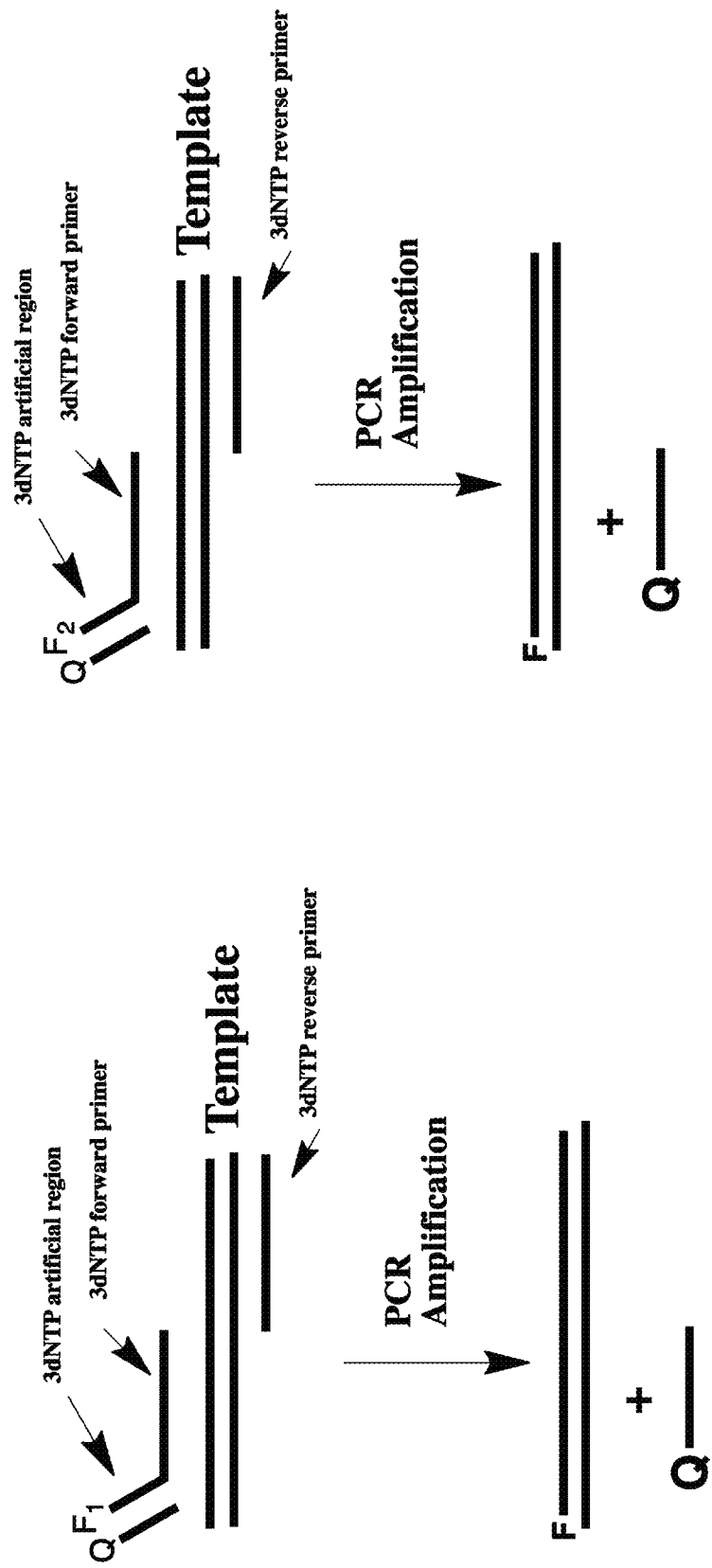
FIG. 19 shows multiplex amplification and detection in which a three-nucleotide-type primer is linked at its 5' end to an artificial segment linked to a fluorophore.
Figure 20:
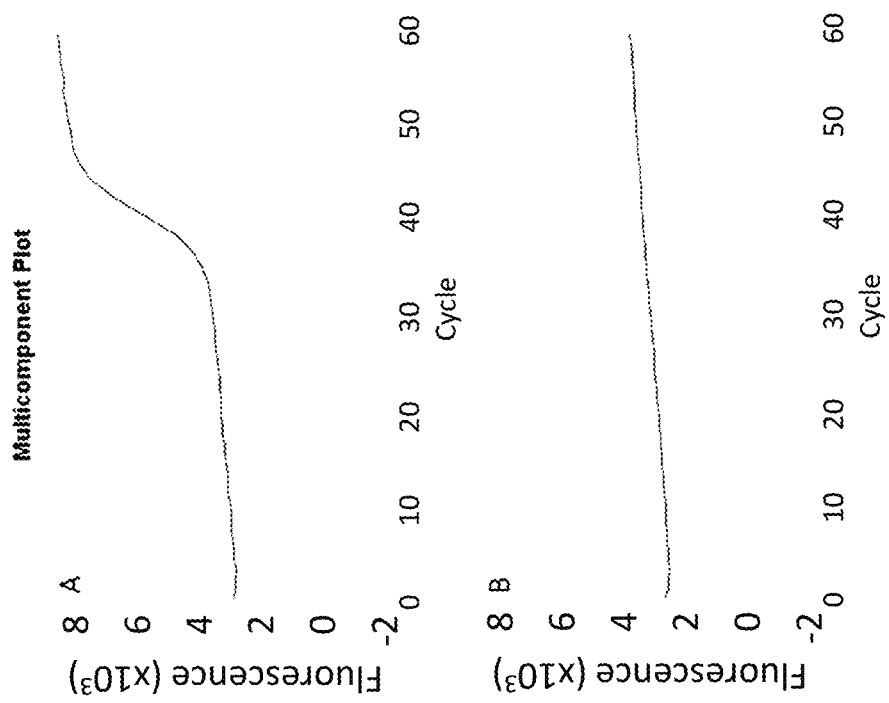
FIGS. 20A, B show florescence over time for template amplification (A) and no template control (B).

In a variation, the artificial segment is initially hybridized to a complementary oligonucleotide linked to a quencher, which quenches the fluorescence from the fluorescent label. The complementary oligonucleotide with the quencher becomes detached in performing the amplification, so that a fluorescent signal emerges as the amplification proceeds. FIG. 19 shows, primer 1 at left is labelled with F1. Primer 2 at right is labeled with F2. Such an amplification product can be detected in real time without removal of unincorporated fluorescently labelled primer. Optionally, such a detection format can be performed with an excess of the unlabeled primer (reverse primer as shown in FIG. 20) to improve probe detection efficiency. Such a detection format can be multiplexed for simultaneous detection of multiple targets.

Figure 25:
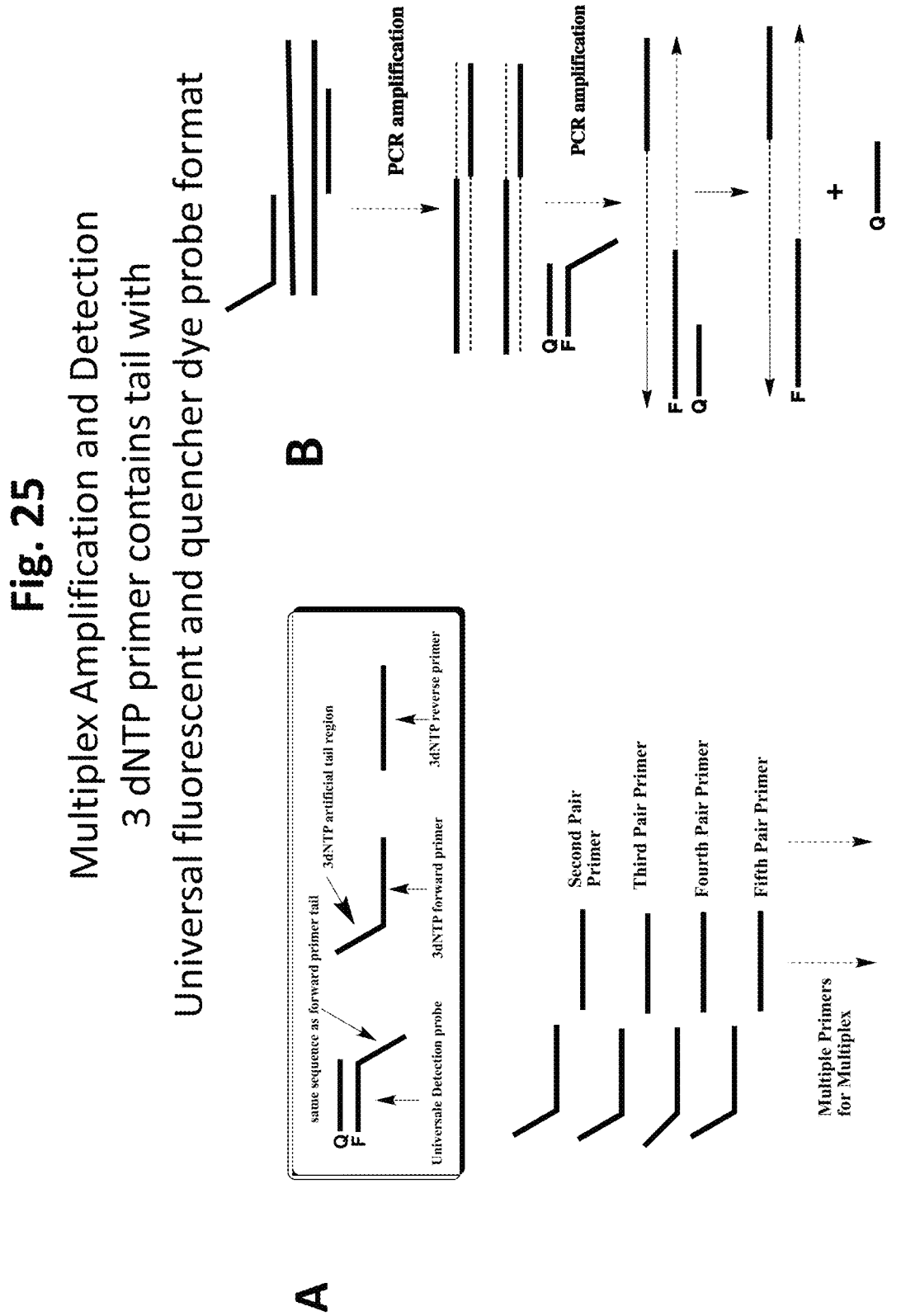
FIG. 25 multiplex amplification and detection using a three nucleotide-type primer with a universal fluorescent tail and quencher.

FIG. 25A shows the composition of primers used an exemplary method. One of the three nucleotide-type primers is tailed at its 5' end with universal artificial three nucleotide sequences. A 5' end fluorophore labelled probe consists of a 3' sequence which is the same as the artificial sequence of a primer and a 5' detection probe. A 3' end quencher labelled probe complementary to the 5' detection probe is also provided Fluorescence is quenched when no amplification occurs.

FIG. 25B shows multiple primer pairs with the same 5' artificial tail used to detect multiple targets. A reverse primer extends to the artificial tail sequence and generates the complementary sequence to the artificial tail. The newly generated reverse primer extended on its 3' end hybridizes to the fluorescence labeled probe and extends to replace the quencher labeled probe. This ends with free fluorescence to be detected. Different fluorophore labelled probes and primer tail sequences can be used for multicolor detection.

Figure 23:
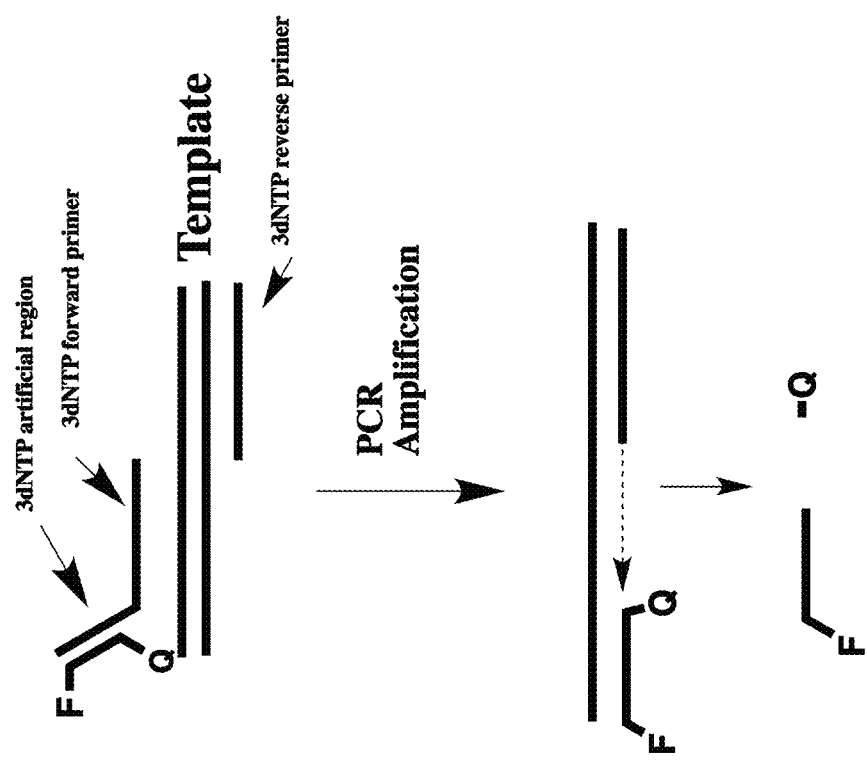
FIG. 23 shows a Taqman® probe format.

In another detection format (Taqman® format) shown in FIG. 23, one of the primers can be linked at its 5' end to an artificial segment having the same underrepresent nucleotide(s) as the primer to which it is linked. Such a primer is supplied with a complementary oligonucleotide having a fluorescent label at one end and a quencher at the other. When reverse primer extension meets the quencher oligonucleotide, 5' exonuclease activity of the polymerase digests the Taqman® probe and separates the fluorophore and quencher giving rise to a fluorescent signal. Such a signal can be detected without removal of unused primer allowing real time detection.

Figure 38:
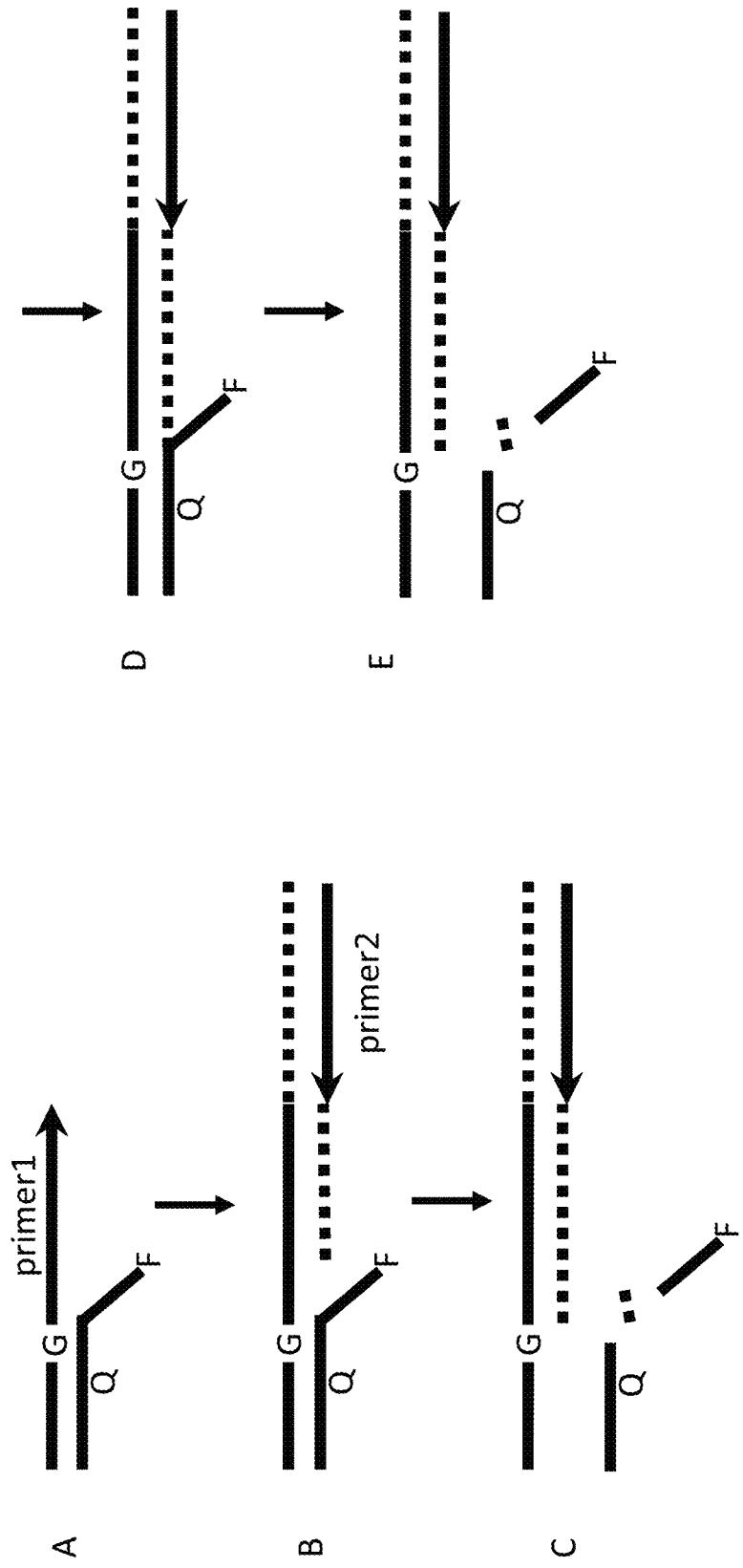
FIGS. 38A-E shows a multiplex amplification reaction with special tailed underrepresented primers and their partially complementary strand, and a detection method with the 5' Flap activity of DNA polymerase.

FIGS. 38A-E show another detection format using a 5' Flap endonuclease activity of Taq DNA polymerase. FIG. 38A shows the primer structure. One of the primers is linked at its 5' end to an artificial segment having the same underrepresented nucleotide(s) as the primer to which it is linked. A single nucleotide "G" serves as a linker between the primer and the artificial segment. A complementary oligonucleotide having a fluorophore labeled at one end and a quencher labeled internally is supplied at equal or excess amount. The 3' segment of the complementary oligonucleotide hybridizes to the artificial segment of the primer and the 5' segment is not complementary to the primer sequence. FIG. 38B shows that the primer has generated primer extension product and a reverse primer binds to the product and extends. FIG. 38C C shows that when reverse primer extension meets the junction of hybridization between the artificial segment and the complement oligonucleotide, 5' Flap endonuclease activity of the DNA polymerase cleaves the complement oligonucleotides and separates the fluorophore and quencher resulting in fluorescence signal. The extension of reverse primer stops at the "G" because dCTP is not provided in the reaction. Another complement oligonucleotide can now bind to the artificial segment on the primer (FIG. 38D) and is cleaved to release fluorescence signal (FIG. 38E). The process repeats and fluorescence signal is amplified.

FIGS. 39A, B show a real-time detection format amenable to multiplexing using a fluorophore quencher labeled oligo. FIG. 39A shows primer structure. One of the primers is linked at its 5' end to an artificial segment having the same underrepresented nucleotide(s) as the primer to which it is linked. A fluorophore and a quencher labeled oligonucleotide that has the same sequence as the artificial segment is also provided in amplification reaction. In its single strand form, the fluorophore and quencher are in proximity and the fluorescence is quenched. FIG. 39B shows that during the target amplification, reverse primer extensions generate the complementary sequence of the artificial tail. FQ labeled oligonucleotide, which has the same sequence as the artificial tail can hybridize to the synthesized complementary sequence. The fluorophore and quencher are no longer in proximity and fluorescence is released. This reaction can be facilitated by asymmetric reaction in which reverse primer is in excess amount so that single strands of the complementary sequence are available for the FQ oligonucleotide to hybridize.

FIG. 40A, B show a further real time detection format amenable to multiplexing. FIG. 40A shows the primer structure. One or both of the primers is linked at its 5' end to an artificial segment having the same underrepresented nucleotide(s) as the primer to which it is linked. A fluorophore and a quencher is attached to the artificial segment and at least one of the label is internal to the artificial segment. In the single strand form, the fluorophore and quencher are in proximity and the fluorescence is quenched. FIG. 40B shows that during the target amplification, the artificial segment becomes double-stranded. The fluorophore and quencher are no longer in proximity and fluorescence is released.

Figure 24:
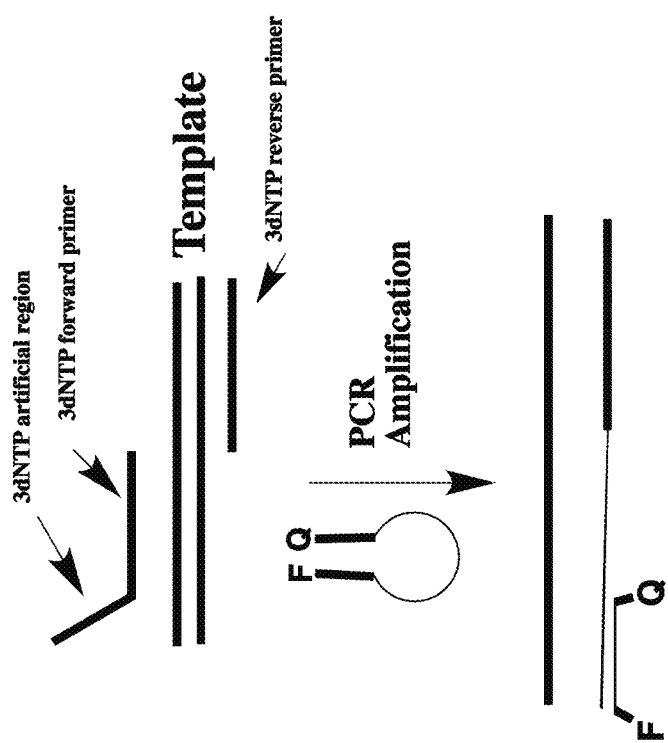
FIG. 24 shows a molecular beacon format.

FIG. 24 shows a further detection format (molecular beacon). One or both of the primers is again linked at its 5' end to an artificial segment which has the same underrepresented nucleotide(s) as the primer to which it is linked. The amplification is performed in the presence of a molecular beacon probe which has a hairpin stem structure with a fluorophore and quencher at the ends of the hairpin and the loop sequence complementary to the complement of the artificial segment linked to the primer. When an amplification product is formed the loop segment of the molecular beacon hybridizes to the artificial segment, separating the fluorophore and quencher generating a fluorescent signal. This signal can be detected in real time without removal of unincorporated molecular beacon.

All of the formats involving labeled primers or primers having linked artificial sequences that hybridize with labelled oligonucleotides can readily be multiplexed by using different fluorescent labels and different artificial sequence for each target to be detected. When multiplex amplifications are performed with multiple primers or primer pairs, the underrepresented nucleotide type(s) are usually the same in all primers present in the multiplex. For example, all primers can have an underrepresented G, or an underrepresented C.

Amplification products can also be detected by melt curve analysis (changes in absorption with temperature), mass spectrometry, gel electrophoresis, or capillary electrophoresis among other techniques.

Figure 37:
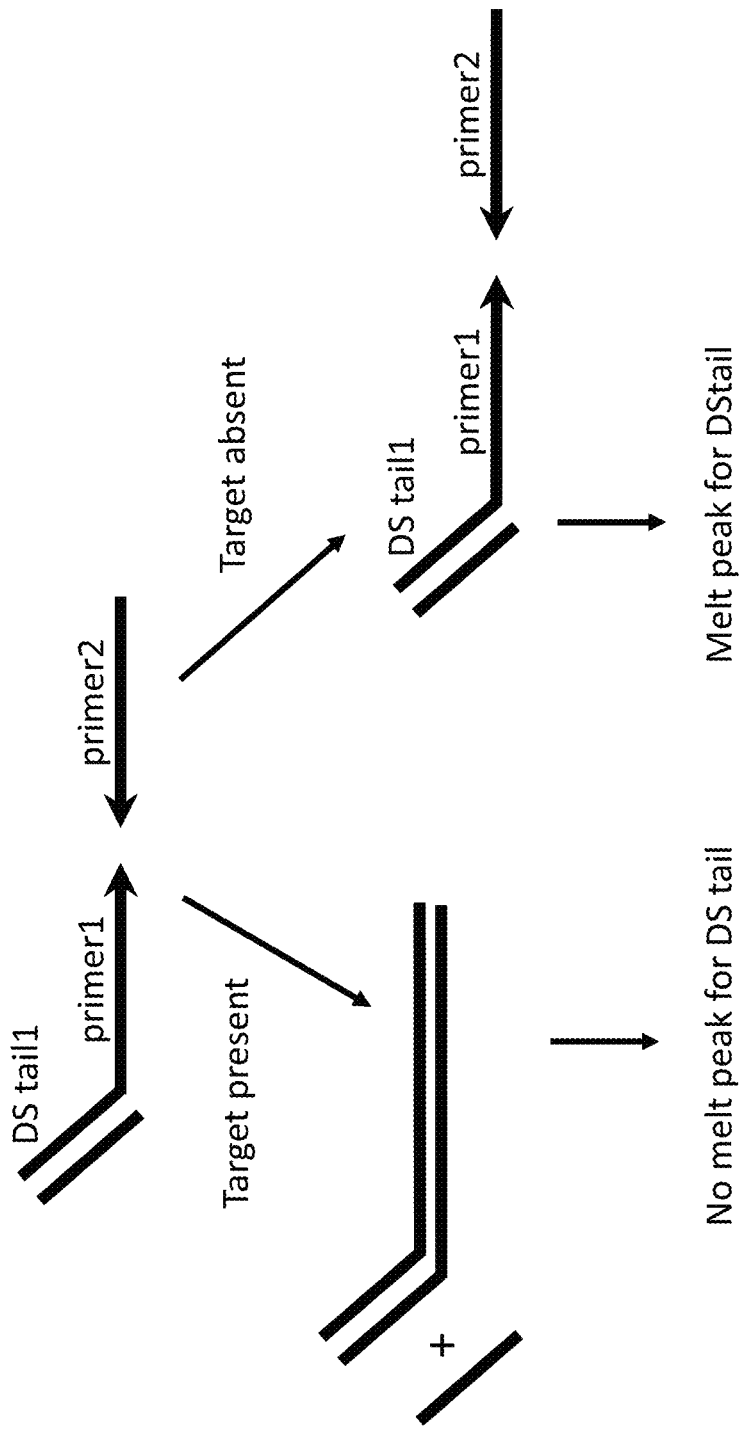
FIG. 37 shows a multiplex amplification reaction with double-stranded tailed underrepresented primers and a detection method with melt curve analysis.

The disclosed methods greatly reduce primer dimer formation and non-specific amplifications, thereby allowing use of double-stranded intercalating dyes to detect amplicons, which is very cost effective compared to the usage of fluorophore labeled oligonucleotides. These methods can be adapted to use melt curve analysis to differentiate between different amplicons based on their Tm. The presence and absence of a melt peak at a certain temperature determines the presence and absence of its corresponding amplicon. Preferably, 3 or 4 or 5 or 6 amplicons can be differentiated by their Tm ranging from 65° C. to 95° C. However, due to the nature of a regular amplicon, its Tm cannot be in the lower Tm range (i.e. 40° C.-65° C.). An artificial tail sequence with a Tm in the lower Tm range (40° C.-65° C.) is attached to the 5' end of one or more than one underrepresented primers (FIG. 37). One strand of the artificial tail sequence can have the same underrepresented nucleotide type(s) as the primer to which it is linked. Different underrepresented primers can have the same artificial tail or different artificial tails with different Tm. The complementary sequences of the artificial tails are also provided in the reaction so that they can form double strands. If the primer does not participate in the PCR reaction, it remains unchanged in the solution. After PCR, the double-stranded tail remains and shows a melt peak at its Tm during melting curve analysis. However, if the primer participate in PCR reactions, its extended products serve as templates for other primers to hybridize and extend, and becomes part of double strand amplicon. The double-stranded tail detaches and its corresponding melting peak in the low Tm range (40° C.-65° C.) disappears. Thus, as amplification proceeds there is a transition from the melting peak of primer tail(s) to that of amplification products incorporating such primers. Preferably, 3 or 4 or 5 or 6 types of the artificial tails with different Tm can be introduced to different underrepresented primers. The disappearance of one melting peak indicates the presence of the corresponding target. This method greatly increases multiplicity of the reaction with only one type of double-stranded intercalating dye. Instead of an artificial tail and a complementary strand, stem-loop structures can also be used to attach the underrepresented primers.

Combination of multi-channel fluorescence detection and Tm differentiation enables even higher multiplicity. A series of the artificial sequences with different Tm can be labeled with a fluorophore and their complementary sequences are labeled with a quencher. A second series of the artificial sequences can be labeled with another fluorophore and their complementary sequences labeled with another quencher. When the two series of sequences are attached to the 5' end of different underrepresented primers, the disappearance of a melting peak after amplification reaction in a fluorescence channel indicates the presence of corresponding target. The fluorophore and quencher can also be both labeled on the complementary sequences so that its fluorescence is at minimum level in single strand form and increases when it hybridizes to the artificial tails on the underrepresented primers. When stem-loop structures are used to attach underrepresented primers, fluorophore and quencher are labeled on the two ends of the stem-loop structures, in another word, one of the fluorophore and quencher is internally labeled on the primer. The Tm differences between double strands/stem-loops can be introduced by using different sequences or by using mismatch bases in one strand.

In another format of multi-channel melt curve analysis, an underrepresented primer is tailed on its 5' end by an artificial sequence. A fluorophore and quencher labeled oligonucleotide with the same sequence as the artificial tail is also provided. The complementary sequence of the artificial tail (or the fluorophore and quencher labeled oligo) is synthesized if the underrepresented primer participates in the reaction. During melt curve analysis after amplification reaction, the fluorophore and quencher labeled oligonucleotide hybridizes to the complementary sequence and dissociates when the temperature reaches its Tm. The oligonucleotide has a higher fluorescence signal when it duplexes with its complementary strand than the signal when it is in single strand form. Therefore a melt peak is observed. Preferably 2 or 3 or 4 or 5 or 6 melt peaks can be resolved in a temperature range in one fluorophore channel. The method can detect more targets in multi-channel format. The difference in Tm can be introduced by sequences with different base composition, sequences with different length, sequences with mismatches to its complementary strand, and the like.

The disclosed methods can be used to detect analytes other than nucleic acids, for instance, proteins or antibodies. An oligonucleotide template can be attached to an analyte. After separating the unbound oligonucleotide template, amplification of the oligonucleotide template with underrepresented primers indicates the presence of the analyte. Alternatively, underrepresented primers or probes can be attached to an analyte. The detection of the underrepresented primers or probes indicates the presence or absence of the analyte. For instance, after proximity ligation of underrepresented primers or probes attached to the analyte, detection of the ligated products indicates the presence or absence of the analyte.

FIGS. 32A and B show exemplary formats for immunoPCR in which the primers have one or more underrepresented nucleotide type(s). In FIG. 32A, antigens coated to solid surface are detected with antibodies attached by oligonucleotide which serve as realtime PCR template. Realtime PCR signal indicates the presence of antigen. The oligonucleotide can also be attached to secondary antibodies which bind primary antibodies. The assay can also be used in sandwich immunoassays. In FIG. 32B, antibodies specific to different epitopes on an antigen or multiple antibodies are attached to different oligonucleotides. When the antibodies bind antigen, oligonucleotides 1 and 2 are ligated with help of helper oligonucleotides. The ligation product serves as realtime PCR template for detection of antigens. Such assay can also be used for protein-protein interaction detection, where each protein binds with a specific antibody that is attached with an oligonucleotide. Protein-protein interactions result in proximity ligation of two oligonucleotides when then serves as realtime PCR template for detection.

FIG. 33 shows realtime PCR detection with energy transfer between fluorophores.

Primer 1 (or both primers) with underrepresented nucleotide type(s) is labeled with fluorophore 1 on its 5' end. For example, as shown in the figure, primer 1 is labeled on its 5' A. In PCR reaction, fluorophore 2 labeled dTTP is incorporated into product. Excitation of fluorophore 2 results in energy transfer from fluorophore 2 to fluorophore 1. Fluorophore 1 is then excited and signal is detected.

Figure 34:
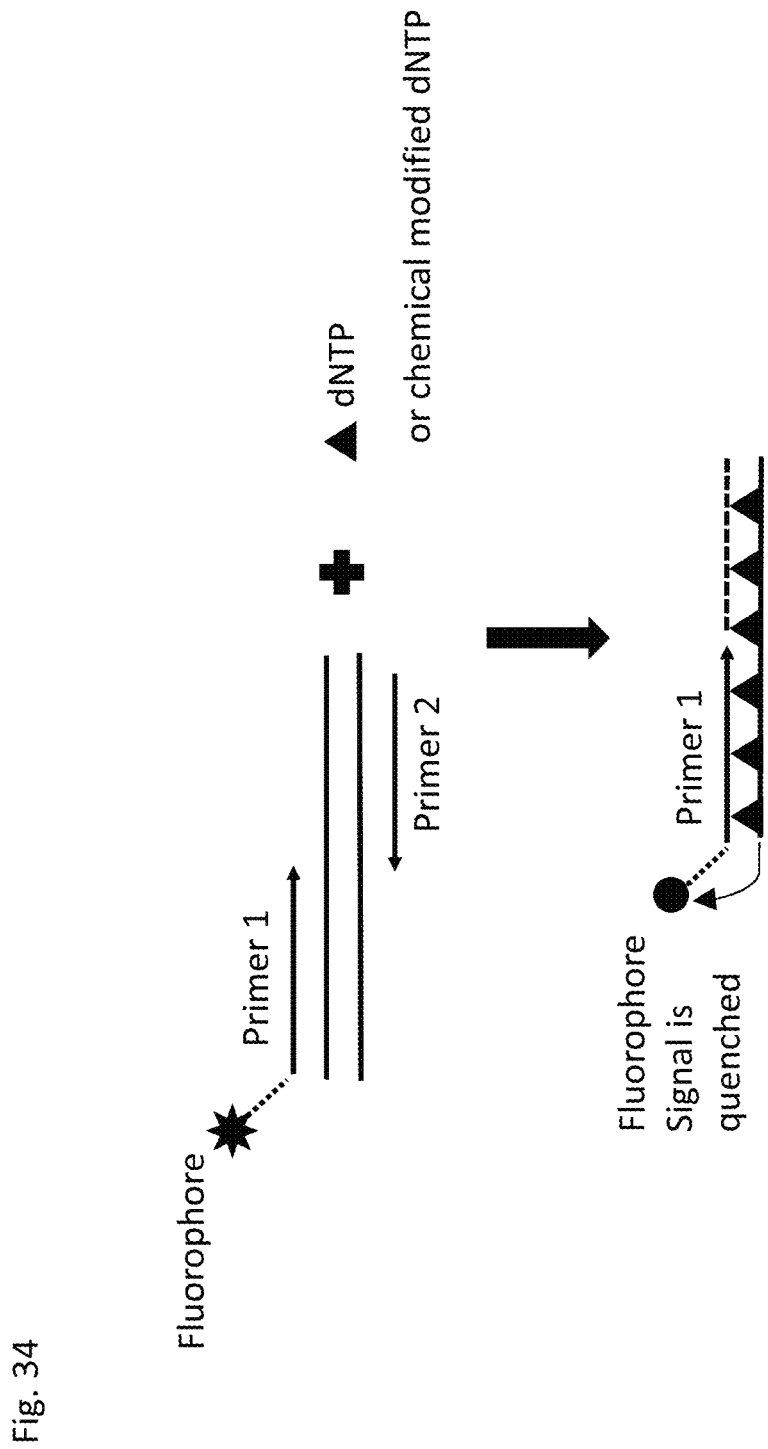
FIG. 34 shows an amplification reaction which a primer is labelled with a fluorophore and a nucleotide triphosphate used in amplification is labelled with a quencher. The signal from fluorophore is quenched as the amplification product is formed generating a signal.

FIG. 34 shows realtime PCR detection with a chemically modified dNTP. One or more primers with underrepresented nucleotides are labeled with fluorophores. One or more types of dNTPs are labeled with a double-stranded DNA intercalating chemical, or are modified such as deaza dGTP or deaza dATP. The labeled or modified dNTP intercalate into PCR product and fluorescence from primer is quenched. Signal drop indicates the presence of template. In another embodiment, modified dNTP can be used to selectively detect the signal from double-stranded DNA intercalating dyes. For example, deaza-G or deaza-A will quench SYBR™ Green signal in its proximity, therefore a regular PCR product that contains evenly distributed deaza-Gs is not detected by SYBR™ Green. The underrepresented primers can have artificial sequences at their 5' ends that don't contain complementary bases to the modified deoxynucleotide triphosphates. The synthesized complementary sequences of the artificial sequences in the 5' end will not contain the modified dNTP that will quench intercalating dye. For example when ATC primer is tailed on its 5' end by artificial sequence that contains no C, the PCR amplification products include two segments: a segment that contains deaza-G and a segment that contains no deaza-G. The intercalating dye SYBR™ Green fluorescence will be quenched by the deaza-G in the first segment and the SYBR™ Green fluorescence in the second segment will not be quenched.

Figure 35:
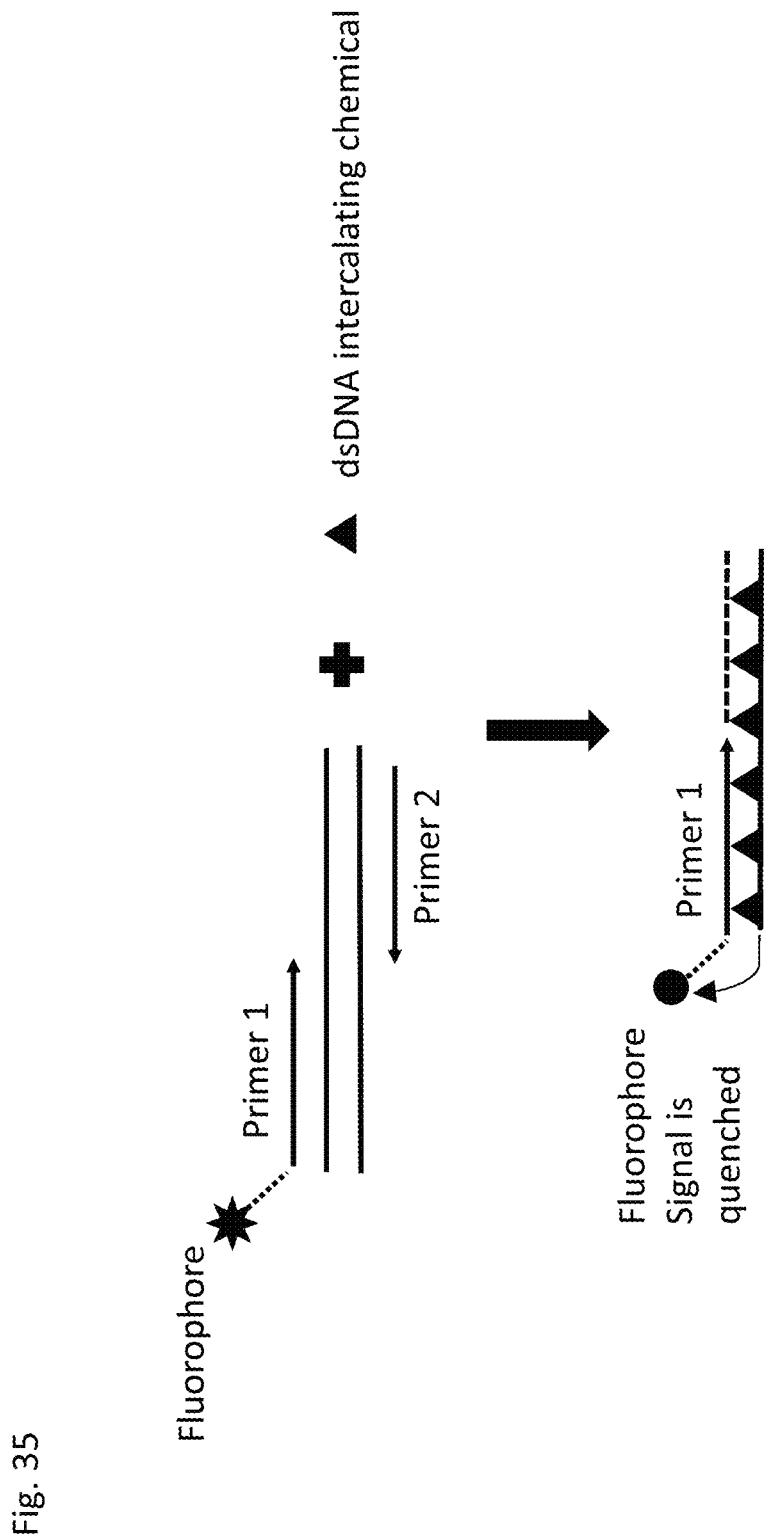
FIG. 35 shows an amplification reaction in which a primer is labelled with a fluorophore and a DNA intercalating agent is introduced into the amplification mix. Intercalation of the agent into the amplification product quenches the signal from the fluorophore as the amplification product is formed.

FIG. 35 shows realtime PCR detection with energy transfer between fluorophore and DNA intercalating chemicals. One or more primers with underrepresented nucleotides are labeled with fluorophore. A dsDNA intercalating chemical is added into PCR reaction. The chemical can be a fluorescence quencher which results in fluorescence signal drop when template is present. The chemical can also serve as energy transfer donor which excites the fluorophore on primers when template is present.

Figure 36:
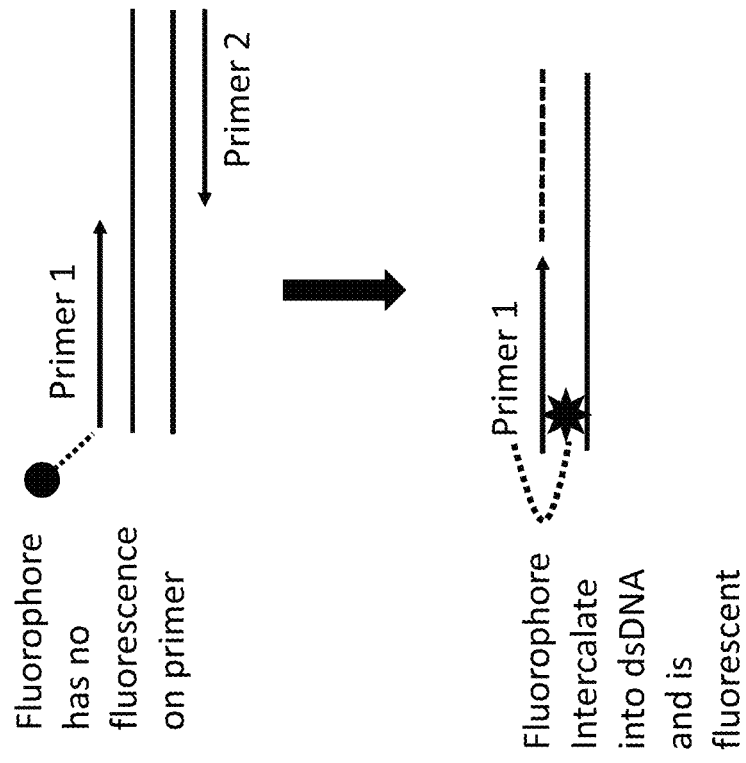
FIG. 36 shows an amplification reaction in which a primer is labelled with a light up fluorophore. Such a fluorophore has no signal in the primer, but when the primer is incorporated into am amplification product, the fluorophore intercalates into the amplification product and generates a signal.

FIG. 36 shows realtime PCR detection with a Lightup® fluorophore. One or more primers with underrepresented nucleotides are labeled with a Lightup® fluorophore. The fluorophore has no fluorescence when the primers are in single strand form. In PCR reaction, primers hybridize to templates and extend to form a double strand. The fluorophore then intercalates into the double-stranded DNA and fluorescence is detected.

For multiplex amplification with multiple pairs of underrepresented primers or probes, the amplification products may be detected with microarray, or sequences, or beads or nanobars. One of a pair underrepresented primers is grafted to a surface in conjunction with free primers in solution. These methods allow the simultaneous amplification and attachment of a PCR product onto the surface (Oroskar et al., 1996, *Clinical Chemistry*, 42(9), 1547-1555). Optionally both primers may be grafted to a surface for amplification. The underrepresented primers or probes attached to a surface may be coded or non-coded, or randomly distributed.

WO96/04404 (Mosaic Technologies, Inc. et al) discloses a method of detection of a target nucleic acid in a sample which potentially contains the target nucleic acid. The method involves the induction of a PCR based amplification of the target nucleic acid only when the target nucleic acid is present in the sample being tested. For the amplification of the target sequence, both primers are attached to a solid support, which results in the amplified target nucleic acid sequences also being attached to the solid support. The amplification technique disclosed in this document is sometimes referred to as the "bridge amplification" technique with the both forward and reverse underrepresented primers are attached on a support. In this technique the two underrepresented primers are, as for conventional PCR, specifically designed so that they flank the particular target DNA sequence to be amplified. Thus, if the particular target nucleic acid is present in the sample, the target nucleic acid can hybridize to the underrepresented primers and be amplified by PCR. The first step in this PCR amplification process is the hybridization of the target nucleic acid to the first specific underrepresented primer attached to the support ("primer 1"). A first amplification product, which is complementary to the target nucleic acid, is then formed by extension of the primer 1sequence. On subjecting the support to denaturation conditions the target nucleic acid is released and can then participate in further hybridization reactions with other primer 1 sequences which may be attached to the support. The first amplification product which is attached to the support, may then hybridize with the second specific underrepresented primer ("primer 2") attached to the support and a second amplification product comprising a nucleic acid sequence complementary to the first amplification product can be formed by extension of the primer 2 sequence and is also attached to the support. Thus, the target nucleic acid and the first and second amplification products are capable of participating in a plurality of hybridization and extension processes, limited only by the initial presence of the target nucleic acid and the number of primer 1 and primer 2 sequences initially present and the result is a number of copies of the target sequence attached to the surface.

Amplification products are only formed if the target nucleic acid is present. Therefore, monitoring the support for the presence or absence of one or more amplification products is indicative of the presence or absence of a specific target sequence.

The Mosaic technique can be used to achieve an amount of multiplexing in that several different target nucleic acid sequences can be amplified simultaneously by arraying different sets of first and second underrepresented primers as disclosed herein specific for each different target nucleic acid sequence, on different regions of the solid support.

h. Amplification of Products with a Sticky End

Figure 26:
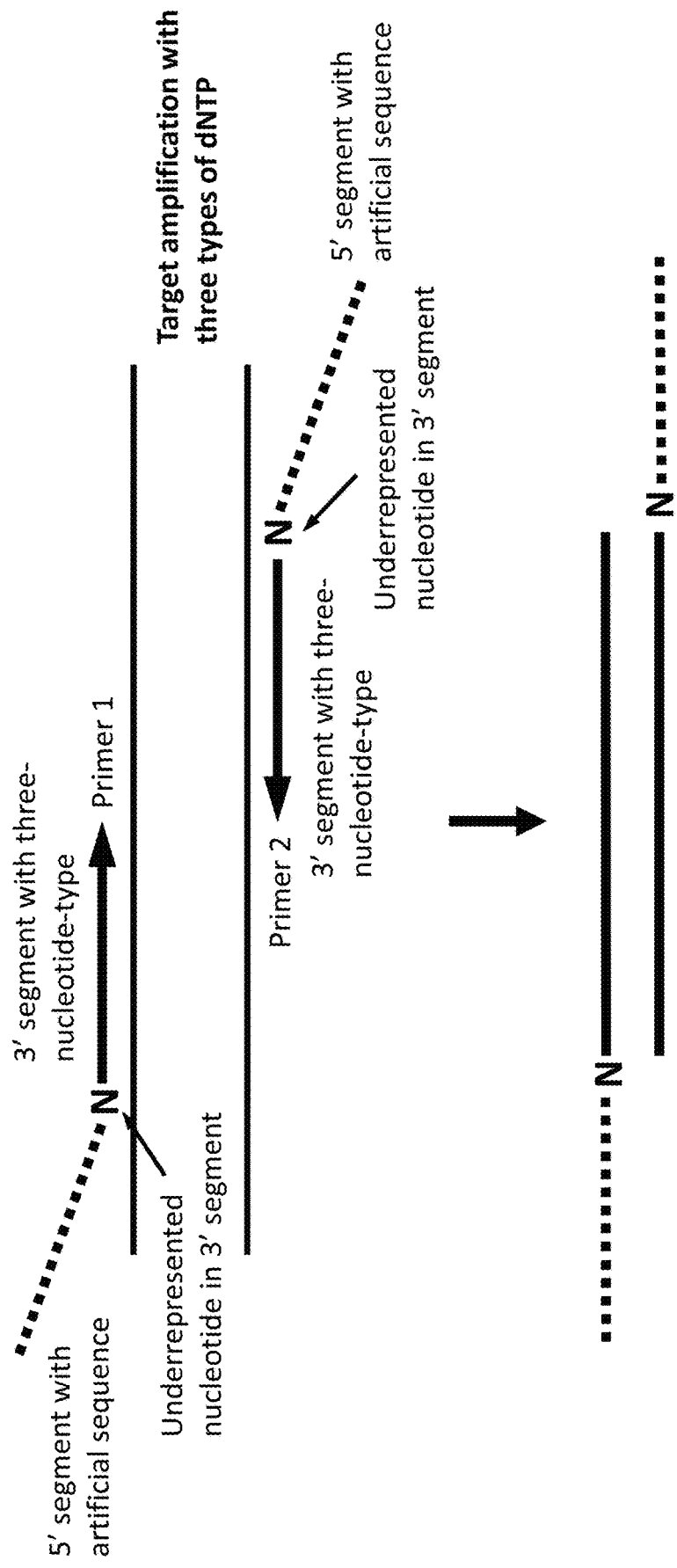
FIG. 26 Amplification and detection of sticky end products.

Conventionally a PCR product with a sticky end is produced with restriction sites tailed primers followed by restriction enzyme digestion, or the addition of an extra adenine on 3' end by the adenine transferase activity of Taq polymerase. Although the first approach gives desirable results, it requires extra steps, is time consuming, and is not always suitable to downstream applications. The second approach only produces short overhangs which have low efficiency for ligations. Disclosed in this invention as shown in FIG. 26, the underrepresented primers are linked at their 5' end with an artificial sequence and an underrepresented nucleotides located between the 5' end artificial sequence and the underrepresented primers. Depending on application, one or both underrepresented primers can be tailed with artificial sequences. When provided with only 3 nucleotide triphosphate monomers omitting the complement of the underrepresented nucleotide, primer extensions stops at the position of the underrepresented nucleotide in the primer. Amplification results in products with 5' overhang on one side or both sides. The free choice of sequence and length of the artificial tail allows various applications, such as cloning, hybridization with single strand DNA on solid surface, ligation with adapters, and so forth.

i. Smrt™-Bell Primers for a Circular Amplification Product

Figure 27:
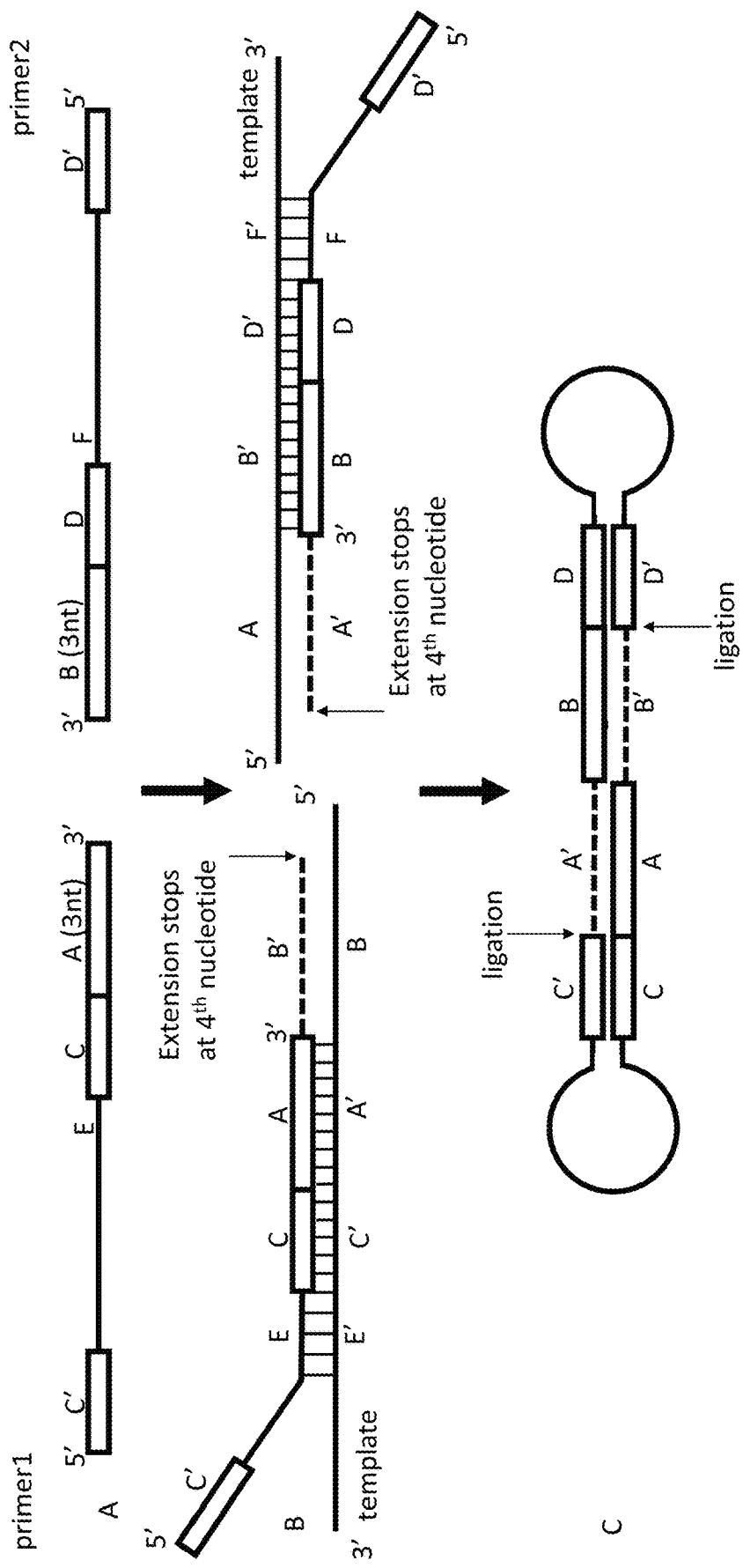
FIG. 27 amplification and detection of circular products.

The methods can also be performed with primers linked to hairpin loops forming bell-shaped primers useful for generating circular products for next generation sequencing as shown in FIGS. 26 and 27. Forward and reverse primers with an underrepresented nucleotide type are each linked at the 5' end to one arm of a hairpin primer (which can have any nucleotide composition). The 5' most nucleotide of the primer is the complement of the underrepresented nucleotide. The two primers hybridize to contiguous binding sites on the target nucleic acid or binding sites that are non-contiguous but free of the underrepresented nucleotide type. Both primers are extended in an amplification mix lacking the complement of the underrepresented nucleotide. Extension stops when the nucleotide triphosphate of complement of the underrepresented nucleotide is needed to incorporate. The extended strands of two primers hybridize with each other leaving a circular structure with nicks between the 3' end of one primer and the 5' of the other primer. The nicks are sealed with ligase generating a circular product, which can serve as a template for SMRT™Bell sequencing. The process is shown in more detail in FIGS. 27A-C. FIG. 27A shows a first primer includes a target binding region A with an underrepresented nucleotide linked to a hairpin with complementary stem regions C which is also a target binding region and C' and a loop E 3' of which is a target binding region. The reverse primer has a target binding region B with an underrepresented nucleotide type linked to hairpin loop with segments D which is also a target binding region and D' forming the stem and a loop F 3' of which is a target binding region. In this configuration segments A, C and part of E in the forward primer bind to the template as to segments B, D and part of F in the reverse primer. FIG. 27B shows both primers anneal to templates. The ACE sequences of primer 1 hybridize to the A'C'E' sequences of templates and extend B' sequence. BDF sequences of primer 2 hybridize to B'D'F; sequences of templates and extend A' sequence. Extension stops when the non-provided nucleotide is needed. FIG. 27C shows the two extension products from step B form hairpin structures and hybridize to each other at the A'B or AB' regions. The nicks at arrows are ligated. A circular product is generated. Non-circular oligonucleotides in the system can be digested with exonuclease. Alternatively, the underrepresented primer may have a stem loop structure at 5' end segment. When both such kinds of underrepresented primers are used in amplification using non-strand displacement polymerase in the amplification system, the amplified product can be ligated to form a circular product with ligase. Non-circular oligonucleotides in the system can be digested with an exonuclease. The stem loop sequence at 5' end segment may be the same or different for both underrepresented primers. The ligated circular products can be cut with different chemicals or enzymes to linearize the circular products for downstream application. The disclosed invention methods can be used for second generation sequence library preparation.

i. Primers Underrepresented in More than One Nucleotide Type

The strategy and principles for primers with a single underrepresented nucleotide type can be applied to primers or with two or even three underrepresented nucleotides can be applied to primers (or in other words consisting entirely or primarily of a single nucleotide). Use of primers underrepresented in a single nucleotide has wider applicability in natural target nucleic acids because binding sites for such primers occur at statistically greater frequency. However, some forms of amplification, such as immune-PCR, amplify nucleic acids of artificial sequences. Such artificial sequences can be designed to be amplified with primers with two or even three underrepresented nucleotide type as with one underrepresented nucleotide type.

In primers underrepresented in two nucleotide types, the two underrepresented nucleotide types should not be complementary to one another. In others words, the underrepresented nucleotide types can be A with C, A with G, T/U with C or T/U with G. This leaves primers consisting entirely or primarily of the same two noncomplementary nucleotide types. Such primers have reduced ability to support primer-dimer or primer-mismatch extension. Primers have three nucleotides underrepresented or in other words, consisting entirely or substantially of a single nucleotide type also have reduced ability to support primer dimer or mismatched primer extension. Primer binding sites are selected by analogous principles to those described above, and primer sequences can be adjusted to accommodate a small number of underrepresented nucleotide(s) if necessary. Toehold and junction primer strategies can also be used. Amplification with such primers is performed at least with the complements of the nucleotides not underrepresented in the primers, and optionally, with the complements of the underrepresented nucleotide(s) as well, which as noted can be supplied in reduced concentration or as dideoxy nucleotides.

j. Amplification Methods

The strategy and principles described above can be incorporated into any amplification method involving template-directed extension from single or paired primers. The polymerase chain reaction is one implementation including optionally RT-PCR. PCR is characterized by temperature cycling to permit primer annealing, primer extension and denaturation of an extended strand from its template.

Figure 29:
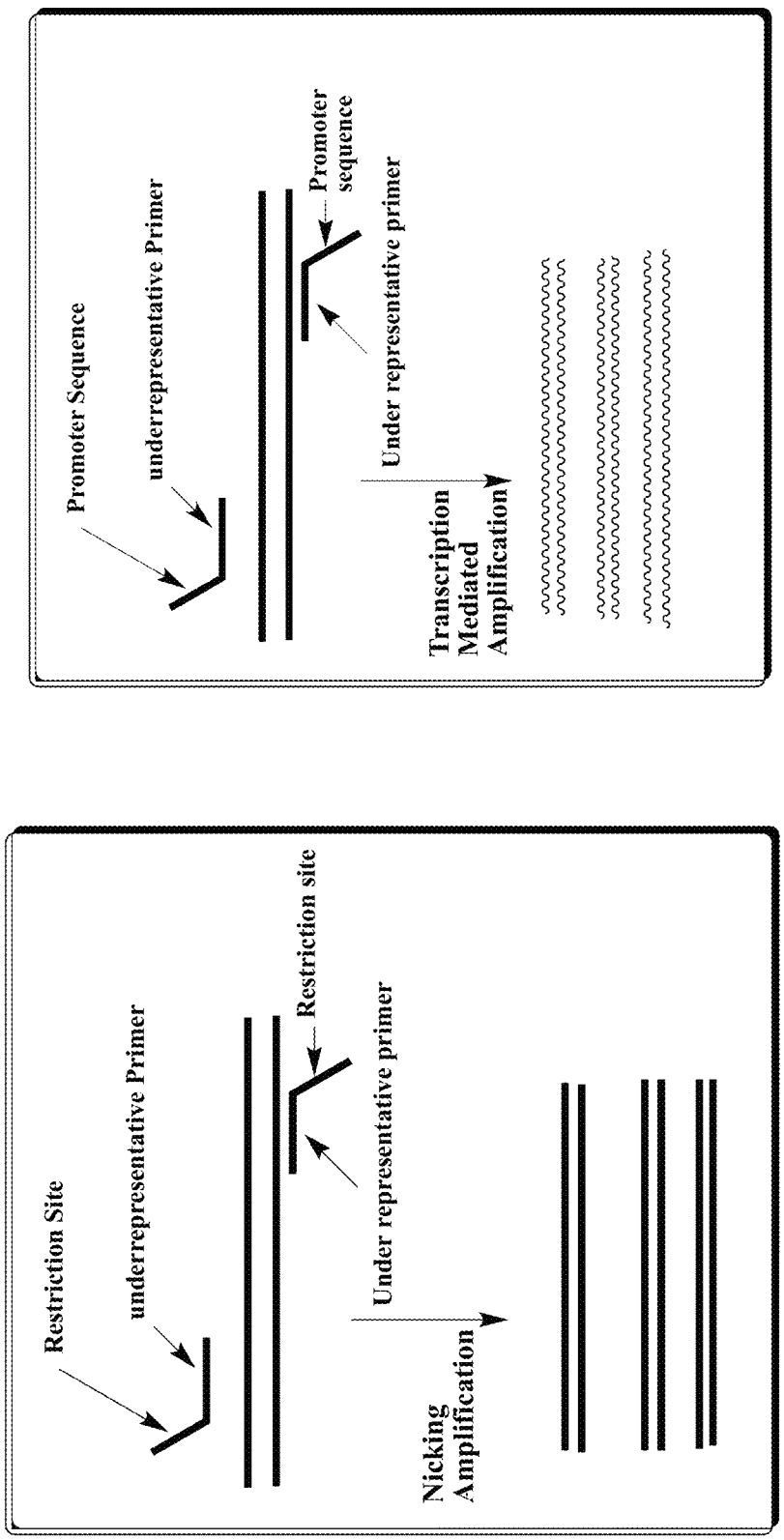
FIG. 29 Use of three nucleotide primers in combination with nicking amplification or transcription mediated amplification.

Transcription mediated amplification (TMA) is an alternative isothermal form in which one or both of the primers is linked to a promoter at its 5' end, usually a T7 promoter, as shown in FIG. 29B. FIG. 29B shows two three nucleotide-type primers tailed with promoter sequences for an RNA polymerase. Once the double-stranded promoter is formed, the RNA polymerase starts transcription amplification. The amplification product is single stranded RNA molecules. TMA can also be coupled to reverse transcription.

Another isothermal amplification format amenable to use with primers of the invention is the nicking amplification reaction (NEAR). NEAR exponentially amplifies DNA at a constant temperature using a polymerase and nicking enzyme. The primers for nicking amplification are linked to artificial segments at their 5' ends, the 5' segments containing a cleavage site for the nicking enzyme (as shown in FIG. 29A). In the first cycle both primers hybridize to a template and extend. In the next cycle, both primers can hybridizes to the first cycle products and extend to generate the full nicking site on the artificial tail. Once a nicking site is formed, nicking enzyme nicks and releases one strand. Extension and nicking repeat in the next cycle.

Another isothermal amplification procedure amenable to use with primers of the invention is loop mediated isothermal amplification or (LAMP). LAMP uses one or more primers having underrepresented nucleotides in accordance with the invention. (FIG. 30, left panel). In LAMP, the target sequence is amplified at a constant temperature of 60-65° C. using either two or three sets of primers and a polymerase with high strand displacement activity in addition to a replication activity. Typically, 4 different primers are used to identify 6 distinct regions on the target gene, which adds highly to the specificity. An additional pair of "loop primers" can further accelerate the reaction.

Another isothermal amplification format is Recombinase Polymerase Amplification (RPA) is a single tube, isothermal alternative to the Polymerase Chain Reaction (PCR) (FIG. 30 right). The RPA process employs three core enzymes—a recombinase, a single-stranded DNA-binding protein (SSB) and strand-displacing polymerase. Recombinases are capable of pairing oligonucleotide primers with homologous sequence in duplex DNA. SSB bind to displaced strands of DNA and prevent the primers from being displaced. Finally, the strand displacing polymerase begins DNA synthesis where the primer has bound to the target DNA. By using two opposing primers, much like PCR, if the target sequence is indeed present, an exponential DNA amplification reaction is initiated. The two primers can both be primers with underrepresented nucleotide types as described above.

Still other amplification format in which primers of the invention can be used include strand displacement assay, transcription-based amplification systems, self-sustained sequence replication (3SR), a ligation chain reaction (sometimes referred to as oligonucleotide ligase amplification OLA), cycling probe technology (CPT), rolling circle amplification (RCA), nucleic acid sequence bases amplification (NASBA), invasive cleavage technology, Helicase dependent amplification (HDA), Exponential amplification (EX-PAR), Hybridization chain reaction (HCR), and catalyzed hairpin assembly (CHA).

Another amplification format is immune-PCR in which an analyte is linked to a nucleic acid (which can have an artificial sequence) and the analyte is detected by amplification of the nucleic acid. Such amplification can be performed with a primer pair with underrepresented nucleotide types (e.g., completely absent) complementary to primer binding sites underrepresented in the complements of the underrepresented nucleotide(s).

The above methods amplify a specific predetermined target nucleic acid or segment thereof determined by the selected primers and their complementary primer binding sites (in other words, target-specific amplification). The amplification product from a pair of primers binding to its intended primer binding sites predominates over any or all other amplification products primed from the same primer pair either by primer dimer binding or mispriming on the target sequence. Optionally, the amplified segment constitutes at least 99% of all amplification products formed by extension of the forward and reverse primers. Preferably the amplification product from primers binding to their intended primer binding sites is present in at least 10, 50, 100 or 1000 fold excess (by moles, mass or copy number) of any or all other amplification products primed from the primer pair. In some methods, a single pair of primers is used in amplification. In other methods, multiple primer pairs are used in a multiplex amplification. The number of primer pairs can be for example 2-50 or more, preferably 5-25 or 10-20, or at least 2, 3, 4, 5, 6, 7, 8, 9, 10, 11, 12, 13, 14, 15, 16, 17, 18, 19 or 20. When multiple primer pairs are used the intended amplification product of each primer pair from binding of the primer pair to its intended primer binding sites is present in at least 10, 50, 100 or 1000 fold excess (by moles, mass or copy number) to any or all other amplification products primed by that primer pair. Except in the random priming format described below, primers used in the methods are not random primers in which most or all primer positions are occupied by random or degenerate selections of nucleotides varying among primers. Rather each primer pair is designed to hybridize to specific primer binding sites in a target nucleic acid, and typically different primer pairs are unrelated from each other as required by the different primer binding sites in target nucleic acids being detected. For example, one primer pair can be designed to bind to primer binding sites on a target nucleic acid in one pathogen and a second primer pair to primer binding sites on a different target nucleic acid in a different pathogen. Except by coincidence the different target nucleic acids and consequently primer binding sites and primers are unrelated to one another.

III. Random Priming with Degenerate Primers

Figure 28:
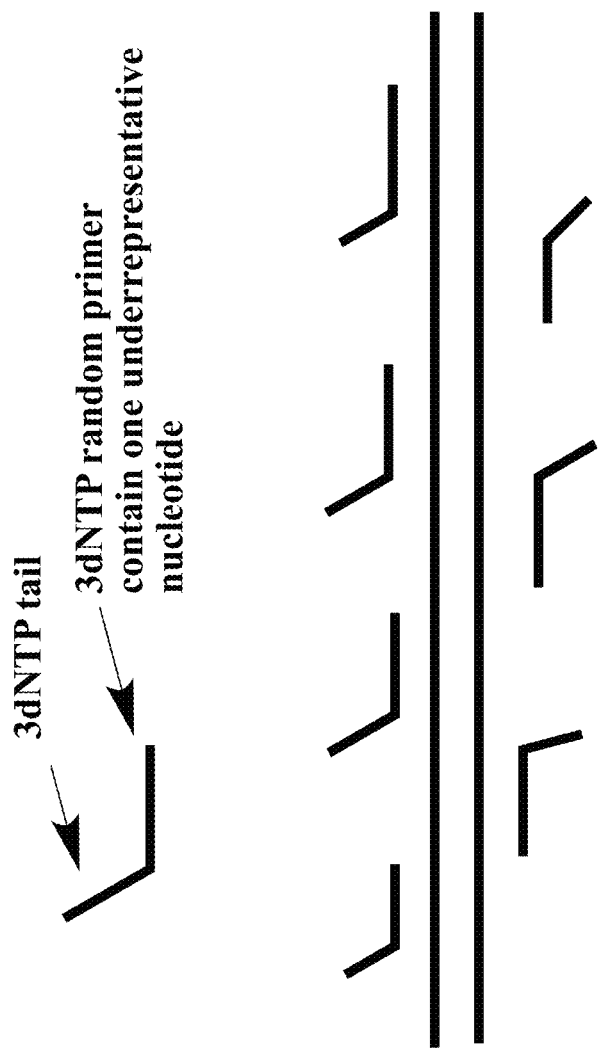
FIG. 28 whole genome amplification with three nucleotide-type primers.

The invention further provides methods of random priming amplification with degenerate underrepresented primers-called underrepresented degenerate primers. Such methods employ primers with a 3' hybridization segment which randomly varies among primers (as shown in FIG. 28) linked to a 5' artificial segment, which is the same in different primers. The 5' artificial segment consists of only three types of nucleotide with the possible exception of an underrepresented nucleotide at the 5' end and the 3' hybridization segment consists of the same three types of nucleotides. In another embodiment, the 3' segment also consists of the same three types of nucleotides except that it can also include limited number of units of the fourth nucleotide type at positions except at the 3' end. The limited number of units of the fourth nucleotide type (G) present in the 3' random segment are more than 1%, but less than 20%. Usually no more than 1, 2 or 3 such nucleotides are present in the 3' random segment. Including limited number of units of the underrepresented nucleotide type in the 3' segment significantly increases the diversity of random primers without significantly increasing unintended random primer interactions. In another embodiment, underrepresented degenerate primers may include unnatural nucleotides, such as inosine, nitroindole, as long as unnatural nucleotides included in the underrepresented primers may help to reduce primer interaction comparing to traditional A, T, G, C primers. The unnatural nucleotides can be included in the 5' artificial segment or in the 3' random hybridization segment, or included in both 5' artificial segment and 3' random hybridization segment. An example of the 3' hybridization segment consists of A, T, C and a fourth unnatural nucleotide inosine can be included in random position. In such case, the 3' random hybridization segment consists of A, T, C and I four nucleotides. In another embodiment, the unnatural nucleotides can be included also as underrepresented in the degenerated underrepresented primers. An example of A, T, C degenerate underrepresented primers can include inosine with the amount between 0.1% and 25%. The disclosed invention may include one or two step amplifications: an initial amplification performed with each of the four nucleotide triphosphate monomers generates primary amplification products flanked by the 5' artificial segment and its complement. A secondary amplification is then performed with primers with 3' segment which is complementary to the complement of the 5' artificial segment of the random primers. Such methods are particularly useful for amplifying large regions of DNA, such as BACS, YACS, whole chromosomes or whole genomes or single cell amplification. Amplified product can be detected by addition of SYBR™ green or by fluorescence labeled probes among other methods. Primers used in secondary amplification can have 5' tails for other applications such as sequencing library preparation, single cell amplification among others. Amplification can be by PCR or isothermal methods disclosed herein.

IV. Extension Reactions

The principles of primer design discussed above can also be used for primers used for extension reactions, such as single-base extension in which a primer hybridizes adjacent to but not spanning a mutation, such as a SNP, or allele specific extension in which a primer hybridizes across a site of mutation. In reactions involving extension from a single primer, primer-primer dimerization is not a concern but mismatched binding of a primer to a target nucleic acid (or non-target nucleic acid) is a concern, and primer-dimer problems can also arise in multiplex extension.

V. Mutation Detection

The present invention may be used for detecting a mutation in target nucleic acids indicative of genomic instability. For example, methods of mutation detection are useful to detect and/or to identify mutations or other alterations associated with diseases, such as cancer and other pathological genetic conditions, disorders or syndromes. Such mutations include nucleotide insertions, deletions, rearrangements, transitions, translations, tranversions, polymorphisms, and substitutions. More specifically, mutations can include single nucleotide polymorphisms (SNP's). The present invention can be used to identify the presence or absence of mutations. Generally, mutations can include any change in the target nucleic acid, such as a loss of heterozygosity or other indicia of genomic instability.

Generally, methods for detecting a mutation in a target nucleic acid include hybridization-based assay or exposing a target nucleic acid template suspected to contain a mutation to an underrepresented primer that is capable of hybridizing to a known region proximate to the suspected mutation. The underrepresented primer is extended and one or more complementary nucleotides are hybridized through the site suspected to contain the mutation. The presence or absence of a mutation is determined by analyzing the nucleotides that are incorporated or not incorporated into the underrepresented primer. In one format, one or more underrepresented primers contain 7-deaza-2'-deoxyguanosine and/or 7-deaza-2'-deoxyadenosine at 3' end. The unnatural nucleotides at 3' end further inhibit or facilitate amplification on templates to detect mutations.

Many mutation detection methods reported in literature can use current invention to improve detection accuracy. For instance, SNPs detection is performed using two main methods, the traditional and high throughput methods. The traditional gel-based approach uses standard molecular techniques, such as amplification refractory mutation system (ARMS), restriction digests and various forms of gel electrophoresis (e.g., RFLP), denaturing gradient gel electrophoresis (DGGE) and single-strand conformation polymorphism (SSCP). High throughput methods include allele discrimination methods (Allele-Specific Hybridization, Allele-Specific Single-BasePrimer Extension), Padlock probe, Molecular inversion probe (MIP), High-throughput assay chemistry (Flap endonuclease discrimination, Oligonucleotide ligation), DNA arrays, pyrosequencing, second generation sequencing, and light cycler.

VI. Computer Implementation

Selection of primer binding sites and primers can be performed by computer-implemented analysis of a target nucleic acid in a computer programmed by non-transitory computer readable storage media. The sequence of a target nucleic acid (one or both strands) is received in a computer. The computer also stores or receives by user input desired nucleotide compositions of primers (e.g., A, T, C). The computer is then programmed to search the target sequence to identify forward and reverse primer binding sites within a distance of one another compatible with amplification that most closely correspond to the primer composition. If the primer composition is A, T, C, then forward and reverse primer binding sites should most closely correspond to A, T and G. The computer can identify forward and reverse primer binding sites on opposite strands or can identify a complement of the forward primer binding sites and reverse primer binding site on the same strand and calculate the forward primer binding site from its complement. The computer can then provide output of candidate pairs of primer binding sites, which may differ to varying degrees with the ideal composition sought. The computer can also show primer designs that hybridize to each of the primer binding site pairs. Multiple primer designs can be shown for the same primer binding site pair with different numbers of units of the underrepresented nucleotide and different numbers of mismatches.

A computer system can include a bus which interconnects major subsystems such as a central processor, a system memory, an input/output controller, an external device such as a printer via a parallel port, a display screen via a display adapter, a serial port, a keyboard, a fixed disk drive, and an internet connection. Many other devices can be connected such as a scanner via I/O controller, a mouse connected to serial port or a network interface. Many other devices or subsystems may be connected in a similar manner. Also, it is not necessary for all of the devices to be present to practice the present invention, as discussed below. The devices and subsystems may be interconnected in different ways. Source code to implement the present invention may be operably disposed in system memory or stored on storage media such as a fixed disk, compact disk or the like. The computer system can be a mainframe, PC, table or cell phone among other possibilities.

VII. Method and Kits for Application

Any of the disclosed primers and probes can be incorporated into kits. Such a kit preferably includes at least one primer pair and preferably at least 5, 20 or 20 primer pairs.

The primer pairs in a kit are preferably capable of use in the same multiplex reaction meaning that they have compatible melting temperatures as well as the same underrepresented nucleotide type(s). Any other reagents disclosed as being used with such primers and probes can be included in such kits including NTPs for inclusion in amplification reactions, mismatch stabilizing agents, fluorophores or other labels. Kits can also include instructions detailing how to use the kit in any of the disclosed methods.

The disclosed invention provides kits for the detection and identification of microorganisms, e.g., pathogens infecting mammals. Thus, the invention can be used, e.g., to identify the particular strain of a virus that is infecting a human subject, e.g., the particular strain of human immunodeficiency virus, or papilloma virus (HPV), among others. Strains of microorganisms often differ from each other in a few nucleotides, whereas the remaining of their genomes is identical. Thus, probes can be made to recognize the conserved regions and to identify the particular variable nucleotide(s).

For example, a wide variety of infectious diseases can be detected by the process of the present invention. Typically, these are caused by bacterial, viral, parasite, and fungal infectious agents. The resistance of various infectious agents to drugs can also be determined using the present invention.

The present invention is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia. Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected by the process of the present invention generally involve oncogenes, tumor suppressor genes, or genes involved in DNA amplification, replication, recombination, or repair. Examples of these include: BRCA1 gene, p53 gene, APC gene, Her2/Neu amplification, Bcr/AB1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can be used for sequencing library preparation for NGS, single cell amplification and detection such as RNA-seq, prenatal detection such as down syndrome, and so forth.

The present invention can also be used in a variety of forensic areas, including for human identification for military personnel and criminal investigation, paternity testing and family relation analysis, HLA compatibility typing, Short Tandom Repeats (STR) and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, and so forth. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections and in animal breeding programs.

Although the invention has been described in detail for purposes of clarity of understanding, certain modifications may be practiced within the scope of the appended claims. All publications including accession numbers, websites and the like, and patent documents cited in this application are hereby incorporated by reference in their entirety for all purposes to the same extent as if each were so individually denoted. To the extent difference version of a sequence, website or other reference may be present at different times, the version associated with the reference at the effective filing date is meant. The effective filing date means the earliest priority date at which the accession number at issue is disclosed. Unless otherwise apparent from the context any element, embodiment, step, feature or aspect of the invention can be performed in combination with any other.

EXAMPLES

Examples 1 and 2: Transient Interactions in Conventional Primers and Three Nucleotides Primers Although primer dimer formation is not fully understood, it is clear that primer interaction is responsible for unintended amplification products. In theory, with the help of computation, conventional four nucleotides primers can be very carefully designed to avoid secondary structures and primer-primer interactions. Such computations work well for single pair of primers but less so for multiplexes.

We designed a set of four nucleotide primers (regular primer 1-32) by theoretical computation. In multiplex with 32 primers, we found extremely high level of primer-primer interactions. A set of three-nucleotide-type primers with random sequences was also multiplexed. Primer interactions were much lower in the three-nucleotide-type primer multiplex.

We used SYBR™ Green to detect any primer-primer interaction formed in the reaction. A 25 ul reaction contained 10 mM Tris-HCl (pH8.3), 50 mM KCl (1:10 dilution of AmpliTaq™ Gold PCR buffer II, Life Technologies), 2 mM MgCl2 (1:12.5 dilution of 25 mM stock MgCl2 solution, Life Technologies), 0.2 mM each dNTP (1:12.5 diluted from 2.5 mM each dNTPs solution, which was prepared from 100 mM stock dNTP solutions, Life Technologies), and 1× SYBR™ green 11 (1:100 dilution from 100× stock solution, which was prepared from 10000× stock solution, Sigma-Aldrich). Thirty-two four-nucleotide-type primers or three-nucleotide-type primers (IDTDNA) were added to final concentrations of 2.6 uM, 5.2 uM, 13 uM, 26 uM, 39 uM, and 52 uM. The reactions were heated to 95 C for 2 min, and cooled to 65 C for signal detection.

FIG. 2A shows four-nucleotide-type primer interactions. When no primers were present (0 uM), the fluorescence signal was zero. 2.6 uM shows a fluorescence signal at ca. 100 k. 5.2 uM shows a fluorescence signal at ca. 150 k-180 k. 13.1 uM shows a fluorescence signal at ca. 250 k-300 k. 26 uM and 39 uM show fluorescence signal at ca. 300 k-350 k.

FIG. 2B shows three-nucleotide-type primer interactions. 2.6 uM, 5.2 uM, and 13 uM concentrations of primers only showed minimal fluorescence level of less than 10 k. 26 uM, 39 uM, and 52 uM concentrations showed gradually increase fluorescence from ca. 12.5 k to ca. 25 k.

Example 3: Four Nucleotide and Three Nucleotide Primer Dimer Formation in PCR Reactions As shown in example 2, primer-primer interactions are at extremely high level for four-nucleotide-type primers and are at very low level for three-nucleotide-type primers. Therefore, in PCR reactions, three-nucleotide-type primers should have a much lower primer-dimer formation. We multiplexed the same sets of primers used in previous example in PCR reactions.

For three nucleotide primers, a 25 ul PCR reaction contained 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.875 u of AmpliTaq™ Gold DNA polymerase (Life Technologies). For four nucleotide primers, 0.2 mM dCTP is also added. Both three nucleotides primers and regular four nucleotides primers are added to a total concentration of 2.6 uM. PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds). Both reactions were repeated for 48 times.

FIG. 3A shows three-nucleotide-type primer dimer formation. Only 2 of 48 repeats had primer dimer at 50 and 55 cycles. FIG. 3B shows four-nucleotide-type primer dimer formation. All 48 reactions consistently had primer dimers before 30 cycles.

Example 4: Real Time PCR Reaction with Three-Nucleotide-Type Primers and Three-Nucleotide-Type dNTPs Three-nucleotide-type primers with mismatches were designed to detect human genomic DNA.

A 25 ul PCR reaction contained 100 ng human genomic DNA (NEB), 10 mM Tris-HCl (pH8.3), 50 mM KCl, 2 mM MgCl2, 0.2 mM dATP, 0.2 mM dTTP, 0.2 mM dGTP, 1×SYBR™ green II, 0.8 mM each primer (Hemo2F, Hemo2R), 1.25 u of AmpliTaq™ Gold DNA polymerase. A no-template control reaction contained no human genomic DNA. PCR cycling was carried out on StepOne™ Real-Time PCR System (Life Technologies). Cycling conditions were as following: 95° C. 10 minutes, 60 cycles of (95° C. 15 seconds, 60° C. 15 seconds). The fluorescence signal was recorded at annealing step.

FIG. 4A shows fluorescence over time for PCR reaction with human genomic DNA as a template. FIG. 4B shows fluorescence over time for PCR reaction of a no template control.

100 ng human genomic DNA was readily detected with three-nucleotide-type primer real time PCR. When no template was present, no primer dimers formed.

Example 5: Real Time PCR and End Point Detection with Three-Nucleotide-Type Primers and 4 Nucleotides dNTPs In this example, three-nucleotide-type primers were used in the same way as conventional four-nucleotide-type primers would be. Two sets of primers were tested for detection of HPV11. HPV11-1F and HPV11-1R had no mismatches, HPV11MM1F had mismatches at position 12 and 18, and HPV11MM1R had mismatches at position 11 and 22.

The HPV template was diluted to $10^5$ (1 pg), $10^4$ (100 fg), $10^3$ (10 fg), $10^2$ (0.1 fg), $10^1$ (0.01 fg) copies/ul. A 25 ul PCR reaction contained 1 ul template, 10 mM Tris-HCl (pH8.3), 50 mM KCl, 2 mM MgCl2, 0.2 mM each dATP, dTTP, and dGTP, 1×SYBR™ green II, 0.8 mM each primer, 1.25 u of AmpliTaq™ Gold DNA polymerase. PCR cycling was carried out on StepOne™ Real-Time PCR System. Cycling conditions were as following: 95° C. 10 minutes, 60 cycles of (95° C. 15 seconds, 60° C. 15 seconds). Fluorescence signal was recorded at annealing step. After 60 cycles, 6×DNA loading dye was added and 10 ul samples were loaded onto 0.8% agarose gel.

FIGS. 8A, B show fluorescence over time for all templates including $H_2O$ for a no template control. As few as 10 copies of HPV template could be readily detected, whereas the no template control had no amplification over 60 cycles. FIG. 8C shows a gel electrophoresis image of amplification products. All templates were amplified with correct size products regardless of presence of mismatch in primer sequences.

Example 6: Three-Nucleotide-Type Primer with 5' G

The hybridization region of three-nucleotide-type primers on template is usually flanked by a C on its 3' end. Otherwise when it is an A T or G, more bases could be included in the primer consistent with the limited composition. In this example, we designed a three-nucleotide-type primer with a G on its 5' end to match with the 3' C on template. Such primers have higher Tm and improved hybridization efficiency.

Addition of a G on the 5' end potentially enables pairing of C of same primer or different primer. However, such a pairing has no effect on primer dimer formation because no extension can occur on the 5' end. In some extreme cases, when primer dimers form, the unintended extension product ends with a C on its 3' end as other primers. The 3' C prevents further extension when this product interacts with other primers because the 3' C cannot pair with any other bases on the primers.

Example 7: Mismatch Binding Reagents Stabilize Primer Template Hybridization

Amplifications can be performed with primers with mismatches. When more mismatches are introduced into primers, primer-template hybridization is less efficient. In this example, mismatch binding reagents are added into reaction to stabilize primer-template hybridization and increase amplification efficiency.

To test the effect of mismatch binding reagent on primer-template hybridization, pairs of synthetic oligonucleotides with various degrees of mismatches are mixed with mismatch binding reagent. Typically oligonucleotides are provided at 0.1-1 uM in the presence of 10 mM Tris-HCl (pH8.3), 50 mM KCl, 2 mM MgCl2, 0.2 mM dATP, 0.2 mM dTTP, 0.2 mM dGTP, 1x SYBR™ green II. Mismatch binding reagent is provided in 0x, 0.001x, 0.01x, 0.1x, or 1x concentration of the oligos. Melting curve analysis is conducted as following condition: mixture is heated to 95° C. for 1 minute to completely denature two oligos; mixture is then cooled slowly down to desired temperature modified according to theoretical melting temperature of the two oligos, e.g. 10-20 degrees below the melting temperature of one oligonucleotide assuming no mismatch; mixture is then heated by 0.1-0.3° C. per step, fluorescence signal is collected each step. Melting curves of oligonucleotides with various degree of mismatch and various amount of mismatch binding reagent are plotted and melting temperatures are calculated. The mismatch binding reagent that increases melting temperature of oligonucleotides with mismatch are selected to use in amplification.

A 25 ul amplification reaction contains templates, 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.25 u of AmpliTaq™ Gold DNA polymerase. Three-nucleotide primers are added typically to a concentration of 100 nm, 200 nM, 400 nM, or 800 nM. Mismatch binding reagents are added in the reaction to a concentration typically at a ratio to the concentration of primers of 1:1000, 1:100, 1:10, 1:1 10:1, 100:1, 1000:1. PCR cycling conditions are as following: 95° C. 10 minutes, 10 cycles of (95° C. 15 seconds, 60° C. 30 seconds), and 50 cycles of (95° C. 15 seconds, 65° C. 30 seconds).

Example 8: Comparison of Primer Dimer Formation Between Three Nucleotide Primers and Four Nucleotide Primers We have compared primer dimer formation between three nucleotide primer with three nucleotide dNTPs and four nucleotide primer with four nucleotide dNTPs. In this example, we compared primer dimer formation for one more situation, three nucleotide primers with four nucleotide dNTPs. The three-nucleotide-type primers were designed to amplify human genomic sequences targeting Hemoglobin (Hemo1F, Hemo1R, Hemo2F, Hemo2R), PPIA (PPIAF and PPIAR), GAPDH (GAPDHF, GAPDHR), and YWHZ (YWHZ1F, YWHZ1R, YWHZ2F, YWHZ2R). The four-nucleotide-type primers (regular 1-12) were designed for HPV detection, but were used here to compare with three nucleotide primers. All reactions contained 12 oligos.

A 25 ul PCR reaction contained 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.875 u of AmpliTaq™ Gold DNA polymerase. In the reactions with 4 dNTPs, 0.2 mM dCTP is added. Both three-nucleotide-type primers and regular four-nucleotide-type primers were added to a total concentration of 2.62 uM. PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds). No template was present. After conducting PCR, the mix was run on 1.5% agarose gel. Any detectable products would be the result of amplification from primer dimer formation.

FIG. 9 shows the agarose gel image. Lane 1 is a DNA ladder. Lane 2 is three-nucleotide-type primers with three nucleotide dNTPs. Lane 3 is three-nucleotide-type primers with four nucleotide dNTPs. Lane 4 is four-nucleotide-type primers with four nucleotide dNTPs. Both reactions with three-nucleotide-type primers did not have any visible products, whereas four nucleotides primers formed primer dimers in the absence of template.

Example 9: PCR with Constrained Primers with 1 or 2 Underrepresented Nucleotides Certain templates are not suitable to design three nucleotide-type primers. For example, a primer may be unsuitable when a mismatch is very close to the 3' end of one or both primers, or when many mismatches have to be present. In such case, constrained primers with 1 or 2 underrepresented nucleotides can be used. These primers can still have mismatches with template if necessary, but have no more than 2 underrepresented nucleotides to minimize primer-primer interactions.

Two sets of primers were designed for human genomic sequence targeting atm and csflr. ATM_F and ATM_R each contains 1 G and 2 mismatches. CSF1R_F and CSF1R_R each contains 2 Gs. The expected product sizes are 301 bp and 232 bp. A 25 ul PCR reaction contained 10 ng human genomic DNA, 10 mM Tris-HCl (pH8.3), 50 mM KCl, 2 mM MgCl2, 0.2 mM dATP, 0.2 mM dTTP, 0.2 mM dGTP, 0.2 mM dCTP, 1×SYBR™ green II, 400 nM each primer, and 1.25 u of AmpliTaq™ Gold DNA polymerase. PCR cycling was carried out on StepOne™ Real-Time PCR System. Cycling conditions were as following: 95° C. 10 minutes, 10 cycles of (95° C. 15 seconds, 60° C. 30 seconds, 72° C. 30 seconds), and 35 cycles of (95° C. 15 seconds, 65° C. 30 seconds, 72° C. 30 seconds). PCR products were run on 1.5% agarose gel.

FIG. 10A shows an agarose gel image. Lane 1 is DNA ladder. Lane 2 is atm PCR product. Lane 3 is csflr PCR product.

No template control reactions were conducted to compare primer dimer formation of constrained primers and regular four nucleotide primers. A 25 ul PCR reaction contained 10 mM Tris-HCl (pH8.3), 50 mM KCl, 2 mM MgCl2, 0.2 mM dATP, 0.2 mM dTTP, 0.2 mM dGTP, 0.2 mM dCTP, 1×SYBR™ green II, and 1.875 u of AmpliTaq™ Gold DNA polymerase. Both constrained primers (ATC-1G-1 to ATC-1G-10, ATC-2G-1 to ATC-2G-10) and regular four nucleotides primers (regular 1-10) were multiplexed with 10 oligonucleotides and added to a total concentration of 50 uM. PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds). Fluorescence signal was collected at the annealing step.

FIG. 10B shows fluorescence over time for constrained primers with 1G (underrepresented nucleotide). FIG. 10C shows fluorescence over time for constrained primers with 2Gs. FIG. 7D shows fluorescence over time for regular four-nucleotide-type primers. Both constrained primers reduced primer dimer formation and false positive amplification was undetectable until 40 cycles. The regular four nucleotides primers had strong primer-primer interactions and false positive amplification consistently appeared at about 25 cycles.

Example 10: Toehold Primer

When certain target sequences need to be amplified and no three-nucleotide-type sequence of sufficient length is available for the target, a toehold primer can be used. Both 5' segment and 3' segment of the toehold primers can bind to target sequence, therefore primer-template hybridization is with higher efficiency than the efficiency of the short three-nucleotide-type primer. Three-nucleotide-type artificial linker then serves as template for extension and provide sufficient primer-template binding length for later cycles. With omission of one type of nucleotide triphosphate monomers, the four-nucleotide-type nature of the 5' segment of toehold primer doesn't significantly increase unintended amplification. Toehold primers can also be provided in low concentrations to further lower the chance of unintended amplification.

A 25 ul PCR reaction contains templates, 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.25 u of AmpliTaq™ Gold DNA polymerase. Three-nucleotide primers are added typically to a concentration of 100 nM, 200 nM, 400 nM, or 800 nM. The toehold primers are added typically to a concentration of 1 nM, 10 nM, 100 nM, 200 nM, 400 nM, 800 nM. PCR cycling conditions are as following: 95° C. 10 minutes, 10 cycles of (95° C. 15 seconds, 60° C. 30 seconds), and 50 cycles of (95° C. 15 seconds, 65° C. 30 seconds).

Example 11: Three Way Junction Format for Three Nucleotide Primer

FIG. 16A shows a template to be amplified. In FIG. 16B, the four-nucleotide-type 5' region (sequence 4) of the 3 way junction helper hybridizes to template. The forward primer (sequence 1) hybridizes to the template next to the hybridization region of sequence 4. The artificial segments linked to the 5' end of forward primer (sequence 2) and the 3' end of 3 way junction helper (sequence 3) are complementary to each other and hybridize together to stabilize the full structure and initiate polymerase extension. On the other strand, a reverse primer hybridizes and extend in the three nucleotide region where sequence 1 hybridizes. In FIG. 16C, forward primer extension product hybridizes to reverse primer and generates full length products. A three way junction format can be applied to both primers.

A 25 ul PCR reaction contains templates, 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.25 u of AmpliTaq™ Gold DNA polymerase. Three-nucleotide primers are added typically to a concentration of 100 nM, 200 nM, 400 nM, or 800 nM. The three way junction helpers are added typically to a concentration of 1 nM, 10 nM, 100 nM, 200 nM, 400 nM, 800 nM.PCR conditions are as following: 95° C. 10 minutes, 10 cycles of (95° C. 15 seconds, 60° C. 30 seconds), and 50 cycles of (95° C. 15 seconds, 65° C. 30 seconds).

Example 12: Three Nucleotide Mismatch Primer or Constrained Primer PCR with Limited Amount of One of Four Nucleotide Monophosphate When three-nucleotide-type primers with G absent and with at least one mismatch are used for amplification with three nucleotide monophosphates, primer extension stops when dCTP is required. The intermediate products will hybridize to each other or hybridize to primers to extend to full products. When dCTP is provided in limited amount, incorporation of dCTP in primer extension generates more template, therefore will generate more intermediate products for three nucleotides primer PCR, which increases PCR efficiency. Constrained primers preferably contain no more than 2 Gs. When template permits, dCTP is provided in a limited amount so that it is sufficient for PCR extension; however it still limits the formation of primer dimer or non-specific amplification with template.

A set of primers are designed for HPV containing 1 Gin forward primer and 2Gs (11-1G-F, 11-2G-R) in reverse primer. A 25 ul PCR reaction contained 1 pg HPV11 DNA, 10 mM Tris-HCl (pH8.3), 50 mM KCl, 2 mM MgCl2, 0.2 mM dATP, 0.2 mM dTTP, 0.2 mM dGTP, 4×SYBR™ green II, 400 nM each primer, and 1.875 u of AmpliTaq™ Gold DNA polymerase. In the reactions with dCTP, dCTP was added at 1 uM (1/200 of regular amount). PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds). Fluorescence signal was collected at the annealing step.

FIG. 11A shows fluorescence over time for constrained primer PCR with 1 uM dCTP. FIG. 11B shows fluorescence over time for constrained primer PCR with no dCTP. FIG. 11C shows fluorescence over time for constrained primer and no template control with 1 uM dCTP. As low as 1 uM dCTP is sufficient for amplification with constrained primers. When no dCTP is provided, primer extension stops when dCTP is required. Therefore only short double-strand products are formed, giving a delayed amplification curve and low amplification signal. In the no template control, with 1 uM dCTP, no primer dimer formed in 60 cycles.

Example 13: Reducing Non-Specific Amplification in Multiplex PCR with Three-Nucleotide-Type Primers by Adding Fourth Nucleotide Monophosphate as ddNTP Three-nucleotide-type primers can also reduce non-specific template amplification because primers cannot extend long sequences without dCTP at non-specific priming site. When ddCTP is provided in a PCR reaction, any time non-specific primer extension meets a G on the template, ddCTP is incorporated and prevents this product from further extension. However, specific three nucleotide primer PCR does not incorporate ddCTP, and is therefore not affected by addition of ddCTP. We designed three nucleotide primers for HPV56 detection in patient cervical samples. Human genomic DNA is always present in patient samples at high amount. Occasionally HPV56 primers can react with human genomic DNA and have non-specific amplification when no HPV56 DNA is present. When ddCTP is added in the reaction at 0.2 mM, non-specific amplification rate is reduced to an undetectable level.

A 25 ul PCR reaction contained 100 ng human genomic DNA template, 10 mM Tris-HCl (pH8.3), 50 mM KCl, 2 mM MgCl2, 0.2 mM dATP, 0.2 mM dTTP, 0.2 mM dGTP, 1×SYBR™ green II, 400 nM each HPV56 and human YWHZ primers, and 1.875 u of AmpliTaq™ Gold DNA polymerase. For ddCTP reactions, 0.2 mM ddCTP is added. PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds).

Both HPV56 primers (56MM1F, 56MM1R) and human YWHZ primers (YWHZF1Tmtail, YWHZR1Tmtail) were used in the PCR reaction. The reaction with ddCTP was repeated so that we have a non-specifically amplified product. The reaction without ddCTP was repeated and no non-specific amplification was observed. FIG. 12 shows a gel image. Lane 1 is DNA ladder. Lane 2 shows YWHZ product at 116 bp and a non-specific HPV56 primer product at 81 bp when ddCTP is not provided. Lane 3 shows only YWHZ product is present when ddCTP is provided.

Example 14: Multiplex Detection of Multi-Templates with Melt Curve Analysis

As shown in example 13, we designed three-nucleotide-type HPV primers to detect HPV in patient samples and human YWHZ primers as internal control. When we use DNA intercalating dye SYBR™ green as signal detecting reagents, HPV and internal control were both detected with same dye. To differentiate the two types of reaction, the primers were modified so that PCR products of HPV and internal control have different Tm, and were separated with melting curve analysis. A negative control was performed with only human genomic DNA as template.

A 25 ul PCR reaction contained 10 pg HPV56 DNA template, 10 ng human genomic DNA template, 10 mM Tris-HCl (pH8.3), 50 mM KCl, 2 mM MgCl2, 0.2 mM dATP, 0.2 mM dTTP, 0.2 mM dGTP, 1×SYBR™ green II, and 1.875 u of AmpliTaq™ Gold DNA polymerase. Primer concentrations are 100 nM each primer. In negative sample, no HPV56 DNA is added. PCR cycling was carried out on StepOne™ Real-Time PCR System. Cycling conditions were as following: 95° C. 10 minutes, 10 cycles of (95° C. 15 seconds, 60° C. 30 seconds), and 50 cycles of (95° C. 15 seconds, 65° C. 30 seconds). Fluorescence signal was recorded at annealing step and melt curve analysis was performed at the end of cycling program.

FIG. 13A shows two well-resolved melt curves peaks generated at 72.47° C. and 79.86° C. corresponding to HPV56 and human YWHZ products. In contrast, in FIG. 13B, negative controls did not show a 72.47° C. melt curve peak indicating that no HPV56 was present.

Figure 22:
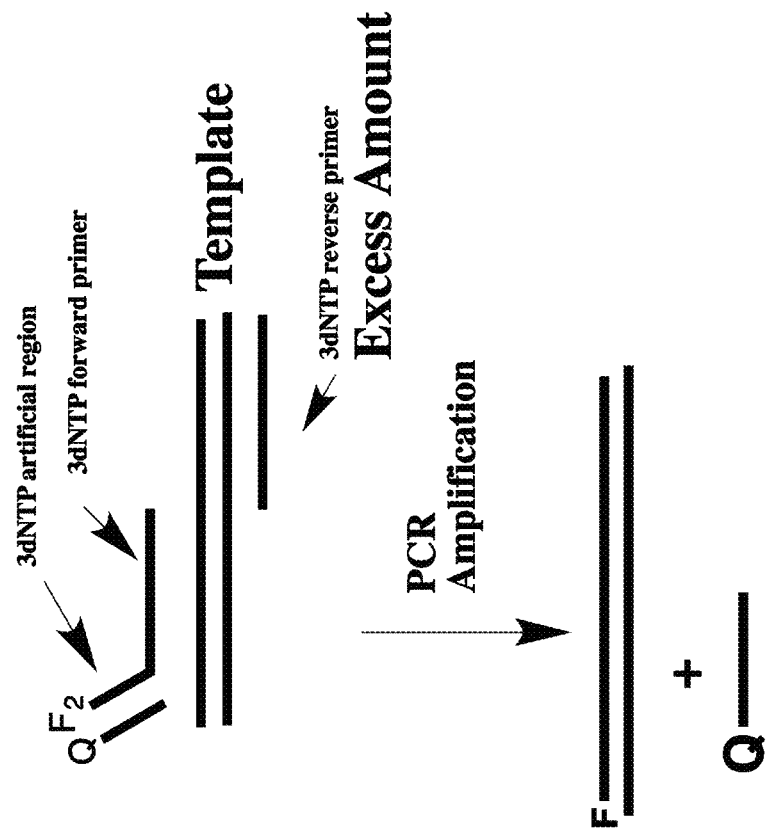
FIG. 22 shows asymmetric PCR with an excess of reverse primer.

Example 16: Real Time PCR Detection with Fluorescence Labeled Three Nucleotides Primer In addition to SYBR™ green based detection, we also tested fluorescence based detection with three nucleotides primers. Fluorescence labeled primers enable high multiplex and enable multiple channel detection in single tube reaction. We added an artificial three nucleotide tail to human YWHZ primers and labeled the tail with FAM fluorophore at 5' end, and a quencher labeled probe which is complementary to the artificial tail. We carefully designed the tail/probe sequence with lower Tm than those of primers so that extension can happen at a higher annealing temperature to ensure full extension to tailed region, before quenchers hybridize to free fluorescence primers at a lower temperature for signal detection. The assay can be facilitated with asymmetric primer concentration in the PCR reaction where reverse primer is provided in excess amount to preferentially generate strands that are detected by fluorescence labeled primer (FIG. 22). Because signal generation relies on reveres primer extension, excess amount of reverse primer enhances the signal and thereby the efficiency of the reaction.

A 25 ul PCR reaction contained 10 ng human genomic DNA template, 10 mM Tris-HCl (pH8.3), 50 mM KCl, 2 mM MgCl2, 0.2 mM dATP, 0.2 mM dTTP, 0.2 mM dGTP, 1.25 u of AmpliTaq™ Gold DNA polymerase, 100 nM fluorescence labeled primer, 100 nM BHQ™-probe, and 100 nM reverse primer. PCR cycling was carried out on StepOne™ Real-Time PCR System. Cycling conditions were as following: 95° C. 10 minutes, 60 cycles of (95° C. 15 seconds, 60° C. 30 seconds, 50° C. 30 seconds, and 50° C. 15 seconds). Fluorescence signal was recorded in the second 50° C. step.

FIG. 20A shows fluorescence over time for template amplification. FIG. 20B shows fluorescence over time for no template control reaction. 10 ng human genomic DNA is well detected with the FAM labeled primer. No amplification product from primer dimers was observed in the control.

Example 17: Multiplex PCR with Universal Fluorescence Labeled Primer

The directly fluorescence labeled primers from last example enable high level of multiplexing and multi-channel signal detection. However, individual labeling of primers is not cost efficient. In this example, we designed a fluorescence labeled universal primer which can detect multi products from multiplex reaction. In addition to regular three nucleotides PCR primers, we introduced a universal three nucleotide tail to the 5' end of each primer. In the reaction, a universal primer that has the same sequence as the primer tail is included. The universal primer was also tailed with a double-stranded sequence in which one strand is three nucleotide sequence and is labeled with a fluorophore and the complementary strand is labeled with a quencher. We used YWHZ primers to design the assay. We employed asymmetric PCR to preferentially generate strands that is detected by the universal primer. We demonstrated that the fluorescence labeled universal primer can be combined with three nucleotide multiplex PCR reaction to efficiently amplify multiple target sequences.

A 25 ul PCR reaction contained 100 ng human genomic DNA, 10 mM Tris-HCl (pH8.3), 50 mM KCl, 2 mM MgCl2, 0.2 mM dATP, 0.2 mM dTTP, 0.2 mM dGTP, 1.25 u of AmpliTaq™ Gold DNA polymerase, 100 nM fluorescence labeled universal primer, 100 nM BHQ™-probe, 100 nM tailed YWHZ forward primer and 400 nM YWHZ reverse primer. PCR cycling was carried out on BioRad CFX96 real time PCR machine. Cycling conditions were as following: 95° C. 10 minutes, 60 cycles of (95° C. 15 seconds, 60° C. 30 seconds, 50° C. 30 seconds, and 50° C. 15 seconds). Fluorescence signal was recorded second 50° C. step.

Figure 21:
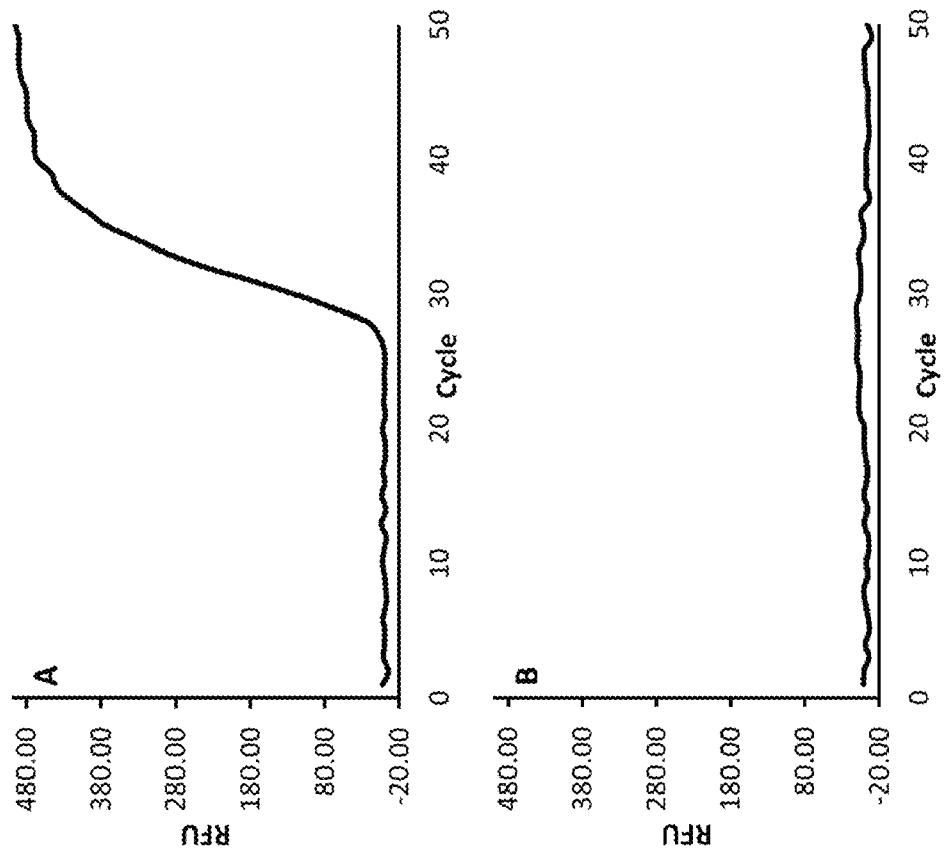
FIGS. 21A, B shows fluorescence over time for template amplification (A) and no template control (B).

FIG. 21A shows fluorescence over time for template amplification. FIG. 21B shows fluorescence over time for no template control reaction. 100 ng human genomic DNA was readily detected with the FAM labeled universal primer. No amplification product from primer dimer formation was detected in the no template control.

Example 18: Taqman® Probe Format

Instead of labeling fluorescence on primer, in this format, fluorescence is labeled on probe as Taqman® probe format. When reverse primer extend to the Taqman® probe, 5' exo activity of DNA polymerase digest the probe, releasing free fluorescence to be detected.

In this example, three nucleotide primers are tailed with universal artificial sequences. In PCR reaction, a Taqman® format probe is provides. The probe is complementary to the universal artificial sequence and labeled with a fluorophore and a quencher. PCR is conducted with one primer as said format or both primers as said format. When primer extension meet the Taqman® probe, 5' exo nuclease activity of DNA polymerase digests the probe and separates the fluorophore with quencher generating fluorescence signal.

A 25 ul PCR reaction contains templates, 10 mM Tris-HCl (pH8.3), 50 mM KCl, 2 mM MgCl2, 0.2 mM dATP, 0.2 mM dTTP, 0.2 mM dGTP, and 1.25 u of AmpliTaq™ Gold DNA polymerase. Three-nucleotide primers are added typically to a concentration of 100 nM, 200 nM, 400 nM, or 800 nM. The Taqman® probe is added typically at concentrations of 100 nM, 200 nM, 400 nM. PCR cycling conditions are as following: 95° C. 10 minutes, 60 cycles of (95° C. 15 seconds, 60° C. 30 seconds, 72° C. 60 seconds).

Example 19: Molecular Beacon Format

Fluorophore labeled molecular beacon is provided in reaction. Forward primer is tailed with a three nucleotides artificial sequence which contain same sequence as the molecular beacon. When reverse primer extend to the artificial sequence and generate its complement sequence. Molecular beacon hybridize to the sequence, fluorescence is no longer quenched and is detected.

In this example, three nucleotide primers are tailed with universal artificial sequences. In PCR reaction, a molecular beacon format probe is provides. The probe has hairpin structure and is labeled with a fluorophore and a quencher. As free probe, it remains hairpin structure and fluorophore is quenched. Its loop sequence is same as the universal artificial sequence. When PCR is conducted, primer extensions generate complementary sequence of the universal artificial sequence. Probe now hybridizes to the complementary sequence and is no longer the hairpin structure. This causes separation of fluorophore and quencher, generating fluorescence signal.

A 25 ul PCR reaction contains templates, 10 mM Tris-HCl (pH8.3), 50 mM KCl, 2 mM MgCl2, 0.2 mM dATP, 0.2 mM dTTP, 0.2 mM dGTP, and 1.25 u of AmpliTaq™ Gold DNA polymerase. Three-nucleotide primers are added typically to a concentration of 100 nM, 200 nM, 400 nM, or 800 nM. The molecular beacon probe are added typically at concentrations of 100 nM, 200 nM, 400 nM. PCR cycling conditions are as following: 95° C. 10 minutes, 60 cycles of (95° C. 15 seconds, 60° C. 30 seconds, 72° C. 60 seconds).

Example 20: Whole Genome Amplification

Constrained random three nucleotide primers containing one underrepresented nucleotide are tailed with artificial sequences. These random primers are used to amplify whole genomic DNA. PCR products is further amplified with universal primers, which are same sequences as the artificial sequences of random primers. The amplified products can be used for sequencing.

In contrast to PCR technology which is carried out with temperature cycles, three-nucleotide-type primers are also used in isothermal amplification which is carried out at a constant temperature and does not require a thermal cycler. Amplified product can be detected with addition of SYBR™ green or fluorescence labeled probes. Typically isothermal amplification is carried out with strand displacement DNA polymerase.

A 25 ul PCR reaction contains templates, 10 mM Tris-HCl (pH8.3), 50 mM KCl, 2 mM MgCl2, 0.2 mM dATP, 0.2 mM dTTP, 0.2 mM dGTP, 1×SYBR™ green II, and 2.5 u of AmpliTaq™ Gold DNA polymerase. Random primers are added typically to a concentration of 100 nM, 200 nM, 400 nM, 800 nM, 1 uM, 2 uM, 5 uM, or 10 uM. PCR cycling conditions are as following: 95° C. 10 minutes, 60 cycles of (95° C. 15 seconds, 60° C. 30 seconds, 72° C. 60 seconds). In secondary PCR reaction, products from previous reaction are diluted 1:10, 1:100, 1:1000, or 1:10000, and 1 ul of dilution is added as template. Universal primers are typically used at a concentration of 100 nM, 200 nM, 400 nM, or 800 nM. Other reagents are provided as a similar manner. For isothermal reaction, amplification is incubated at 60° C. for desired duration.

Example 21: Isothermal Amplification

Four types of isothermal amplification are shown in this example: Loop mediated isothermal amplification (LAMP), nicking enzyme amplification reaction (NEAR), transcription mediated amplification (TMA), rolling circle amplification (RCA), Helicase dependent amplification (HDA), Exponential amplification (EXPAR), Hybridization chain reaction (HCR), catalyzed hairpin assembly (CHA).

LAMP is typically performed in a total 25-100 ul reaction mixture containing 0.1-0.8 mM each of FIP and BIP, 0-0.2 mM each of the kick primers, 0.1-0.4 mM each of loop primers, 0.8-1.6 mM dNTPs, 0.25-1M betaine, 20 mM Tris-HCl (pH 8.8), 10 mM KCl, 10 mM (NH4)$_2$SO$_4$, 2-4 mM MgSO$_4$, 0.1% Triton™ X-100, 4-8 units of the Bst DNA polymerase large fragment (New England Biolabs) and the specified amounts of double-stranded target DNA. The mixture is incubated at 60° C. and analyzed in real time. The amplification is detected with SYBR™ green or fluorescence labeled probes.

NEAR is typically performed in a total 10-100 ul reaction mixture containing template, 45.7 mM Tris, 13.9 mM KCl, 10 mM (NH4)2SO4, 50 mM NaCl, 0.5 mM DTT, 15 mM MgCl2, 0.1% Triton™ X-100, 0.008 mM EDTA, 6 ug/mL BSA, 3.9% glycerol, 0.1-0.3 U/uL nicking enzyme, 0.1-0.4 U/uL strand displacement enzyme, 0.1-0.8 uM each primer. The mixture is incubated at 54-60° C. and the amplification is detected with fluorescence labeled probes.

TMA is typically performed in a total volume of 25-100 ul reaction mixture containing 2 mM each dNTP, 8 mM each rNTP, 80 mM Tris-HCl pH 7.5 at 25° C., 50 mM MgCl2, 35 mM KCl, 10% (w/v) polyvinylpyrrolidone and 0.1-1 uM primer with promoter sequence and reverse primer. Reaction mixture is incubated at 60° C. for 10 min under oil to allow denaturation of the RNA. The mixture was then cooled to 42° C. for 5 min before adding enzyme mix containing MMLV reverse transcriptase (2000 units/assay) and T7 RNA polymerase (2000 units/assay) in 8 mM Hepes pH 7.5, 50 mM N-acetyl-L-cysteine, 0.04 mM zinc acetate, 80 mM trehalose, 140 mM Tris-HCl pH 8.0 at 25° C., 70 mM KCl, 1 mM EDTA, 0.01% (w/v) phenol red, 10% (v/v) Triton™ X-100 and 20% (v/v) glycerol) and incubation continued for a further 60 min at 42° C.

RCA amplification reaction is typically performed in a 50 μl mixture containing template, 8 U Bst DNA polymerase (New England Biolabs), 100-800 nM of each RCA primer, and 400 μM dNTP mix. The mixture is incubated at 65° C. for 60 min and cooled at 10° C.

Amplification products are detected with SYBR™ green or fluorescence labeled probes and can be used in other applications.

HDA amplification reaction is typically performed in a 50 µl reaction containing the following reagents: 1×HDA Buffer (360 mM Tris-Acetate (pH7.5), 250 mM KOAC, 100 mM DTT, 1 mg/ml BSA, and 50 mM Magnesium Acetate), template, 0.1-0.8 µM each primer, 0.4 mMµl dNTPs, 4 mM ATP, DNA polymerase, helicase, and T4 gp32. Amplification reaction is performed without initial denaturation (e.g. reagents are added as described above), or with initial denaturation and annealing (e.g. DNA polymerase and helicase are added after initial step is done). The reaction is incubated for one hour at 37° C. Amplification products are detected with SYBR™ green or fluorescence labeled probes. The EXPAR amplification reaction is typically performed at 60° C. Reaction contains 85 mM KCl, 25 mM Tris-HCl (pH 8.8, 25° C.), 2.0 mM MgSO4, 5 mM MgCl2, 10 mM (NH4)2SO4, 0.1% (vol:vol) Triton™ X-100, 0.5 mMDTT, nicking enzyme, Vent exo-polymerase, 400 uM dNTPs, 10 ug/ml BSA, template, and primers. Amplification products are detected with SYBR™ green or fluorescence labeled probes.

HCR reaction is typically performed in 4-50 uL containing 1×HBN buffer (150 mM Na2HPO4 and 1.5 M NaCl, pH 6.8), 1.0 uM each of hairpin H1 and H2, and 0.1-1 uM initiator. The reaction is conducted with the following conditions: boiling in a water bath for 5 min followed by gradually cooling down to room temperature for 1 h.

CHA reaction is typically performed in 5-50 uL mixture containing 10-1000 nM each hairpin H1 and H2, 50-1000 nM reporter duplex (fluorophore labeled oligo: quencher labeled oligo=1:2, 1×TNaK buffer (20 mM Tris, pH 7.5; 140 mM NaCl; 5 mM KCl). H1 and H2 were separately refolded (90° C. for 1 min, followed by cooling to room temperature at 0.1° C./s) in TNaK Buffer immediately before use. Following addition of target oligo, reaction is incubated at 37° C. for fluorescence detection.

Sequence Listing

| | | SEQ. ID NO: |
|---|---|---|
| Regular primer 1 | gtccattgcaggtttactgtgcagcattcgagtgctggagcagatgtt | 1 |
| Regular primer 2 | gtgaaggtacaaatgaggaggggcgatattgtgtccctgtatgttttcc | 2 |
| Regular primer 3 | gtggtgttacaagtgtgacaacaggttaggaccggccagatggacaa | 3 |
| Regular primer 4 | agttcgtttatgtgtcaacagtacagcacaggtagggcacacaatattcactg | 4 |
| Regular primer 5 | cggtaccccctcgaagtcgtttgtccataccaaagcctgctccgt | 5 |
| Regular primer 6 | acaaccccaccaagcgagtgcgacccggtctttgtttgtgcagtcag | 6 |
| Regular primer 7 | ctaccagctgcagtgtgttgttacacgggatgaaccacagcgtca | 7 |
| Regular primer 8 | tagaagcctcacgggatactctgcgggtttgcagttgcacaccacg | 8 |
| Regular primer 9 | tcctagtgagtccataaacagctgctgctgcagctggtagtagaagcc | 9 |
| Regular primer 10 | gtgcaactgcaaaccagtaacctgctgcctgtactagaaaccatccgtt | 10 |
| Regular primer 11 | accgtggacttagatccgtctccacatgcaggaggcagcaagga | 11 |
| Regular primer 12 | agtgggcacaaaaaagcaaaacgacgctgagtctctgcagcttccacttc | 12 |
| Regular primer 13 | ctccactgctttccactgccagttgcgtgttacagaattgaagctccgt | 13 |
| Regular primer 14 | ccttcgcgttgtacagcagatgttagtccatcgccgttgctagt | 14 |
| Regular primer 15 | gccgtaatgtgctatcacaactgtgaggccagatggacaagcagaacaa | 15 |
| Regular primer 16 | gcattcatagcactgcgacggaccttctatagccgtgcacagccgg | 16 |
| Regular primer 17 | ggtctacttcatcctcatcctcatcctataccacaaactgagattgacctgc | 17 |
| Regular primer 18 | agccacagcaagctagacgggacgagccaactgcaccaacgactc | 18 |
| Regular primer 19 | caactgcaccacaaacttacactgacagcggccacagcaagctaga | 19 |
| Regular primer 20 | acattcagagtaccaaagaggacctgcgcgcagagtgggcacgttac | 20 |
| Regular primer 21 | ccgtccaagcctatttcatcctcgtctatttacatcctgaaccaactgacct | 21 |
| Regular primer 22 | atggacaagcacaaccggccacagctactgttgatacacaaacgaaccgtg | 22 |
| Regular primer 23 | atggtgtttattgctgtgcacagctagacaaccgacgtacgaaccct | 23 |
| Regular primer 24 | tggatgaccctgaaggtacaaacgggctcctgttcttcgttctattaccgc | 24 |
| Regular primer 25 | accgtggtgccacaagtgtaacgggccagatggacaagcacaac | 25 |
| Regular primer 26 | caacagtacaacaaccgacgtacgaactgtttattgctgtgcacagctagg | 26 |
| Regular primer 27 | ctcgcgctctgcctgtacacatgcaacagatacaggttcagactt | 27 |

-continued

Sequence Listing

| | | SEQ. ID NO: |
|---|---|---|
| Regular primer 28 | gcacaggccttgtttaatgtgcaggatctatactgcacccaaactttcgtt | 28 |
| Regular primer 29 | ccataagcagctgttgtaccacacgtgtgagttggtggtgcagttg | 29 |
| Regular primer 30 | aacgtgcccactctgcgcaccacaacatcccatcccctcc | 30 |
| Regular primer 31 | caactgcaccaccaactcacacttacaacagcaagctagacaagctgaac | 31 |
| Regular primer 32 | ccaaagaggagctacgtgtggtacaacccattgcagttatttagatgatgcgc | 32 |
| ATCrandom1 | aatacctcctcactctcacccaatttctcccccaacaccc | 33 |
| ATCrandom2 | acaccacacataatttcacctctctatctcccaccccccac | 34 |
| ATCrandom3 | tccccctcccttactcccatttcaccttaaccttcccaac | 35 |
| ATCrandom4 | ccataaactactcccatatcttcccattcccttcctccc | 36 |
| ATCrandom5 | aactaccatccttctctacatcctctccaaatctccccccc | 37 |
| ATCrandom6 | cacaccataccatcccactcccatttactttctacccctc | 38 |
| ATCrandom7 | tcctatccccccttccatatcaccccctatccccttcacc | 39 |
| ATCrandom8 | accactcttcctcacaacatatccttcctccacccacacc | 40 |
| ATCrandom9 | aaccccctacaaaatccccaccaccaaccccatctacacc | 41 |
| ATCrandom10 | ccaccaccaactataacttcattcctctcacttccctccc | 42 |
| ATCrandom11 | accccttaaaacccacctactccatacctcccctcaaccc | 43 |
| ATCrandom12 | atcccccatacccaatctctatcctatcacaccaaccacc | 44 |
| ATCrandom13 | acacctaattaccctctccaaccttactccctcattcccc | 45 |
| ATCrandom14 | cttacacactcttccatcctccctctaaaccacctctctc | 46 |
| ATCrandom15 | ccccattttaacccctcccaaacaacacctacaactccc | 47 |
| ATCrandom16 | cccactacatctttcccttctactcctacctactcccatc | 48 |
| ATCrandom17 | aacctccacctaccattcctcccacaactcacacaccctc | 49 |
| ATCrandom18 | ctttatacccccaaaccatatcctttacccccttccctccc | 50 |
| ATCrandom19 | ctcctccattcaccttccacctcttttcaaacccaacacc | 51 |
| ATCrandom20 | aatccccaccaaaccatctactatcattccctccatcccc | 52 |
| ATCrandom21 | aattaaacttcctccacccttccttccaaccaccccacac | 53 |
| ATCrandom22 | taactcaactaatttcttaccttccacctcccccccctcc | 54 |
| ATCrandom23 | taccccctacccacacccccctcaactaaaccatacactaac | 55 |
| ATCrandom24 | ccctcattttctcaaacacaaccctcctcactctccc | 56 |
| ATCrandom25 | ctatacccatccctaaacacatcaactccaccctcttccc | 57 |
| ATCrandom26 | tcccaatcctatctcacactccttctccacccccccaacc | 58 |
| ATCrandom27 | tctccctactaactaaccatcctcccctccaaaccacttc | 59 |
| ATCrandom28 | ctaccccctctactactactcacaccccccactaacttac | 60 |
| ATCrandom29 | cccatacatcaaactctcattatccctccaccccccaccc | 61 |
| ATCrandom30 | ttcaccccccaaaccatcccttccctctcactccctcctc | 62 |
| ATCrandom31 | atattaacacccttctccctcacatcccccacttccttccc | 63 |
| ATCrandom32 | acaacaaacctcccccctaaaccaaccaacccctcctaac | 64 |
| Hemo2F | aatttctattaaaccttcctttcttccctaactccaactactaaac | 65 |

-continued

| | Sequence Listing | SEQ. ID NO: |
|---|---|---|
| Hemo2R | cacaatccacatcctcaaccccttcataatatccccc | 66 |
| HPV11-1F | cttatcttacctccacacctaataccctttcacaatc | 67 |
| HPV11-1R | ccaccatacccaccactattttctacatcatc | 68 |
| HPV11MM1F | tacaatcaacaacatcctcactcacaattacaac | 69 |
| HPV11MM1R | taaacaaccacacaaacaaccatctatcaccatc | 70 |
| Hemo1F | cccttcatcttttcttttcccccttcttttc | 71 |
| Hemo1R | ccctcttacttctcccctcctatcacatcaacttaacc | 72 |
| PPIAF | ctcttactctaccatttcccttctatttaaccccttctattc | 73 |
| PPIAR | ccaaatctccaaccttcaaactttaaacccaacttcaaac | 74 |
| GAPDHF | ccatcaataaactaccctctcctcaaccacttacttctcctctcttattc | 75 |
| GAPDHR | ccaccttccctcccctctccccacaccc | 76 |
| YWHZF1 | cccttttccttacttttctcatcaaatcattccaacaacc | 77 |
| YWHZR1 | tttctcaattccacataccaatttctaatccc | 78 |
| YWHZF2 | tcttttccatctcccatcatcccctctcttcctcccaccc | 79 |
| YWHZR2 | tttctaatcaatccccccctctcccacaaaaaataccaactcattttttttc | 80 |
| ATM_F | cttattcccaaggcctttaaactgttcacctcac | 81 |
| ATM_R | catatactgaagatcacacccaagctttccatcc | 82 |
| CSF1R_F | ctccctgtcgtcaactcctc | 83 |
| CSF1R_R | ccctcccaccctcaggactataccaatc | 84 |
| ATC-1G-1 | aatacctcctcactctcacccaatttctcccccaagaccc | 85 |
| ATC-1G-2 | acaccacacataatttcacctctctatctcccaccccgac | 86 |
| ATC-1G-3 | tcccctcccttactcccatttcaccttaacgttcccaac | 87 |
| ATC-1G-4 | ccataaactactcccatatcttcccattcccgttcctccc | 88 |
| ATC-1G-5 | aactaccatccttctctacatcctctccaaatctgccccc | 89 |
| ATC-1G-6 | cacaccataccatcccactcccatttagtttctacccctc | 90 |
| ATC-1G-7 | tcctatccccccttccatatcaccccctatcccccttcagc | 91 |
| ATC-1G-8 | accactcttcctcacaacatatccttcctccagccacacc | 92 |
| ATC-1G-9 | aaccccctacaaaatccgcaccaccaaccccatctacacc | 93 |
| ATC-1G-10 | ccaccaccaactataacttcattcctgtcacttccctccc | 94 |
| ATC-2G-1 | aatacctcctcactctcacccaatttctcccccaagaccc | 95 |
| ATC-2G-2 | acaccacacataatttcacctctctatctcccagcccgac | 96 |
| ATC-2G-3 | tcccctcccttactcccatttcaccttaacgttccgaac | 97 |
| ATC-2G-4 | ccataaactactcccatatcttcccattcccgttcctgcc | 98 |
| ATC-2G-5 | aactaccatccttctctacatcctctccaaatctggcccc | 99 |
| ATC-2G-6 | cacaccataccatcccactcccatttagtttctacgcctc | 100 |
| ATC-2G-7 | tcctatccccccttccatatcaccccctatcccccttgagc | 101 |
| ATC-2G-8 | accactcttcctcacaacatatccttcgtccagccacacc | 102 |

| Sequence Listing | | SEQ. ID NO: |
|---|---|---|
| ATC-2G-9 | aaccccctacaaaatccgcaccaccagccccatctacacc | 103 |
| ATC-2G-10 | ccaccaactataacttcattcctgtcacttgcctccc | 104 |
| 11-1G-F | ccctttacatttccaaatccattcccctttgac | 105 |
| 11-2G-R | catctcatagttcatatactgcattcccatttc | 106 |
| 56MM1F | attactctctcactaaccacaataccaaaacaaacattccc | 107 |
| 56MM1R | ccaaccctaccctaaatacccctatattcatatccactaac | 108 |
| YWHZF1Tmtail | accacacacccacaccaccacccacacccctttccttactttctcatcaaatcattccaacaacc | 109 |
| YWHZR1Tmtail | cccttcctctcctctccctctcaactttctcaattccacataccaatttctaatccc | 110 |
| YWHZF1tailed F | FAMacctccaccctcccccttttccttactttctcatcaaatcattccaacaacc | 111 |
| YWHZF1universal tailed | accacacacccacaccaccacccacccctttccttactttctcatcaaatcattccaacaacc | 112 |
| UP F | FAMacctccaccctccaccacacacccacaccaccacccac | 113 |
| QuencherProbe | ggagggtggaggtBHQ™ | 114 |

What is claimed is:

1. A method of amplifying a predetermined segment of a target nucleic acid comprising:
   contacting a sample comprising a target nucleic acid with forward and reverse primers; and
   conducting an amplification reaction wherein an amplification product of the predetermined segment of the target nucleic acid is formed by extension of the forward and reverse primers with the target nucleic acid serving as a template; wherein
   the primers are underrepresented in one or more of the four standard nucleotide types, the underrepresented nucleotide type(s) being the same in the primers, in each primer, the underrepresented nucleotide type(s) being present at two or fewer internal positions and/or the 5' end position; and where the primers are not random primers in which most or all primer positions are occupied by degenerate selections of nucleotides varying between the primers, and
   wherein the method is performed in multiplex with one or more further pairs of the forward and reverse primers forming amplification products of one or more further predetermined segments, the underrepresented nucleotide type(s) being the same for each of the one or more further pairs, and in each primer of each pair, as the underrepresented nucleotide type(s) in the forward and reverse primers, the underrepresented nucleotide type(s) being present at two or fewer internal positions and/or the 5' end position in each primer of the one or more further pairs.

2. The method of claim 1, wherein the target nucleic acid has a strand comprising a complement of a forward primer binding site and a reverse primer binding site.

3. The method of claim 2, wherein the forward and reverse primers have greater complementarity to the forward and reverse primer binding sites than to any other pair of primer binding sites supporting amplification in the sample.

4. The method of claim 2, wherein the forward primer binding site and the reverse primer binding site are underrepresented in the complement of the underrepresented nucleotide type(s) in the forward and reverse primers.

5. The method of claim 1, wherein the forward and reverse primers have one and only one of the four standard nucleotide types underrepresented.

6. The method of claim 1, wherein the forward and reverse primers have no more than one unit of the underrepresented nucleotide type(s), and the forward primer binding site and the reverse primer binding site have no more than three units of the complement of the underrepresented nucleotide type(s).

7. The method of claim 1, wherein the underrepresented nucleotide type(s) in the forward and reverse primers do not occupy the 3' positions of the forward and reverse primers.

8. The method of claim 1, wherein the forward and reverse primers consist of the three standard nucleotide types other than the underrepresented nucleotide type, and the forward primer binding site and the reverse primer binding site consist of the three standard nucleotide types other than the complement of the underrepresented nucleotide type in the forward and reverse primers.

9. The method of claim 1, wherein the forward and reverse primer each have one unit of the underrepresented nucleotide type(s) at the 5' end.

10. The method of claim 1, wherein the complement of the forward primer binding site and the reverse primer binding site are contiguous.

11. The method of claim 1, wherein the complement of the forward primer binding site and the reverse primer binding site are separated by a region excluding the underrepresented nucleotide type in the forward and reverse primers and its complement.

12. The method of claim 1, wherein the complement of the forward primer binding site and the reverse primer binding site are separated by a region including the underrepresented nucleotide type(s) in the forward and reverse primers or its complement or both.

13. The method of claim 1, wherein the 3' nucleotide of the forward and/or reverse primers is the complement of one of the underrepresented nucleotide type(s) in the forward and reverse primers.

14. The method of claim 1 wherein the 3' nucleotide of the forward and/or reverse primers is C or G.

15. The method of claim 1, wherein the forward and/or reverse primer contains an unnatural nucleotide, which is inosine, isoC, isoG, 7-deaza-2'-deoxyguanosine, or 7-deaza-2'-deoxyadenosine.

16. The method of claim 1, wherein the forward and/or reverse primer is linked at its 5' end to an artificial oligonucleotide having the same underrepresented nucleotide type(s) as the forward and/or reverse primers.

17. The method of claim 1, wherein the amplification is performed with nucleotide triphosphate monomers, with the nucleotide triphosphate monomers complementary to the underrepresented nucleotide type(s) in the forward and reverse primers being omitted, or wherein the complementary nucleotide triphosphate monomer(s) of the nucleotide type(s) underrepresented in the forward and reverse primers are present at a reduced concentration relative to the other nucleotide triphosphate monomers.

18. The method of claim 1, further comprising searching a sequence of a strand of the target nucleic acid for the complement of the forward primer binding site and the reverse primer binding site, wherein the searching is performed with a computer programmed to identify the complement of the forward primer binding site and the reverse primer binding site, by looking for ATC and ATG regions, ATG and ATC regions, CGA and CGT regions, or CGT and CGA regions.

19. The method of claim 1, wherein the forward primer binding site and/or the reverse primer binding site include at least one unit of the complementary nucleotide type(s) of the underrepresented nucleotide type(s) in the forward and reverse primers and the hybridization of the primers and primer binding sites results in at least one mismatch.

20. The method of claim 19, wherein the amplification is performed in the presence of a mismatch stabilizing agent.

21. The method of claim 1, wherein the forward and/or reverse primer is linked at its 5' end to a linker segment of artificial sequence having the same underrepresented nucleotide type(s) as the forward or reverse primer, which is linked at its 5' end to a 5' segment including all four standard nucleotide types and complementary to the target nucleic acid.

22. The method of claim 1, wherein the forward and/or reverse primer is a primer segment linked at its 5' end to an artificial segment which has the same underrepresented nucleotide type(s) as the primer segment, and the amplification is performed with a junction primer comprising a target binding site and the complement of the artificial segment; and the target binding site of the junction primer includes all four standard nucleotides.

23. The method of claim 1, wherein the forward and/or reverse primer is linked at its 5' end to a double-stranded oligonucleotide, one of the strands of which has the same underrepresented nucleotide type(s) as the primer to which it is linked, wherein the artificial double-stranded oligonucleotide has a melting temperature different than the amplification product formed by extension of the forward and reverse primers; wherein formation of the amplification product is detected by a melt curve analysis, wherein the melting temperature transitions from that of the artificial double-stranded oligonucleotide to that of the amplification product.

24. The method of claim 23, wherein a forward and/or reverse primer of a pair of the further forward and reverse primers is linked to a different artificial segments with a different melting temperatures than the artificial segment linked to the forward and/or reverse primer.

25. The method of claim 1, wherein the forward and/or reverse primer is linked at its 5' end to an artificial oligonucleotide sequence having the same underrepresented nucleotide type(s) as the primer to which it is linked, and the amplification product of the predetermined segment is detected with a fluorophore and quencher labeled oligonucleotide having the same sequences as the 5' end artificial oligonucleotide, which hybridizes to a complementary strand of the 5' end artificial oligonucleotide formed during the amplification reaction, thereby separating the fluorophore and quencher to generate a fluorescent signal indicating presence of the amplification product of the predetermined segment.

26. The method of claim 1, wherein the forward and/or reverse primers is linked at its 5' end to a single-stranded artificial oligonucleotide having the same underrepresented nucleotide type(s) as the primer to which it is linked, the artificial oligonucleotide being labeled with a fluorophore and quencher, whereby the amplification product of the predetermined segment formed by extension of the forward and reverse primers separates the fluorophore and quencher generating a fluorescent signal indicating the presence of the amplification product of the predetermined segment.

27. The method of claim 1, wherein the forward and/or reverse primer is linked at its 5' end to a fluorescently labeled tail having the same underrepresented nucleotide type(s) as the primer it is linked to.

28. The method of claim 1, wherein the forward and/or reverse primer is supplied with a fluorescently labeled tail hybridized to an oligonucleotide labelled with a quencher, wherein the oligonucleotide dissociates from the primer during the amplification separating the quencher from the fluorescently labeled tail generating a fluorescent signal.

29. The method of claim 1, performed in multiplex with multiple pairs of the forward and reverse primers with different target binding regions linked to tails with different fluorescent labels.

30. The method of claim 1, performed in multiplex with multiple pairs of the forward and/or reverse primers with different target binding regions linked to a common 5' artificial segment, and the amplification is performed with a detection probe having a 3' segment complementary to the complement of the common 5' artificial segment.

31. The method of claim 1, wherein the forward and/or reverse primer is linked at its 5' end to an artificial tail with the same underrepresented nucleotide type as the primer to which it is linked, and the primer is supplied hybridized to an oligonucleotide comprising a fluorophore and a quencher wherein the quencher or fluorophore is cleaved from the oligonucleotide in the amplification generating a fluorescent signal.

32. The method of claim 1, wherein the forward and/or reverse primer is linked at its 5' end to a tail that is underrepresented in the same nucleotide type(s) as the primer to which it is linked, and a molecular beacon oligonucleotide is provided comprising a hairpin with a loop hybridizing to the complement of the 5' tail, and a fluorophore and quencher at its ends, wherein the molecular beacon oligonucleotide hybridizes to the amplification product of the predetermined segment thereby separating the fluorophore and quencher and generating a fluorescent signal.

33. The method of claim 1, wherein the forward and/or reverse primer has a 3' single-strand sticky end and a hairpin loop structure at its 5' end segment and the last nucleotide at the 5' end of the hairpin loop structure is the complement of an underrepresented nucleotide type.

34. The method of claim 33, wherein the amplification product of the predetermined segment is ligated to form a ligated product.

35. The method of claim 33, wherein the amplification product of the predetermined segment is ligated to form a circular product.

36. The method of claim 1, wherein the sample is contacted with the forward and reverse primers at different concentrations from one another.

37. The method of claim 1, wherein the amplification is performed with temperature cycling.

38. The method of claim 1, wherein the amplification is performed isothermally.

39. The method of claim 1, wherein the amplification product of the predetermined segment is detected by melting curve analysis, capillary electrophoresis, mass spectroscopy, real-time fluorescence detection, sequencing or a hybridization to a microarray.

40. The method of claim 39, wherein the amplification product of the predetermined segment is detected by emergence of its melt peak.

41. The method of claim 1, wherein the forward or reverse primer is linked to an enzyme recognition segment.

42. The method of claim 41, wherein the enzyme recognition segment is a nuclease or promoter recognition site.

43. The method of claim 1, wherein the one or more further predetermined segments are on the target nucleic acid.

44. The method of claim 1, wherein the one or more further predetermined segments are on different target nucleic acid(s) than the target nucleic acid.

* * * * *

UNITED STATES PATENT AND TRADEMARK OFFICE
CERTIFICATE OF CORRECTION

PATENT NO.         : 11,091,799 B2
APPLICATION NO.    : 15/569080
DATED              : August 17, 2021
INVENTOR(S)        : Youxian Wang et al.

Page 1 of 1

It is certified that error appears in the above-identified patent and that said Letters Patent is hereby corrected as shown below:

In the Claims

Column 101, Claim 24, Line 58, delete "segments" and insert --segment--

Column 101, Claim 24, Line 59, delete "temperatures" and insert --temperature--

Column 101, Claim 25, Line 67, delete "sequences" and insert --sequence--

Column 102, Claim 26, Line 8, delete "primers" and insert --primer--

Signed and Sealed this
First Day of March, 2022

Drew Hirshfeld
*Performing the Functions and Duties of the*
*Under Secretary of Commerce for Intellectual Property and*
*Director of the United States Patent and Trademark Office*